(12) United States Patent
Larman et al.

(10) Patent No.: US 12,091,776 B2
(45) Date of Patent: Sep. 17, 2024

(54) PROTEASE ACTIVITY PROFILING VIA PROGRAMMABLE PHAGE DISPLAY OF COMPREHENSIVE PROTEOME-SCALE PEPTIDE LIBRARIES

(71) Applicant: THE JOHNS HOPKINS UNIVERSITY, Baltimore, MD (US)

(72) Inventors: Harry B. Larman, Baltimore, MD (US); Gabriel Roman-Melendez, Towson, MD (US); Thiagarajan Venkataraman, Ellicott City, MD (US)

(73) Assignee: The John Hopkins University, Baltimore, MD (US)

( * ) Notice: Subject to any disclaimer, the term of this patent is extended or adjusted under 35 U.S.C. 154(b) by 744 days.

(21) Appl. No.: 16/913,572

(22) Filed: Jun. 26, 2020

(65) Prior Publication Data
US 2020/0407467 A1    Dec. 31, 2020

Related U.S. Application Data

(60) Provisional application No. 62/867,319, filed on Jun. 27, 2019.

(51) Int. Cl.
  *C40B 40/08*  (2006.01)
  *C07K 17/06*  (2006.01)
  *C12N 7/00*  (2006.01)
  *C12N 15/63*  (2006.01)
  *C12Q 1/6869*  (2018.01)

(52) U.S. Cl.
  CPC .............. *C40B 40/08* (2013.01); *C07K 17/06* (2013.01); *C12N 7/00* (2013.01); *C12N 15/63* (2013.01); *C12Q 1/6869* (2013.01); *C07K 2317/34* (2013.01); *C07K 2319/43* (2013.01)

(58) Field of Classification Search
None
See application file for complete search history.

(56) References Cited

U.S. PATENT DOCUMENTS 9,731,034 B2    8/2017 Bossmann et al.

OTHER PUBLICATIONS

Wang et al. (2016) International Journal of Molecular Sciences vol. 17 article 1940 pp. 1 to 15.*
Novagen 2011 TB178 system manual pp. 1 to 24.*
Novagen 2011 TB182VM vector map pp. 1 to 2.*
Kretz et al. (Feb. 12, 2018) Scientific Reports vol. 8 article 27888 pp. 1 to 13.*

(Continued)

*Primary Examiner* — Christian C Boesen
(74) *Attorney, Agent, or Firm* — Johns Hopkins Technology Ventures

(57) ABSTRACT

The present invention relates to the field of proteases. More specifically, the present invention provides compositions and methods useful for profiling protease activity using phage display. In one embodiment, a display vector useful for profiling protease activity comprises a nucleic acid sequence encoding (a) a peptide to be displayed on the surface of the vector; (b) a first affinity tag C-terminal to the peptide; and (c) a second affinity tag N-terminal to the peptide. The display vector can comprise a virus, bacteriophage, yeast, bacteria, retrovirus, ribosome or mRNA. In particular embodiments, the peptide comprises a human peptidome library peptide.

33 Claims, 16 Drawing Sheets

Specification includes a Sequence Listing.

(56) References Cited

OTHER PUBLICATIONS

Fairhead et al. (2015) Methods in Molecular Biology vol. 1266 pp. 171 to 184.*
Fischer. Mechanism of the proteolytic activity of malignant tissue cells. Nature., (1946), 157, pp. 442.
Schilling et al. Protease specificity profiling by tandem mass spectrometry using proteome-derived peptide libraries. Methods Mol Biol., (2011), 753, pp. 257-272.
Klinger et al. Profiling protease activities by dynamic proteomics workflows. Proteomics., (2012), 12 (4-5), pp. 587-596.
Aiche et al. Inferring proteolytic processes from mass spectrometry time series data using degradation graphs. PloS One., (2012), 7 (7), e40656.
Dudani et al. Classification of prostate cancer using a protease activity nanosensor library. Proceedings of the National Academy of Sciences of the United States of America., (2018), 115 (36), pp. 8954-8959.
Ong et al. Recent developments in protease activity assays and sensors. Analyst., (2017), 142 (11), pp. 1867-1881.
Zhang. Protease Assays. In: Sittampalam GS, Grossman A, Brimacombe K, et al., editors. Assay Guidance Manual [Internet]. Bethesda (MD): Eli Lilly & Company and the National Center for Advancing Translational Sciences. (2004).
Nicholls et al. Mechanism of a genetically encoded dark-to-bright reporter for caspase activity. J Biol Chem., (2011), 286 (28), pp. 24977-24986.
Deperthes. Phage display substrate: a blind method for determining protease specificity. Biol Chem., (2002), 383 (7-8), pp. 1107-1112.
Matthews et al. Substrate phage: selection of protease substrates by monovalent phage display. Science., (1993), 260 (5111), pp. 1113-1117.
Kridel et al. Substrate hydrolysis by matrix metalloproteinase-9. J Biol Chem., (2001), 276 (23), pp. 20572-20578.
Beck et al. Molecular basis for the relative substrate specificity of human immunodeficiency virus type 1 and feline immunodeficiency virus proteases. J Virol., (2001), 75 (19), pp. 9458-9469.
Beck et al. Identification of efficiently cleaved substrates for HIV-1 protease using a phage display library and use in inhibitor development. Virology., (2000), 274 (2), pp. 391-401.
Thorpe et al. Extended cleavage specificity of human neutrophil cathepsin G: A low activity protease with dual chymase and tryptase-type specificities. PloS One., (2018), 13 (4), e0195077.
Kretz et al. High throughput protease profiling comprehensively defines active site specificity for thrombin and ADAMTS13. Sci Rep., (2018), 8 (1), pp. 2788.
Kretz et al. Massively parallel enzyme kinetics reveals the substrate recognition landscape of the metalloprotease ADAMTS13. Proceedings of the National Academy of Sciences of the United States of America., (2015), 112 (30), pp. 9328-9333.
Larman et al. Autoantigen discovery with a synthetic human peptidome. Nat Biotechnol., (2011), 29 (6), pp. 535-541.
Xu et al. Systematic autoantigen analysis identifies a distinct subtype of scleroderma with coincident cancer. Proceedings of the National Academy of Sciences of the United States of America., (2016), 113 (47), pp. E7526-E7534.
Larman et al. PhIP-Seq characterization of autoantibodies from patients with multiple sclerosis, type 1 diabetes and rheumatoid arthritis. Journal of Autoimmunity., (2013), 43, pp. 1-9.
Larman et al. et al. Cytosolic 5'-nucleotidase 1A autoimmunity in sporadic inclusion body myositis. Annals of Neurology., (2013), 73 (3), pp. 408-418.
Mohan et al. PhIP-Seq characterization of serum antibodies using oligonucleotide-encoded peptidomes. Nature Protocols., (2018), 13 (9), pp. 1958-1978.
Biniossek et al. Identification of Protease Specificity by Combining Proteome-Derived Peptide Libraries and Quantitative Proteomics. Molecular & Cellular Proteomics., (2016), 15 (7), pp. 2515-2524.
Mahrus et al. Global Sequencing of Proteolytic Cleavage Sites in Apoptosis by Specific Labeling of Protein N Termini. Cell., (2008), 134 (5), pp. 866-876.
Nomura et al. Activity-based protein profiling for biochemical pathway discovery in cancer. Nature Reviews Cancer., (2010), 10 (9), pp. 630-638.
Poreba et al. Highly sensitive and adaptable fluorescence-quenched pair discloses the substrate specificity profiles in diverse protease families. Scientific Reports., (2017), 7, 43135.
Li et al. Profiling Protease Specificity: Combining Yeast ER Sequestration Screening (YESS) with Next Generation Sequencing. ACS Chem. Biol., (2017), 12 (2), pp. 510-518.
Chen et al. Oligopeptide immobilization strategy for improving stability and sensitivity of liquid-crystal protease assays. Sensors and Actuators B Chemical., (2014), 204, pp. 734-740.
Bao et al. Toward more accurate prediction of caspase cleavage sites: a comprehensive review of current methods, tools and features. Briefings in Bioinformatics., (2019), 20 (5), pp. 1669-1684.
Kretz et al., High throughput protease profiling comprehensively defines active site specificity for thrombin and ADAMTS13. Sci Rep 8, 2788. 2018.

* cited by examiner

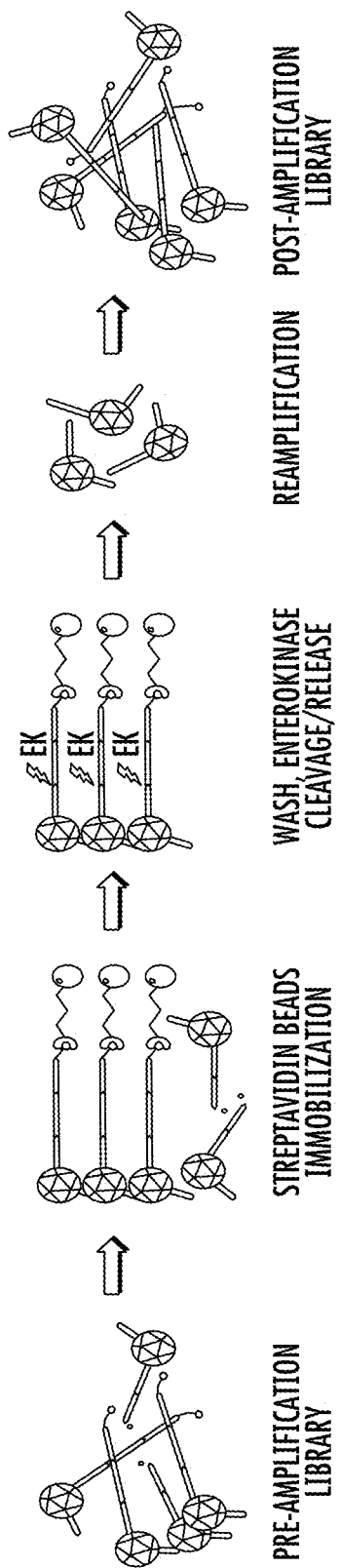

PROTEASE ACTIVITY PROFILING VIA PROGRAMMABLE PHAGE DISPLAY OF COMPREHENSIVE PROTEOME-SCALE PEPTIDE LIBRARIES

CROSS-REFERENCE TO RELATED APPLICATIONS

This application claims the benefit of U.S. Provisional Application No. 62/867,319, filed Jun. 27, 2019, which is incorporated herein by reference in its entirety.

FIELD OF THE INVENTION

The present invention relates to the field of proteases. More specifically, the present invention provides compositions and methods useful for profiling protease activity using phage display.

INCORPORATION-BY-REFERENCE OF MATERIAL SUBMITTED ELECTRONICALLY

This application contains a sequence listing. It has been submitted electronically via EFS-Web as an ASCII text file entitled "P15808-02_ST25.txt." The sequence listing is 49,166 bytes in size, and was created on Jun. 25, 2020. It is hereby incorporated by reference in its entirety.

BACKGROUND OF THE INVENTION

Protein cleavage is a fundamental molecular process that is highly regulated and is essential to cellular viability as well as tissue physiology across all kingdoms of life. Human proteases comprise a large and diverse set of enzymes, with at least 569 members that make up five distinct catalytic classes. In cancer, protease activities are often dysregulated and in many cases, contribute to the selective growth advantage of tumor cells. Well-known examples include the downregulation of pro-apoptotic caspases and upregulation of matrix remodeling metalloproteinases. The proteolytic machinery of tumor-associated myeloid cells can also be co-opted to alter the immune microenvironment. The lack of an efficient, comprehensive assay has severely limited our ability to characterize protease activities contained within biological samples. Consequently, there are large gaps in our knowledge regarding which proteases are active in which diseases and at what frequency. Further, the proteomic spectrum of potential cleavage substrates is well defined only for a small number of intensively investigated proteases.

Previous approaches for unbiased measurement of protease activity include mass spectrometry based profiling, multiplexed or microarray based analysis of labeled candidate peptide substrates, and single-plex live cell reporter assays. In general, mass spectrometry-based methods suffer from high cost, low throughput, low sensitivity, and complex analyses that often rely on an indirect inference of activities. Multiplexed peptide substrate based measurements rely on peptide synthesis, which is costly, low throughput and restricted to the analysis of candidate activities. Cell based assays can be used to monitor real-time proteolytic activities in living cells, but cannot readily be multiplexed beyond 2-3 substrates.

Detection technologies based on DNA analysis can provide extremely high sensitivity, made possible by robust signal amplification via the polymerase chain reaction (PCR). As such, "bacteriophage display" of random peptide libraries has been used to characterize the recognition motifs of purified, recombinant proteases. While such studies have demonstrated the utility of the phage display system for analysis of specific proteases, this approach has not been generalized to the unbiased characterization of protease activities present within complex samples

SUMMARY OF THE INVENTION

Endopeptidases catalyze the internal cleavage of proteins, playing pivotal roles in protein turnover, substrate maturation and the activation of signaling cascades. A broad range of biological functions in health and disease are controlled by proteases, yet assays to characterize their activities at proteomic scale do not yet exist. To address this unmet need, the present inventors have developed SEPARATE (Sensing EndoPeptidase Activity via Release and recapture using flAnking Tag Epitopes). In certain embodiments, SEPARATE uses monovalent phage display of the entire human proteome at 90-aa peptide resolution. The present inventors demonstrate that SEPARATE is compatible with several human proteases from distinct catalytic classes, including Caspase-1, ADAM17, and Thrombin. Both well-characterized and newly identified substrates of these enzymes were detected in the assay. In addition, SEPARATE was used to discover a non-canonical Caspase-1 substrate, the E3 ubiquitin ligase HUWE1, a key mediator of apoptotic cell death. As described herein, SEPARATE is a novel methodology to enable efficient, unbiased assessment of endopeptidase activity using a phage-displayed proteome.

As described herein, the present invention provides a platform enabling the facile, inexpensive and unbiased profiling of human protease activities. In particular embodiments, cancer-associated proteolytic activities have the potential to serve as catalytic diagnostic and/or prognostic biomarkers detectable in the peripheral blood, and/or as targets of novel therapies, including the potential to act as local pro-drug activators.

Accordingly, in one aspect, the present invention provides a bacteriophage display vector. In one embodiment, a bacteriophage display vector comprises a nucleic acid sequence encoding (a) a peptide to be displayed on the surface of the bacteriophage; (b) a first affinity tag C-terminal to the peptide; and (c) a second affinity tag N-terminal to the peptide. The bacteriophage can comprise any bacteriophage including, but not limited to, T7 and M13. In particular embodiments, the peptide comprises a human peptidome library peptide.

In one embodiment, the first affinity tag comprises a biotin labeling tag. In a specific embodiment, the second affinity tag comprises at least one FLAG tag. In a more specific embodiment, the second affinity tag comprises a 3× FLAG tag.

In another embodiment, the bacteriophage display vector further comprises an enterokinase cleavage site N-terminal to the peptide. In other embodiments, the bacteriophage display vector further comprises an epitope tag between the peptide and the first affinity tag. In a specific embodiment, the epitope tag comprises a V5 tag.

The bacteriophage display vector can further comprise a protease cleavage site between the peptide and the first affinity tag. In a specific embodiment, the protease comprises the TEV protease.

In another aspect, the present invention provides a bacteriophage peptide display library. In certain embodiments, a bacteriophage peptide display library comprises a plurality of bacteriophage display vectors each comprising a nucleic acid sequence encoding (a) a peptide to be displayed on the surface of the bacteriophage; (b) a first affinity tag C-terminal to the peptide; and (c) a second affinity tag N-terminal to the peptide. The bacteriophage can comprise any bacteriophage including, but not limited to, T7 and M13. In particular embodiments, the displayed peptides comprise the human peptidome.

In one embodiment, the first affinity tag comprises a biotin labeling tag. In a specific embodiment, the second affinity tag comprises at least one FLAG tag. In a more specific embodiment, the second affinity tag comprises a 3× FLAG tag.

In another embodiment, the bacteriophage display vector of the bacteriophage peptide display library further comprises an enterokinase cleavage site N-terminal to the peptide. In other embodiments, the bacteriophage display vector further comprises an epitope tag between the peptide and the first affinity tag. In a specific embodiment, the epitope tag comprises a V5 tag.

The bacteriophage display vector of the bacteriophage peptide display library can further comprise a protease cleavage site between the peptide and the first affinity tag. In a specific embodiment, the protease comprises the TEV protease.

In particular embodiments, the displayed peptides of the bacteriophage peptide display library comprise at least 10 proteins. In certain embodiments, the displayed peptides of the bacteriophage peptide display library are each less than 100, 200 or 300 amino acids long. In further embodiments, each displayed peptide of the bacteriophage peptide display library comprises a common adapter region appended to the end of the nucleic acid sequence encoding the peptide.

In another aspect, the present invention provides methods for profiling protease activity. In one embodiment, a method for profiling protease activity comprises the steps of (a) contacting a reaction sample comprising a bacteriophage peptide display library described herein, with a capture agent that specifically binds the first affinity tag to form an immobilized bacteriophage peptide display library; (b) contacting the immobilized bacteriophage peptide display library with a sample comprising at least one protease under conditions that would allow the at least one protease to cleave at least one displayed peptide, thereby releasing a population of at least one composition comprising the bacteriophage particle, the second affinity tag N-terminal to the peptide and a first portion of the cleaved peptide; (c) isolating the population of step (b) with a capture agent that specifically binds the second affinity tag; and (d) amplifying deoxyribonucleic acid (DNA) within the bacteriophage particle that encodes the displayed peptide. In a specific embodiment, in step (a), the binding of the capture agent to the first affinity tag forms an irreversibly immobilized bacteriophage peptide display library.

In another embodiment, the method further comprises the step of (e) sequencing the amplified DNA of step (d). In more specific embodiments, the sequencing step comprises next generation sequencing. In another embodiment, the method further comprises the step of (e) performing microarray hybridization to detect the amplified sequences of step (d).

In particular embodiments, step (d) comprises real-time polymerase chain reaction (PCR). In other embodiments, the amplified DNA of step (d) further comprises a DNA proxy. In a specific embodiment, the DNA proxy is a peptide-specific barcode sequence.

In yet another aspect, the present invention provides a display vector. In one embodiment, a display vector comprises a nucleic acid sequence encoding (a) a peptide to be displayed on the surface of the vector; (b) a first affinity tag C-terminal to the peptide; and (c) a second affinity tag N-terminal to the peptide. The display vector can comprise a virus, bacteriophage, yeast, bacteria, retrovirus, ribosome or mRNA. In particular embodiments, the peptide comprises a human peptidome library peptide.

In one embodiment, the first affinity tag comprises a biotin labeling tag. In a specific embodiment, the second affinity tag comprises at least one FLAG tag. In a more specific embodiment, the second affinity tag comprises a 3× FLAG tag.

In another embodiment, the display vector further comprises an enterokinase cleavage site N-terminal to the peptide. In other embodiments, the display vector further comprises an epitope tag between the peptide and the first affinity tag. In a specific embodiment, the epitope tag comprises a V5 tag.

The display vector can further comprise a protease cleavage site between the peptide and the first affinity tag. In a specific embodiment, the protease comprises the TEV protease.

In another aspect, the present invention provides a peptide display library. In certain embodiments, a peptide display library comprises a plurality of display vectors each comprising a nucleic acid sequence encoding (a) a peptide to be displayed on the surface of the display vector; (b) a first affinity tag C-terminal to the peptide; and (c) a second affinity tag N-terminal to the peptide. The display vector can comprise a virus, bacteriophage, yeast, bacteria, retrovirus, ribosome or mRNA. In particular embodiments, the displayed peptides comprise the human peptidome.

In one embodiment, the first affinity tag comprises a biotin labeling tag. In a specific embodiment, the second affinity tag comprises at least one FLAG tag. In a more specific embodiment, the second affinity tag comprises a 3× FLAG tag.

In another embodiment, the display vector of the peptide display library further comprises an enterokinase cleavage site N-terminal to the peptide. In other embodiments, the display vector further comprises an epitope tag between the peptide and the first affinity tag. In a specific embodiment, the epitope tag comprises a V5 tag.

The display vector of the peptide display library can further comprise a protease cleavage site between the peptide and the first affinity tag. In a specific embodiment, the protease comprises the TEV protease.

In particular embodiments, the displayed peptides of the peptide display library comprise at least 10 proteins. In certain embodiments, the displayed peptides of the peptide display library are each less than 100, 200 or 300 amino acids long. In further embodiments, each displayed peptide of the peptide display library comprises a common adapter region appended to the end of the nucleic acid sequence encoding the peptide.

In another aspect, the present invention provides methods for profiling protease activity. In one embodiment, a method for profiling protease activity comprises the steps of (a) contacting a reaction sample comprising the peptide display library described herein, with a capture agent that specifically binds the first affinity tag to form an immobilized peptide display library; (b) contacting the immobilized peptide display library with a sample comprising at least one protease under conditions that would allow the at least one protease to cleave at least one displayed peptide, thereby releasing a population of at least one composition comprising the display vector, the second affinity tag N-terminal to the peptide and a first portion of the cleaved peptide; (c) isolating the population of step (b) with a capture agent that specifically binds the second affinity tag; and (d) amplifying deoxyribonucleic acid (DNA) within the display vector that encodes the displayed peptide. In a specific embodiment, in step (a), the binding of the capture agent to the first affinity tag forms an irreversibly immobilized peptide display library.

In another embodiment, the method further comprises the step of (e) sequencing the amplified DNA of step (d). In more specific embodiments, the sequencing step comprises next generation sequencing. In another embodiment, the method further comprises the step of (e) performing microarray hybridization to detect the amplified sequences of step (d).

In particular embodiments, step (d) comprises real-time polymerase chain reaction (PCR). In other embodiments, the amplified DNA of step (d) further comprises a DNA proxy. In a specific embodiment, the DNA proxy is a peptide-specific barcode sequence.

BRIEF DESCRIPTION OF THE FIGURES

FIG. 1A: An oligonucleotide library encoding >29,000 human protein isoforms as 45 amino acid overlapping 90-mer tiles is synthesized on a DNA microarray and cloned into the T7-SEPARTATE vector. This monovalent display vector flanks a library peptide by an N-terminal 3×FLAG tag and a C-terminal biotin labeling tag. FIG. 1B: The biotin tagged library is immobilized on streptavidin-coupled magnetic beads, digested with a protease containing solution and digested phage clones are recaptured on M2 FLAG antibody coated protein G beads. FIG. 1C: Recaptured phage clones are amplified by PCR and their clonal abundance quantified by deep sequencing to generate a fold-enrichment matrix. FIG. 1D: T7-SEPARATE clones are biotin labeled in vivo and can be immobilized on streptavidin-coupled magnetic beads. X-axis: number of input phage particles per 10 µl streptavidin beads; y-axis: number of phage particles retained on beads after washing. FIG. 1E: A T7-SEPARATE clone encoding the PreScission cleavage motif -LGVLPG/GP- (SEQ ID NO:1) was prepared using both the T7Select1-2b monovalent (○) and the T7Select1-3b multivalent (◇) T7 vector scaffolds. A negative control clone lacking the PreScission cleavage motif is not enriched on M2 FLAG antibody coated beads for both monovalent (●) and multivalent (◆) display scaffolds. FIG. 1F: The PreScission digestible clone spiked into the human library demonstrates a dose-dependent enrichment (●); no enrichment is observed when digested with Caspase-1 (○). FIG. 1G: MA plot analysis from a PreScission digest compares a peptide's enrichment (Log[Protease/Buffer]) against its relative abundance in the human library (0.5*Log[Protease*Buffer]). "Protease" refers to 1 Unit of PreScission enzyme in a 50 µl reaction and "Buffer" refers to no PreScission enzyme in the reaction ("mock digest").

FIG. 2A: EpitopeFindr output as a network graph. Nodes represent Caspase-1 digested peptides and edges indicate regions of sequence homology. Multiple sequence alignment of the cluster containing the most peptides reveals a known Caspase cleavage motif. FIG. 2B: HUWE1 peptide tiles 51, 52 and 53 are cleaved by Caspase-1. FIG. 2C: Putative HUWE1 cleavage site identified by SEPARATE. FIG. 2D: Western blot analysis of the time-dependent cleavage of HUWE1 in unstimulated THP-1 lysate after addition of recombinant Caspase-1. FIG. 2E: HUWE1 (upper panel) and Gasdermin D (GSDMD, lower panel) are cleaved by endogenous Caspase-1 in THP-1 cells upon inflammasome activation with indicated amounts of LPS and 2.5 mM Nigericin.

FIG. 3A: Aggregated data from series of digests using Thrombin, ADAM17 and Caspase-1. Physiological concentrations for Thrombin and ADAM17 are 1-1,000 nM and 1-10 nM; A range for Capsase-1 is not reported. Cardiac troponin T (TNNT2; ●) is a known Thrombin substrate; Vasorin (VASN; ◆) is a known substrate of ADAM17; IL-1β (□) and HUWE1 (■) known substrates of Caspase-1. FIG. 3B-3C: MA plot analysis of Thrombin (2 pM), ADAM17 (0.4 nM) and (D) Caspase-1 in THP1 lysate (0.3 µM).

FIG. 5A-5B. Characteristics of the human peptidome library. FIG. 5A: Schematic showing the library purification and amplification steps after initial sub-cloning of the library. FIG. 5B: Left panel—Distribution of peptides in the post-amplification library (grey) and library bound to streptavidin coated magnetic beads (red). Right panel—Distribution of just the C-terminal peptides with stop codons upstream of the AviTag.

FIG. 6A: A scatter plot comparing two replicates of T7-SEPARATE performed in the absence of protease (buffer only or 'mock' digest) shows that the assay is very reproducible (R2=0.74) and produces no spurious enrichments. FIG. 6B: A scatter plot of two replicates of a Caspase-1 screen with an R2 value of 0.95, showing high correlation between replicates. FIG. 6C: A scatter plot between Caspase-1 and PreScission data (R2=0.072) illustrates the discordance between SEPARATE data from two different proteases, which will contain enrichments specific to each protease.

FIG. 8A: IL-1β has two reported Caspase-1 cleavage sites after positions D26 and D117. Fold enrichments were higher for three peptides (7.5, 13 and 9-fold respectively) containing these cleavage sites compared to peptides from other regions of IL-1β (~1 fold). Mouse IL-1β amino acid sequence is shown in SEQ ID NO:73. FIG. 8B: Gsdmd has one reported Caspase-1 cleavage site at position D276. The two overlapping peptides containing this cleavage motif is enriched 4 and 7-fold respectively, compared to peptides from other regions of Gsdmd (~1 fold enrichment). Two peptides around the 100-140 amino acid region show 3-3.5 fold enrichment suggesting a secondary cleavage site that has not been previously reported. The sequence shown below the plots highlight the aspartic acid residue after which Caspase-1 cleavage occurs in red/bold. Overlapping regions between two adjacent peptides are highlighted in red. Mouse Gsdmd amino acid sequence is shown in SEQ ID NO:77.

DETAILED DESCRIPTION OF THE INVENTION

Figure 1C:
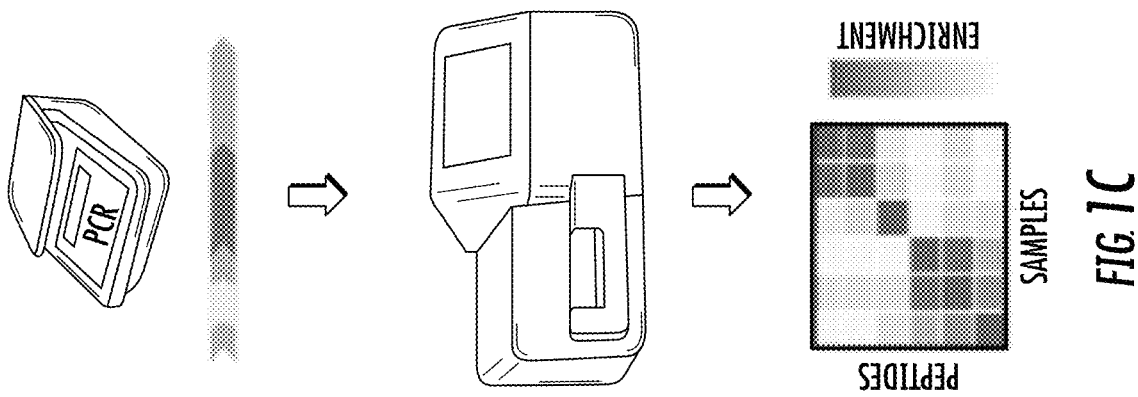
FIG. 1A-1G. SEPARATE design and workflow.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "display library" refers to a library comprising a plurality of peptides that are displayed on the surface of a virus or cell e.g., bacteriophage, yeast, or bacteria. Methods for using such phage, yeast or bacterial display libraries are well known to those of skill in the art. In some embodiments, the peptides are derived from the human peptidome. Moreover, the term "display library" includes, but is not limited to, a viral display library, a bacteriophage display library, a yeast display library, and a bacterial display library, as well as a retroviral display library, a ribosome display library or an mRNA display library. A bacteriophage may comprise any type of bacteriophage including, but not limited to, T7 and M13. Although the description herein may refer to a bacteriophage library, it is understood that such a term applies to other type of display libraries and that one of skill in the art can apply the teachings herein with respect to bacteriophage libraries to the construction and use of other types of display libraries.

As used herein, the term "to the protein from which it is derived" refers to a step of correlating or mapping at least one displayed peptide to a sequence in the known sequences of the proteins, thereby identifying the protein that comprises the peptide sequence.

As used herein, the term "enriched" indicates that a peptide is represented at a higher proportion in the display library after cleavage with a protease, compared to its representation in the starting library or the library after "mock" cleavage no protease was input into the reaction. In some embodiments, the peptides are enriched by at least 10% as compared to the general population. In other embodiments, the peptides are enriched by at least 20%, at least 30%, at least 40%, at least 50%, at least 60%, at least 70%, at least 80%, at least 90%, at least 95%, at least 99%, at least 1-fold, at least 2-fold, at least 5-fold, at least 10-fold, at least 25-fold, at least 50-fold, at least 100-fold, at least 1000-fold, or more, compared to the general population.

As used herein the term "oligonucleotide primers" refers to nucleic acid sequences that are 5 to 100 nucleotides in length, preferably from 17 to 45 nucleotides, although primers of different length are of use. Primers for synthesizing cDNAs are preferably 10-45 nucleotides, while primers for amplification are preferably about 17-25 nucleotides. Primers useful in the methods described herein are also designed to have a particular melting temperature (Tm) by the method of melting temperature estimation. Commercial programs, including OLIGO™, Primer Design and programs available on the internet, including PRIMERS and OLIGO CALCULATOR can be used to calculate a Tm of a polynucleotide sequence useful according to the methods and assays described herein. Preferably, the Tm of an amplification primer useful according to the invention, as calculated for example by OLIGO CALCULATOR, is preferably between about 45 and 65° C. In other embodiments, the Tm of the amplification primer is between about 50 and 60° C.

As used herein, the term "sample" refers to a biological material which is isolated from its natural environment and contains at least one protease. A sample according to the methods described herein, may consist of a purified or isolated protease, or it may comprise a biological sample such as a tissue sample, a biological fluid sample, or a cell sample comprising a protease. A biological fluid includes, but is not limited to, blood, plasma, sputum, urine, cerebrospinal fluid, lavages, and leukaphoresis samples, for example.

As used herein the term "adapter sequence" refers to a nucleic acid sequence appended to a nucleic acid sequence encoding a phage-displayed peptide. In one embodiment, the identical adaptor sequence is appended to the end of each phage-displayed peptide encoding DNA in the phage display library; that is, the adaptor sequence is a common sequence on each nucleic acid of the plurality of nucleic acids encoding a peptide in the phage display library. In one embodiment, the adaptor sequence is of sufficient length to permit annealing of a common PCR primer. For example, adaptor sequences useful with the methods described herein are preferably heterologous or artificial nucleotide sequences of at least 15, and preferably 20 to 30 nucleotides in length. An adapter sequence may comprise a barcode sequence.

The term "specifically binds" refers to an agent, compound or, in certain embodiments, an antibody that recognizes and binds a peptide of the invention, but which does not substantially recognize and bind other molecules in a sample, for example, a biological sample, which may comprise a peptide of the invention. The term specifically refers to the binding of an affinity tag to a corresponding capture agent to which it specifically binds (e.g., biotin-streptavidin).

As used herein, the term "amplified product" refers to polynucleotides which are copies of a portion of a particular polynucleotide sequence and/or its complementary sequence, which correspond in nucleotide sequence to the template polynucleotide sequence and its complementary sequence. An "amplified product," can be DNA or RNA, and it may be double-stranded or single-stranded.

A recited range is meant to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

II. Displayed Peptides

The displayed peptides may comprise all or a portion of the human peptidome. One of skill in the art can design synthetic oligonucleotide libraries to encode peptide tiles that together span a library of protein sequences (entire proteomes, for example). The result is a comprehensive and normalized (uniform in abundance) representation of the encoded peptides, which is referred to as the peptidome.

In some embodiments, the peptide sequences of the phage display library are at least 1 amino acids long; in other embodiments the peptide sequences are at least 20, at least 30, at least 40, at least 50, at least 60, at least 70, at least 80, at least 90, at least 100, at least 150, at least 200, at least 250, at least 300, at least 350, at least 400, at least 450 amino acids or more in length. In particular embodiments, the peptide sequences are 90-mer.

In some embodiments, each peptide of the phage library will overlap at least one other peptide by at least 5 amino acids. In other embodiments, each peptide of the phage library will overlap at least one other peptide by at least 10, at least 15, at least 20, at least 21, at least 22, at least 23, at least 24, at least 25, at least 26, at least 27, at least 28, at least 29, at least 30, at least 32, at least 35, at least 40, at least 45, at least 50, at least 55, at least 60, at least 65, at least 70, at least 75, at least 80, at least 85, at least 90, at least 95, at least 100 amino acids or more. In particular embodiments, the peptides overlap by 45 amino acids.

III. Production of a Phage Display Library

General methods for producing a phage display library are known to those of skill in the art and/or are described in, for example, Larman et al., 29(6) NAT. BIOTECH. 535-41 (2011), which is incorporated herein by reference in its entirety.

Unlike the conventional art, contemplated herein are phage display libraries that comprise a plurality of peptides derived from the human peptidome. In one embodiment, it is contemplated herein that the plurality of peptides will represent a substantially complete set of peptides from the human peptidome.

In some embodiments, the phage display library comprises less than 10,000 peptide sequences. In other embodiments, the phage display library comprises less than 9000, less than 8000, less than 7000, less than 6000, less than 5000, less than 4000, less than 3000, less than 2000, less than 1000, less than 750, less than 500, less than 250, less than 100, less than 50 or less than 25 peptide sequences. In other embodiments, the phage display library comprises at least 100, at least 200, at least 500, at least 1000, at least 5000, at least 10,000 peptide sequences or more. It will be appreciated by one of ordinary skill in the art that as the length of the individual peptide sequences increases, the total number of peptide sequences in the library can decrease without loss of any protein sequences (and vice versa).

In some embodiments, the phage display library comprises peptides derived from at least 10 protein sequences, at least 20 protein sequences, at least 30 protein sequences, at least 40 protein sequences, at least 50 protein sequences, at least 60 protein sequences, at least 70 protein sequences, at least 80 protein sequences, at least 90 protein sequences, at least 100 protein sequences, at least 200 protein sequences, at least 300 protein sequences, at least 400 protein sequences, at least 500 protein sequences, at least 600 protein sequences, at least 700 protein sequences, at least 800 protein sequences, at least 900 protein sequences, at least 1000 protein sequences, at least 2000 protein sequences, at least 3000 protein sequences, at least 4000 protein sequences, at least 5000 protein sequences, at least 6000 protein sequences, at least 6500 protein sequences, at least 7000 protein sequences, at least 7500 protein sequences, at least 8000 protein sequences, at least 8500 protein sequences, at least 9000 protein sequences, at least 10,000 protein sequences or more.

In some embodiments, the phage display library comprises a plurality of peptide sequences that have less than 90% shared identity; in other embodiments the plurality of peptide sequences have less than 85% shared identity, less than 80% shared identity, less than 75% shared identity, less than 70% shared identity, less than 65% shared identity, less than 60% shared identity, less than 55% shared identity, less than 50% shared identity or even less.

In some embodiments, the phage display library comprises peptide sequences from at least 3 unique proteins or at least 5 unique proteins; in other embodiments the library comprises peptide sequences from at least 10, at least 20, at least 50, at least 75, at least 100, at least 200, at least 300, at least 400, at least 500, at least 600, at least 700, at least 800, at least 900, at least 1000 unique proteins.

In some embodiments, the phage display library comprises at least 2 peptides from the human peptidome. In other embodiments, the display library comprises at least 3, at least 4, at least 5, at least 6, at least 7, at least 8, at least 9, at least 10, at least 15, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 11000, at least 12000, at least 13000, at least 14000, at least 15000, at least 16000, at least 17000, at least 18000, at least 19000 peptides or more as selected in any desired combination from the human peptidome. In some embodiments, the display library comprises all of the peptides in the human peptidome.

Again, while the disclosure specifically recites phage display libraries, it is specifically contemplated herein that other display libraries can be used with the methods and assays described herein including, but not limited to, a yeast display library, a bacterial display library, a retroviral display library, a ribosome display library or an mRNA display library. It is within the skills of one of ordinary skill in the art to apply the methods and assays exemplified herein using a phage display library to the use of a different type of display library.

IV. Reaction Samples

As used herein, the term "reaction sample" refers to a sample that, at a minimum, comprises a phage display library, for example, a phage display library described herein.

In particular embodiments, reaction sample comprising the phage display library is contacted with a capture agent that specifically binds to the first affinity tag displayed on the surface of the bacteriophage. For example, in a specific embodiment, the first affinity tag comprises a biotin labeling tag. The capture agent may comprise avidin, streptavidin, neutravidin, captavidin, and the like. In particular embodiments, the capture agent can be coated onto a solid surface (e.g., beads) and used to create an immobilized phage display library. In such embodiments, the immobilized phage display library is ready to be contacted with a sample comprising at least one protease.

The reaction sample can also comprise additional buffers, salts, osmotic agents, etc., to facilitate the cleavage of peptides in the phage display library when the reaction sample is contacted with a biological sample comprising protease. A "biological sample" as that term is used herein refers to a fluid or tissue sample derived from a subject that comprises or is suspected of comprising at least one protease. Alternatively, a "sample" may comprise a solution that comprises or is suspected of comprising at least one protease.

A biological sample can be obtained from any organ or tissue in the individual to be tested, provided that the biological sample comprises, or is suspected of comprising, an antibody. Typically, the biological sample will comprise a blood sample, however other biological samples are contemplated herein, for example, mucosal secretions.

In some embodiments, a biological sample is treated to remove cells or other biological particulates. Methods for removing cells from a blood or other biological sample are well known in the art and can include, e.g., centrifugation, ultrafiltration, immune selection, sedimentation, etc. Antibodies can be detected from a biological sample or a sample that has been treated as described above or as known to those of skill in the art. Some non-limiting examples of biological samples include a blood sample, a urine sample, a semen sample, a lymphatic fluid sample, a cerebrospinal fluid sample, a plasma sample, a serum sample, a pus sample, an amniotic fluid sample, a bodily fluid sample, a stool sample, a biopsy sample, a needle aspiration biopsy sample, a swab sample, a mouthwash sample, a cancer sample, a tumor sample, a tissue sample, a cell sample, a synovial fluid sample, or a combination of such samples. For the methods described herein, it is preferred that a biological sample is from whole blood, plasma, saliva, serum, and/or urine. In one embodiment, the biological sample is serum.

In some embodiments, samples can be obtained from an individual with a disease. In certain embodiments, samples from a normal demographically matched individual and/or from a patient not having the disease are used in the analysis to provide controls. The samples can comprise a plurality of sera or plasma from individuals sharing a trait. For example, the trait shared can be gender, age, genotype, disease state, and the like.

V. Recovery of Phage Displaying Peptides Cleaved During the Assay

In particular embodiments, the immobilized phage display library is contacted with a sample comprising at least one protease. The protease cleaves at least one displayed peptide, releasing a population of at least one composition comprising the bacteriophage particle, the second affinity tag N-terminal to the peptide and a first portion of the cleaved peptide. The reaction sample also comprises a population of at least one composition comprising a second portion of the cleaved peptide and the first affinity tag bound to the capture agent. The reaction sample further comprises uncleaved immobilized bacteriophage page display library members, wherein the at least one protease in the reaction sample did not cleave the displayed peptide.

In certain embodiments, it is desirable to capture phage particles that were released into solution during the cleavage step of the assay. This post cleavage recovery is accomplished via binding of a flanking peptide sequence (e.g., the second affinity tag) that is positioned between the phage and the protease-cleaved peptide. Post cleavage recovery results in (i) concentrating the released phage for downstream analysis, and (ii) removing phage particles and genomes that were nonspecifically released into solution during the cleavage step, via dislocation of the displayed peptide or particle breakage.

The affinity tag (first and/or second) can be any affinity tag known in the art and includes, but is not limited to, polyhistidine, Glutathione S-transferase, biotin, antigen, HA (YPYDVPDYA (SEQ ID NO:46)) c-Myc (EQKLISEED (SEQ ID NO:47)), FLAG (DYKDDDK (SEQ ID NO:48)), V5 (GKPIPNPLLGLDST (SEQ ID NO:49)), Maltose binding protein, and HaloTag. Capture agents the specifically bind such affinity tags are known in the art and include, but are not limited to, metal ions, glutathione, streptavidin, anti-HA antibody or antigen-binding fragment thereof, anti-Myc antibody or antigen-binding fragment thereof, anti-FLAG antibody or antigen-binding fragment thereof, anti-V5 antibody or antigen-binding fragment thereof, maltose and halo.

In some embodiments, a capture agents can be conjugated to a solid surface or support that can be manipulated for recovery. For example, a capture agent can be coated on to magnetic beads for post cleavage recovery of released phage displaying a second affinity tag and a cleaved peptide. In a specific embodiment, M2 FLAG antibody coated protein G magnetic beads can be used to capture released phage displaying a FLAG tag (second affinity tag) and a cleaved peptide.

As used herein, the term "magnetic bead" means any solid support that is attracted by a magnetic field; such solid supports include, without limitation, DYNABEADS®, BIOMAG® Streptavidin, MPG7 Streptavidin, Streptavidin MAGNESPHERE™, Streptavidin Magnetic Particles, AFFINITIP™, any of the MAGA™ line of magnetizable particles, BIOMAG™ Superparamagnetic Particles, or any other magnetic bead to which a molecule (e.g., a capture agent the binds a first or second affinity tag) may be attached or immobilized.

A solid surface or solid support can comprise magnetic beads (e.g., micron-sized magnetic beads), Sepharose beads, agarose beads, a nitrocellulose membrane, a nylon membrane, a column chromatography matrix, a high performance liquid chromatography (HPLC) matrix or a fast performance liquid chromatography (FPLC) matrix.

VI. Methods for Peptide Detection

Following a step of capturing phage particles cleaved by a protease present in the sample, the DNA encoding the peptides can be subjected to an amplification step. In particular embodiments, the sample is subjected to conditions that will permit lysis of the phage (e.g., heat denaturation). In a specific embodiment, the nucleic acids from the lysed phage is subjected to an amplification reaction, such as a PCR reaction. In a more specific embodiment, the PCR reaction comprises a denaturation step that lyses the phage. In another embodiment, the nucleic acids encoding a phage-displayed peptide comprise a common adapter sequence for PCR amplification. In such embodiments, a PCR primer is designed to bind to the common adapter sequence for amplification of the DNA corresponding to a phage-displayed peptide.

In particular embodiments, the amplified DNA encoding the peptide can be detected by sequencing. In certain embodiments, a microarray hybridization approach can be used. In another embodiment, real time PCR amplification of specific DNA sequences can be used.

In certain embodiments, one of the PCR primers contains a common adaptor sequence which can be amplified in a second PCR reaction by another set of primers to prepare the DNA for high throughput sequencing. Unique barcoded oligonucleotides in the second PCR reaction can be used to amplify different samples and pool them together in one sequencing run to, for example, reduce cost and/or permit simultaneous detection of multiple phage-displayed peptides.

In some embodiments, the detection of a phage-displayed peptide comprises PCR with barcoded oligonucleotides. As used herein, the term "barcode" refers to a unique oligonucleotide sequence that allows a corresponding nucleic acid base and/or nucleic acid sequence to be identified. In certain aspects, the nucleic acid base and/or nucleic acid sequence is located at a specific position on a larger polynucleotide sequence (e.g., a polynucleotide covalently attached to a bead). In certain embodiments, barcodes can each have a length within a range of from about 4 to about 36 nucleotides, or from about 6 to about 30 nucleotides, or from about 8 to about 20 nucleotides. In certain aspects, the melting temperatures of barcodes within a set are within about 10° C. of one another, within about 5° C. of one another, or within about 2° C. of one another. In other aspects, barcodes are members of a minimally cross-hybridizing set. That is, the nucleotide sequence of each member of such a set is sufficiently different from that of every other member of the set that no member can form a stable duplex with the complement of any other member under stringent hybridization conditions. In one aspect, the nucleotide sequence of each member of a minimally cross-hybridizing set differs from those of every other member by at least two nucleotides. Barcode technologies are known in the art and are described in e.g., Winzeler et al., 285 SCIENCE 901 (1999); Brenner, C., 1(1) GENOME BIOL. 103.1-103.4 (2000); Kumar et al., 2 NATURE REV 302 (2001); Giaever et al., 101 PROC. NATL. ACAD SCI. USA 793 (2004); Eason et al., 101 PROC. NATL. ACAD. SCI. USA 1046 (2004); and Brenner, C., 5 GENOME BIOL. 240 (2004).

In some embodiments, a detectable label is used in the amplification reaction to permit detection of different amplification products. As used herein, "label" or "detectable label" refers to any atom or molecule which can be used to provide a detectable (in some embodiments, quantifiable) signal, and which can be operatively linked to a polynucleotide, such as a PCR primer or proxy DNA sequence (often referred to as a DNA barcode). Labels may provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. A primer of the present invention may be labeled so that the amplification reaction product may be "detected" by "detecting" the detectable label. "Qualitative or quantitative" detection refers to visual or automated assessments based upon the magnitude (strength) or number of signals generated by the label. A labeled polynucleotide (e.g., an oligonucleotide primer) according to the methods of the invention can be labeled at the 5' end, the 3' end, or both ends, or internally. The label can be "direct", e.g., a dye, or "indirect", e.g., biotin, digoxin, alkaline phosphatase (AP), horse radish peroxidase (HRP). For detection of "indirect labels" it is necessary to add additional components such as labeled antibodies, or enzyme substrates to visualize the captured, released, labeled polynucleotide fragment.

In specific embodiments, an oligonucleotide primer is labeled with a fluorescent label. Labels include, but are not limited to, light-emitting, light-scattering, and light-absorbing compounds which generate or quench a detectable fluorescent, chemiluminescent, or bioluminescent signal. See, e.g., Garman A., Non-Radioactive Labeling, Academic Press (1997) and Kricka, L., Nonisotopic DNA Probe Techniques, Academic Press, San Diego (1992). Fluorescent reporter dyes useful as labels include, but are not limited to, fluoresceins (see, e.g., U.S. Pat. Nos. 6,020,481; 6,008,379; and 5,188,934), rhodamines (see, e.g., U.S. Pat. No. 6,191,278; 6,051,719; 5,936,087; 5,847,162; and 5,366,860), benzophenoxazines (see, e.g., U.S. Pat. No. 6,140,500), energy-transfer fluorescent dyes, comprising pairs of donors and acceptors (see, e.g., U.S. Pat. Nos. 5,945,526; 5,863,727; and 5,800,996; and), and cyanines (see, e.g., WO 9745539), lissamine, phycoerythrin, Cy2, Cy3, Cy3.5, Cy5, Cy5.5, Cy7, FluorX (Amersham Biosciences, Inc. (Piscataway, NJ)), Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, Tetramethylrhodamine, and/or Texas Red, as well as any other fluorescent moiety capable of generating a detectable signal. Examples of fluorescein dyes include, but are not limited to, 6-carboxyfluorescein; 2',4',1,4,-tetrachlorofluorescein, and 2',4',5',7',1,4-hexachlorofluorescein. In certain aspects, the fluorescent label is selected from SYBR-Green, 6-carboxyfluorescein ("FAM"), TET, ROX, VICTM, and JOE. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In further embodiments, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g., Blackburn et al., eds. "DNA and RNA Structure" in Nucleic Acids in Chemistry and Biology (1996)).

In certain embodiments, the detection of a phage-displayed peptide comprises high throughput detection of a plurality of peptides simultaneously, or near simultaneously.

In some embodiments, the high-throughput systems use methods similar to DNA sequencing techniques. Any conventional DNA sequencing technique may be used.

A number of DNA sequencing techniques are known in the art, including fluorescence-based sequencing methodologies (See, e.g., Birren et al., Genome Analysis: Analyzing DNA, 1, Cold Spring Harbor, N.Y.). In some embodiments, automated sequencing techniques understood in the art are utilized. In some embodiments, the high-throughput systems described herein use methods that provide parallel sequencing of partitioned amplicons (e.g., WO2006084132). In some embodiments, DNA sequencing is achieved by parallel oligonucleotide extension (See, e.g., U.S. Pat. Nos. 5,750, 341, and 6,306,597). Additional examples of sequencing techniques include the Church polony technology (Mitra et al., 320 ANAL. BIOCHEM. 55-65 (2003); Shendure et al., 309 SCIENCE 1728-32 (2005); U.S. Pat. Nos. 6,432,360; 6,485, 944; 6,511,803), the 454 picotiter pyrosequencmg technology (Margulies et al., 437 NATURE 376-80 (2005); US20050130173), the Solexa single base addition technology (Bennett et al., 6 PHARMACOGENOMICS 373-82 (2005); U.S. Pat. Nos. 6,787,308; 6,833,246), the Lynx massively parallel signature sequencing technology (Brenner et al., 18 NAT. BIOTECHNOL. 630-34 (2000); U.S. Pat. Nos. 5,695,934; 5,714, 330), and the Adessi PCR colony technology (Adessi et al., 28 NUCLEIC ACID RES. E87 (2000); WO00018957).

Next-generation sequencing (NGS) methods share the common feature of massively parallel, high-throughput strategies, with the goal of lower costs in comparison to older sequencing methods (see, e.g., Voelkerding et al., 55 CLINICAL CHEM. 641-58 (2009); MacLean et al., 7(4) NAT. REV. MICROBIOL. 287-96 (2009)). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by ILLUMINA™, and the Supported Oligonucleotide Ligation and Detection™ (SOLiD) platform commercialized by APPLIED BIOSYSTEMS™. Non-amplification approaches, also known as single-molecule sequencing, are exemplified by the HELISCOPE™ platform commercialized by HELICOS BIOSYSTEMS™, and emerging platforms commercialized by VISIGEN™, OXFORD NANOPORE TECHNOLOGIES LTD., and PACIFIC BI OSCIENCES™, respectively.

In pyrosequencing (Voelkerding et al. (2009)); MacLean et al, Nature Rev. Microbial., 7:287-296; U.S. Pat. Nos. 6,210,891; 6,258,568), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, resulting in up to 500 million base pairs (Mb) of sequence.

In certain embodiments, nanopore sequencing is employed (see, e.g., Astier et al., 128(5) J. AM. CHEM. SOC. 1705-10 (2006)). The theory behind nanopore sequencing has to do with what occurs when a nanopore is immersed in a conducting fluid and a potential (voltage) is applied across it. Under these conditions, a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HELISCOPE™ by HELICOS BIOSCIENCES™ is employed (Voelkerding et al. (2009); MacLean et al. (2009); U.S. Pat. Nos. 7,169,560; 7,282,337; 7,482,120; 7,501,245: 6,818,395; 6,911,345: 7,501,245). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from about 25-50 nucleotides with overall output exceeding 1 billion nucleotide pairs per analytical run.

The Ion Torrent technology is a method of DNA sequencing based on the detection of hydrogen ions that are released during the polymerization of DNA (see, e.g., 327(5970) SCIENCE 1190 (2010); U.S. Patent Appl. Pub. Nos. 20090026082, 20090127589, 20100301398, 20100197507, 20100188073, and 20100137143). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is about 99.6% for 50 base reads, with –100 Mb generated per run. The read-length is 100 base pairs. The accuracy for homopolymer repeats of 5 repeats in length is about 98%.

Another example of a nucleic acid sequencing approach that can be adapted for use with the methods described herein was developed by STRATOS GENOMICS, Inc. and involves the use of XPANDOMERS™. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an XPANDOMER™ of a length longer than the plurality of the subunits of the daughter strand. The XPAN- DOMER™ typically includes the tethers and reporter elements for parsing genetic information in a sequence corresponding to the contiguous nucleotide sequence of all or a portion of the target nucleic acid. Reporter elements of the XPANDOMER™ are then detected. Additional details relating to XPANDOMER™-based approaches are described in, for example, U.S. Pat. Pub No. 20090035777, entitled "HIGH THROUGHPUT NUCLEIC ACID SEQUENCING BY EXPANSION," filed Jun. 19, 2008, which is incorporated herein in its entirety.

Other single molecule sequencing methods include real-time sequencing by synthesis using a VISIGEN™ platform (Voelkerding et al. (2009); U.S. Pat. Nos. 7,329,492: 7,668, 697; WO2009014614) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by PACIFIC BIOSCIENCES™ (Voelkerding et al. (2009); MacLean et al. (2009); U.S. Pat. Nos. 7,170,050; 7,302,146; 7,313,308; 7,476,503) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that can be adapted for use with the methods described herein include, for example, but are not limited to U.S. Pat. Nos. 7,405,281, 7,315,019, 7,313,308, 7,302,146, 7,170,050, U.S. Pat, Pub. Nos. 20080212960, 20080206764, 20080199932, 20080176769, 20080176316, 20080176241, 20080165346, 20080160531, 20080157005, 20080153100, 20080153095, 20080152281, 20080152280, 20080145278, 20080128627, 20080108082, 20080095488, 20080080059, 20080050747, 20080032301, 20080030628, 20080009007, 20070238679, 20070231804, 20070206187, 20070196846, 20070188750, 20070161017, 20070141598, 20070134128, 20070128133, 20070077564, 20070072196, 20070036511, and Koriach et al., 105(4) PROC. NATL. ACAD. SCI. USA 1176-81 (2008), all of which are herein incorporated by reference in their entireties.

VII. Sequence Analysis

Subsequently, in some embodiments, the data produced from the assay comprises sequence data from multiple barcoded DNAs. Using the known association between the barcode and the source of the DNA, the data can be deconvoluted to assign sequences to the source subjects, samples, organisms, etc.

Some embodiments include a processor, data storage, data transfer, and software comprising instructions to assign genotypes. Some embodiments of the technology provided herein further comprise functionalities for collecting, storing, and/or analyzing data. For example, some embodiments comprise the use of a processor, a memory, and/or a database for, e.g., storing and executing instructions, analyzing data, performing calculations using the data, transforming the data, and storing the data. In some embodiments, the processor is configured to calculate a function of data derived from the sequences and/or genotypes determined. In some embodiments, the processor performs instructions in software configured for medical or clinical results reporting and in some embodiments the processor performs instructions in software to support non-clinical results reporting. In some embodiments, there is a non-tangible computer-readable product that contains instructions to cause a computing device to perform any of the methods described herein.

VIII. Other Specific Embodiments of the Present Invention

One embodiment of the present invention is a vector encoding a displayed peptide molecule comprising a first flanking peptide that attaches to a solid surface, a second middle peptide used to detect protease activity in a sample, and a third flanking peptide for post-cleavage recovery. The second peptide may be positioned C-terminal of the first flanking peptide and N-terminal to the third flanking peptide, or the second peptide may be positioned N-terminal of the first flanking peptide and C-terminal to the third flanking peptide. The third peptide is used to recover a nucleic acid sequence that identifies the second peptide sequence. An example of a suitable second peptide is a peptide from a peptidome. An example of a suitable peptidome is a human peptidome. An example of a first flanking peptide is a biotinylation sequence or a functional portion thereof. An example of a third flanking peptide is an epitope tag sequence or a functional portion thereof.

Another embodiment of the present invention is a bacteriophage comprising any one of the vectors described in herein. In some embodiments, a bacteriophage of the present invention comprises a vector that expresses a single copy of the peptide molecule on the surface of the bacteriophage.

Another embodiment of the present invention is a method of protease activity profiling. The method comprises the following steps of providing a bacteriophage library comprising members displaying a peptide molecule comprising a first flanking peptide that attaches to a solid surface, a second middle peptide used to detect protease activity in a sample, and a third flanking peptide for post-cleavage recovery of a nucleic acid sequence identifier. Combining the bacteriophage library with a first solid surface so that the first flanking peptide is able to attach to the first solid surface forming an immobilized bacteriophage library. Combining a sample thought to contain one or more proteases with the attached bacteriophage library. Allowing cleavage of the second peptide so that one part of the second peptide remains attached to the first solid surface and a second part of the second peptide is released into solution along with the third flanking peptide sequence and the bacteriophage particle forming released particles. Combining the released particles displaying the second part of the second peptide and the third flanking peptide with a second solid surface capable of binding the third flanking peptide forming a population of immobilized bacteriophage particles enriched for sequences encoding peptides that were cleaved during the assay. Methods of the present invention may further comprise the step of amplifying DNA encoding the second part of the second peptide from the immobilized bacteriophage particles forming amplified DNA. Methods of the present invention may further comprise the step of sequencing the amplified DNA. In addition, the DNA encoding the second part of the second peptide may comprise a DNA sequence proxy. If a DNA sequence proxy is present, then the methods of the present invention may further comprise a step of amplifying the DNA sequence proxy of a second part of a second peptide from the immobilized bacteriophage particles forming amplified DNA. An example of a DNA sequence proxy used in the present invention is a barcode. The methods of the present invention may further comprise the step of sequencing the amplified DNA.

Another embodiment of the present invention is a kit comprising one or more aliquots of a composition of the present invention selected from a group consisting of the vector of claim 1, a phage display bacteriophage library comprising the vector of claim 1, or a combination thereof.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Protease Activity Profiling Via Programmable Phage Display of Comprehensive Proteome-Scale Peptide Libraries Materials and Methods Materials.
All materials not described below were purchased from commercial suppliers and were of the highest grade available. Caspase-1, ADAM17, Thrombin, and PreScission proteases were purchased from BioVision, RnD Systems, SignalChem, and GE Life Sciences respectively.

Construction of T7 SEPARATE Phage Vector.
The SEPARATE vector (T7-SEPARATE) was constructed by cloning a custom-designed gBlock gene fragment (IDT) into the BamHI/SalI site of the low-copy T7Select1-2b phage vector (Millipore). The gBlock fragment is based on a 90-amino acid β-lactoglobulin peptide sequence containing two PreScission protease cleavage sites (LEVLFQGP) (SEQ ID NO:1).[42] C-terminal to the peptide is a V5 tag, followed by a TEV cleavage sequence, and then an AviTag[43] biotinylation sequence (GLNDIFEAQK-IEWHE) (SEQ ID NO:2), which is enzymatically conjugated with a single biotin moiety in vivo during phage replication in E. coli. N-terminal to the displayed peptide is a 3×-FLAG tag followed by an enterokinase cleavage site. Restriction sites EcoRI/XhoI were placed upstream and downstream of the engineered β-lactoglobulin peptide to allow for library subcloning into the T7-SEPARATE vector.

Subcloning the Human Peptidome Library into the T7-SEPARATE Vector.
T7-Pep2,[44] a complete human proteome library was restriction cloned into the T7-SEPARATE vector using the EcoRI/XhoI sites.[44,45] The library was packaged in vitro using the T7Select Packaging Kit (Millipore Sigma) and expanded by plate lysate amplification to obtain an average clonal representation of ~100 plaques per peptide. To select for AviTag-displaying peptides, the initial expansion of this library was immobilized on streptavidin beads, washed to remove unbound phage particles (to remove prematurely truncated or out-of-frame peptides which will lack the downstream AviTag), digested with enterokinase, and re-expanded by plate lysate amplification at >100-times representation per peptide. Bacterial debris and large particulates were removed by centrifugation, followed by filtration through a 0.22 μm PES membrane, and the clarified library pool was stored at −80° C. in 10% DMSO. The quality of the library peptides was assessed by Sanger sequencing of individual plaques from the packaging expansion and the clonal distribution assessed by Illumina sequencing.

SEPARATE Assay: Immobilization of the T7-SEPARATE Library.
Streptavidin-coupled magnetic beads (Dynabeads M-280 Streptavidin, ThermoFisher Scientific) were washed (TBS, pH 7.4, 0.01% NP40) and resuspended in binding buffer (TBS, pH 7.4, 0.001% NP40) containing 2E9 plaque forming units per 10 μl of bead slurry. End-over-end mixing at room temperature was performed for one hour. Phage-coated beads were washed three times with wash buffer and transferred into two protein LoBind Eppendorf tubes blocked with TBS, pH 7.4 containing 1% BSA.

SEPARATE Assay: Protease Digestion.
Protease digestions was performed in 50 μl of appropriate buffer alone or containing the protease: (a) Caspase-1/PreScission: 1×TBS, pH 7.4, 0.01% NP40, 1 mM DTT; (b) Thrombin: TBS, pH 7.4, 0.01% NP40; (c) ADAM17: Tris, pH 8.0, ZnCl2 2.5 uM, 0.005% Tween 20. Digestion occurred overnight at room temperature with end-over-end rotation. Digest reactions were quenched by addition of 100 μl TBS, pH 7.4, 0.01% NP40 containing AEBSF (2 mM), Aprotinin (0.3 μM), Bestatin (116 μM), E-64 (14 μM), Leupeptin (1 μM), and EDTA (1 mM) for thirty minutes at room temperature. To remove any residual biotinylated phage that may have been nonspecifically released, the 150

µl supernatant of the quenched digest reaction is then incubated with a fresh 10 µl of slurry volume M280 streptavidin beads (pre-washed three times with wash buffer) in a LoBind Eppendorf tube blocked with TBS, pH 7.4 containing 1% BSA at room temperature for one hour with end-over-end rotation.

SEPARATE Assay: Recapture of Cleaved Phage Clones.

10 µl slurry volume of protein G magnetic dynabeads were washed in buffer (TBS, pH 7.4, 0.01% NP40) and then resuspended in 50 µl TBS, pH 7.4, 0.01% NP40 containing 4 µg of M2 FLAG antibody for thirty minutes at room temperature with end-over-end rotation. The 150 µl quenched digest reaction is added to the 10 µl FLAG-coated Protein G beads and incubated for 60 minutes at room temperature with end-over-end rotation to capture phage particles released at the protease digest step. Beads are rinsed once with 100 µl wash buffer and stored at −80° C. until PCR amplification.

SEPARATE Assay: Amplification and Sequencing of Recaptured Phage Clones.

Library PCR preparation, high-throughput DNA sequencing, and peptide read count data generation was performed as described previously.[44] Briefly, library peptide inserts are amplified by resuspending 10 µl of FLAG-coated Protein G beads in PCR1 master mix containing the T7-Pep2_PCR1_F forward primer (ATAAAGGTGAGGGTAATGTC) (SEQ ID NO:3) and a T7-SEPARATE vector specific reverse primer (CTGGAGTTCAGACGTGTGCTCTTCCGATCAACCCCTCAAGACCCGTTTA) (SEQ ID NO:4), which includes an adapter sequence for sample-specific barcoding and Illumina P7 adapter incorporation during a subsequent PCR2 reaction. The PCR2 amplicons are pooled and sequenced using an Illumina NextSeq instrument in standard output mode to obtain single-end 50 nucleotide reads. Dual indexed sample demultiplexing and clonal read count determination were performed using exact sequence matching. Read counts were normalized using a 'random peptide normalization' method, which attempts to make data comparable between samples by calculating a normalization factor based on 'background' recaptured phage clones. To calculate the normalization factor, 100 peptides were randomly selected from the mock digest conditions with a read count ranging between 10 and 40. The median read count value for these 100 peptides is calculated for each sample. The random peptide selection and median calculation is performed 20 times and the average of the 20 median values is calculated for each sample. Finally, the normalization factor is calculated by dividing the average median value for each sample by that for one of the mock digest conditions. Read counts are then converted to normalized read counts by dividing each sample's read count values by the normalization factor. Fold enrichments are calculated for each peptide by dividing their normalized read counts in the digest condition by the normalized read counts in the mock digest condition. The fold enrichments can be visualized in an MA plot by transforming the normalized read count data into a log ratio (M, on the y-axis) and a mean average (A, on the x-axis) between the digest and mock digest conditions.

THP1 Cell Culture.

THP-1 cells were cultured in RPMI-1640 media with Glutamax (Gibco, ThermoFisher, Cat #61870127), supplemented with 10% FBS (Hyclone SH30071, GE Life Sciences), and 1× Antibiotic-Antimycotic (Gibco, ThermoFisher, Cat #15240062), referred to as complete RPMI. To differentiate THP-1 cells into macrophages, $1\times10^6$ THP-1 cells were added per well of a 6-well plate in complete RPMI medium containing 50 ng/ml Phorbol 12-myristate 13-acetate (PMA, diluted in RPMI medium from a 1 mg/ml PMA stock in DMSO, Millipore Sigma, Cat. No. P1585). After 48 hours when the cells become adherent, the medium with PMA was removed, cells washed in 1×PBS once, and fresh complete RPMI was added. Cells were allowed to rest for an additional 24 hours before inflammasome activation with LPS and Nigericin.

In Vitro Stimulation of the Inflammasome in THP-1 Cells.

A 6-well plate of PMA differentiated THP-1 cells were treated with 0, 1 or 0.1 µg/ml LPS (Millipore Sigma, Cat. No. LPS25) for 3.5 hours. After 3.5 hours, cells were treated with 2.5 µM Nigericin for an additional 30 minutes to activate the inflammasome. Cells were washed in 1×PBS and lysed in 1× mammalian cell extraction buffer (BioVision, Cat. No. K269) containing 2 µM Dithiothreitol (DTT). Nuclei were spun down by centrifugation (10,000 rpm, 5 minutes, 4° C.) and the cleared supernatant was used to perform Western blots.

HUWE1 Cleavage Assay Using Recombinant Caspase-1.

Recombinant Caspase-1 (rCaspase-1) was diluted to 0.1 U/µl in 1× mammalian cell extraction buffer containing 2 µM Dithiothreitol (DTT). This buffer preserves enzymatic activity of proteases. Unstimulated, PMA differentiated THP-1 cells were also lysed in 1× mammalian cell extraction buffer with 200 µl of buffer to lyse one well of a 6-well plate ($\sim 1\times10^6$ cells). Protease digests were set up with 50 µl of lysate ($\sim 250,000$ cells).

Western Blot Analysis.

30 µl of protein lysates were mixed with 10 µl of 4× NuPage LDS sample loading buffer (Thermo Fisher, Cat. No. NP0007, final concentration to 1×). 4-12% NuPage Bis-Tris gels (Thermo Fisher, Cat. No. NP0321) were loaded with 35 µl of each sample along with high molecular weight standards (HiMark protein ladder, Thermo Fisher, Cat. No. LC5699) and resolved in 1× NuPAGE™ MES SDS Running Buffer (Thermo Fisher, Cat. No. NP0002) at 150V for 50-60 minutes. After suitable resolution of proteins, the gels were transferred to a PVDF membrane by the 'wet transfer' method using 1× NuPage transfer buffer (Thermo Fisher, Cat. No. NP00061) overnight at 4° C., 50 mA constant current. After transfer is complete, the membranes were washed in 1× tris buffered saline containing 0.01% Tween-20 (TBS-T), blocked for 30 minutes with 5% milk in TBS-T and probed with primary antibodies and HRP conjugated secondary antibodies with TBS-T washing in between. After probing with secondary antibody, the membranes were washed 3 times, 5 minutes each with TBS-T, treated with Pierce ECL Plus Western Blotting Substrate (Thermo Fisher, Cat. No. 32132) for 5 minutes and exposed to Hyperfilm ECL (Millipore Sigma, Cat. No. GE28-9068-38). Anti-HUWE1 antibody (Thermo Fisher, Cat. No. A300-486A) was diluted 1:1000 in 5% milk and used to probe membranes overnight at 4° C. Anti-GSDMD antibody (Thermo Fisher, Cat. No. 20770-1-AP) was diluted 1:1,000 in 5% milk and used to probe membranes 2-4 hours at room temperature before the addition of secondary antibody. Secondary antibody (antirabbit IgG, Cell Signaling, Cat. No. 7074S) was diluted to 1:5,000 in 5% milk and probed 2 hours at room temperature.

Results and Discussion

Proteases catalyze the irreversible hydrolysis of peptide bonds with consequences that include target destruction, protein maturation, and signal transduction. These enzymes participate in diverse biological functions, including tissue remodeling and morphogenesis, infection, blood coagulation, neoplasia, and cancer metastasis.[1-4] Their enzymatic activities can therefore serve both as valuable diagnostic biomarkers and as therapeutic targets.[5-9] There are 1,252 putative human proteases belonging to five families, accounting for ~3.5% of the human proteome.[10] Given their importance and diversity, there is an unmet need for unbiased techniques to profile the activity of proteases, both in isolation and as components of complex biological mixtures. The physiological substrates of only a small fraction of proteases have been characterized in some detail; even for these enzymes, their full complement of substrates remains unknown.

Currently, unbiased protease profiling approaches are based on mass spectrometry[11,12] and tend to be both cumbersome and expensive. Targeted activity-based profiling techniques[13,14] can detect active proteases, but are typically limited by lower levels of assay multiplexing and are restricted to enzymes with well characterized substrates.[15,16] Attempts to characterize cleavage motifs have also utilized the bacteriophage display of random peptide libraries[17-19], but these types of analyses are typically difficult to interpret as they primarily focus on identifying consensus motifs which are then mapped by sequence alignment onto candidate protein substrates. This approach may be useful in identifying some substrates, but will fail to identify substrates. Consensus motifs identified using random libraries may not match well with true protein sequences.

Figure 1B:
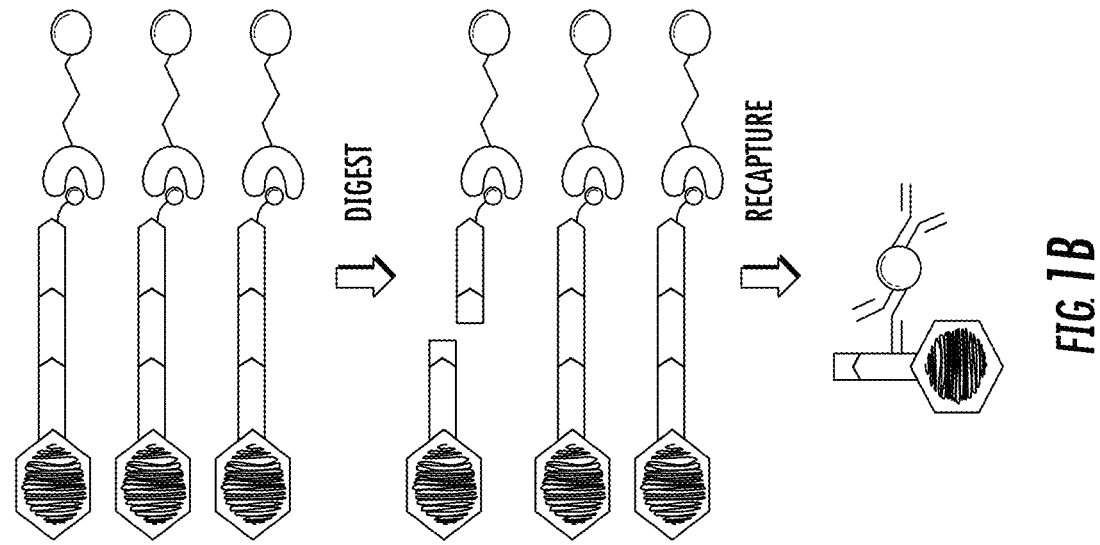
Figure 1A:
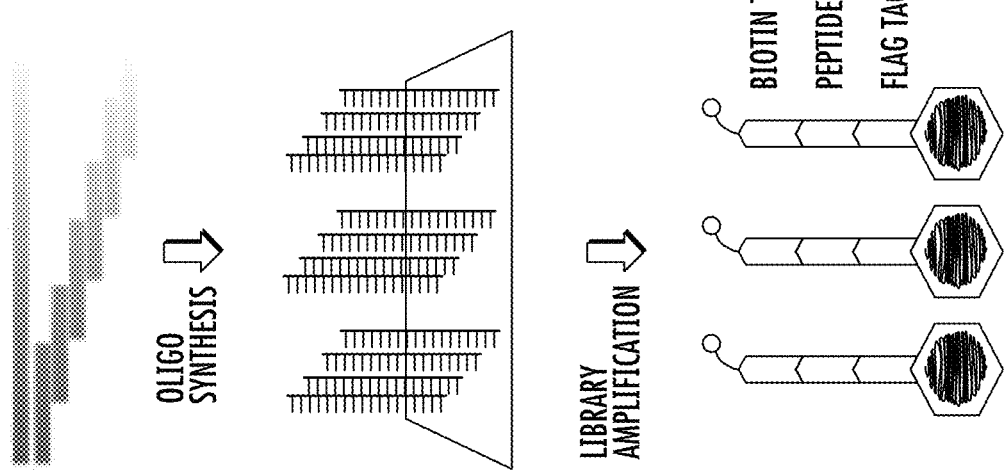

The present invention describes SEPARATE (Sensing EndoPeptidase Activity via Release and recapture using flAnking Tag Epitopes), a highly multiplexed protease profiling platform that combines a complete human proteome library cloned into a novel T7 phage display vector and quantitative analysis via next generation DNA sequencing (NGS). SEPARATE enables unbiased, low-cost, and high sample throughput characterization of human protease activities, thereby overcoming key limitations of current approaches. ~250,000 oligonucleotides encoding 90 amino acid overlapping human peptide tiles, with 45 amino acid overlaps, covering the entire reference human proteome[20], were synthesized and cloned as a pool into the T7-SEPARATE phage display vector (FIG. 1A). This vector displays a library peptide as a C-terminal fusion to the 10B T7 capsid protein, a distally flanking (C-terminal) biotinylated AviTag for library immobilization and a proximally flanking (N-terminal) 3× FLAG tag for recapture of released phage particles (FIG. 1B). The DNA sequences corresponding to the displayed peptides in the recaptured phage particles can then be amplified by PCR and quantified using NGS (FIG. 1C). SEPARATE detects proteolysis-dependent enrichments of each peptide in the recaptured library and is amenable to cost-reduction via sample multiplexing using barcodes introduced during PCR amplification.

Figure 1D:
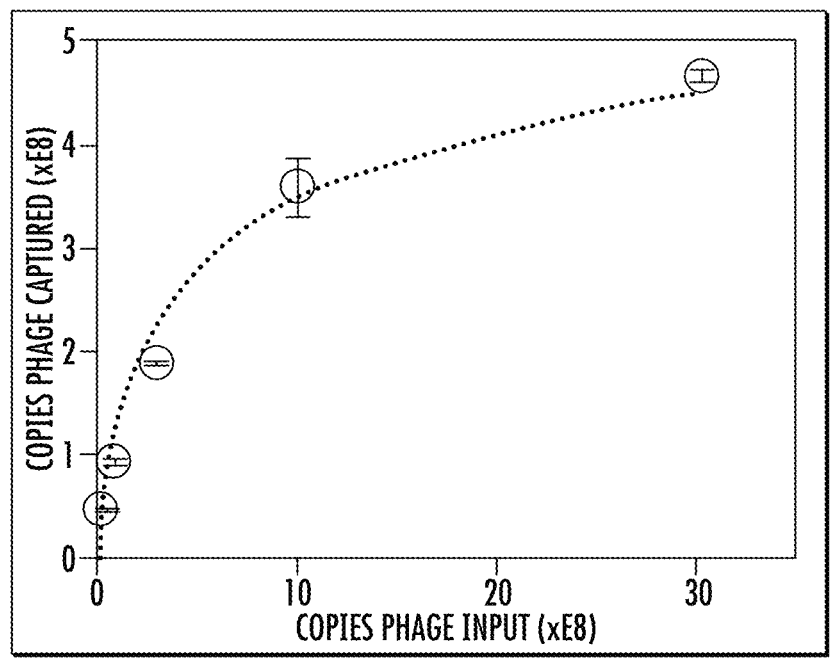

Irreversible library pre-immobilization has several advantages, including concentration of the library into small assay volumes, flexible buffer exchange for protease compatibility, and the removal of defective phage clones displaying peptides with frameshift or non-sense mutations. The C-terminal biotinylated AviTag provides near irreversible immobilization to streptavidin coated magnetic beads, which minimizes the amount of non-specific phage particle release and thus the background noise of the assay, even during lengthy digest reactions. Initial experiments revealed that the AviTag is sufficiently biotinylated during phage replication in *E. coli* cells, even without overexpression of a biotin ligase. A titration experiment was performed to estimate the fraction of biotinylated phage particles captured on streptavidin beads. When 109 phage particles are mixed with 10 µl of beads, ~3×10$^8$ particles (30%) remain bound ensuring that each peptide of the 250,000 member human proteome library is represented greater than 1,000 times on average at the start of a digest reaction (FIG. 1D). Pre-blocking the streptavidin-coated beads with free biotin confirmed that ~99% of the bound phage are indeed immobilized via their C-terminal biotin tag (data not shown). Recapture of released phage particles via a proximal 3× FLAG tag reduces background noise from phage detached by physical dissociation of the displayed peptide, concentrates the recaptured phage into a small volume for PCR, while also removing potential PCR inhibitors present in the digest reaction.

Figure 1E:
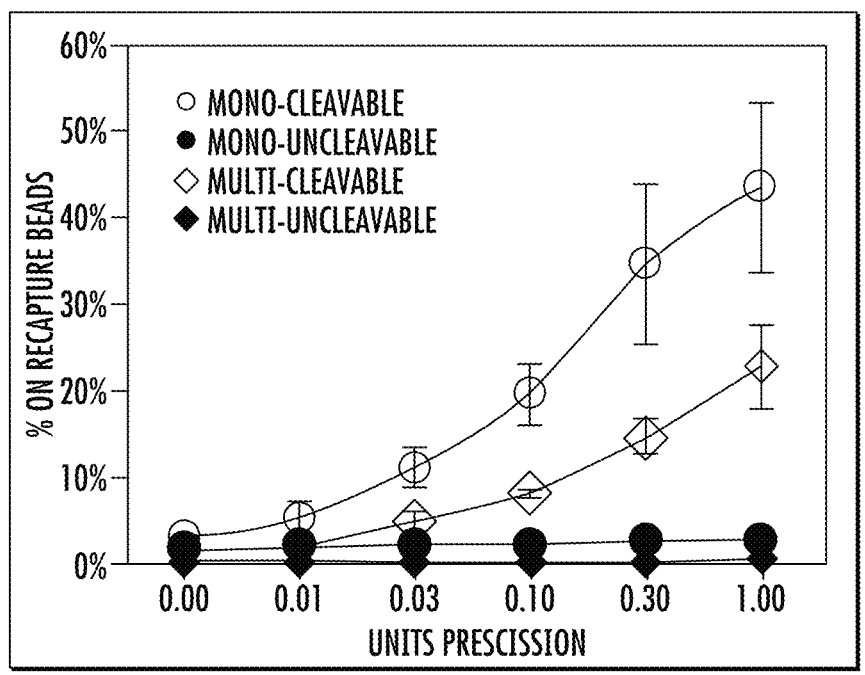
Figure 4:
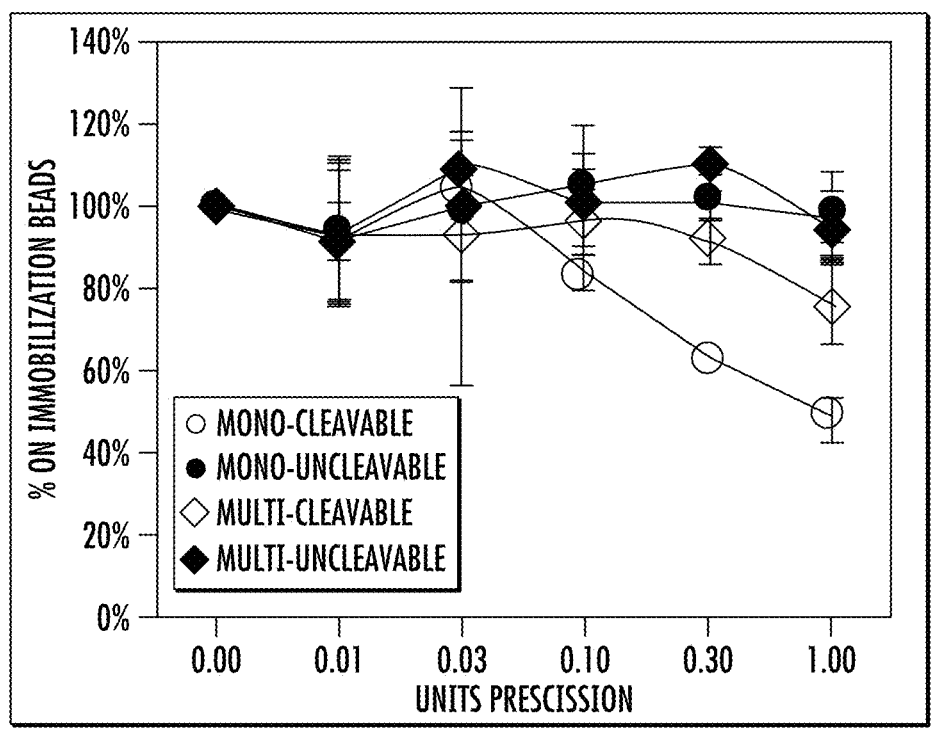
FIG. 4. A monovalent display format outperforms a multivalent display in SEPARATE. A T7-SEPARATE clone encoding the PreScission cleavage motif -LGVLPG/GP- (SEQ ID NO:1) was prepared using both the T7Select1-2b monovalent (○) and the T7Select10-3b multivalent (◇) T7 display vectors. The monovalent display results in a higher depletion of phage clones from the immobilization beads indicating a higher fraction is digested at a given concentration of PreScission protease. A negative control clone lacking the PreScission cleavage motif is not digested off of streptavidin-coated for both monovalent (●) and multivalent (◆) display vectors.

The present inventors reasoned that monovalent peptide display would enhance detection sensitivity by requiring just a single protease cleavage event to release a target phage particle. To test this hypothesis, positive and negative controls were constructed, which could be monitored via quantitative real-time PCR. A cleavable 90-aa substrate for the commercially available PreScission enzyme (human rhinovirus 3C protease, GE Life Sciences, MA) served as a positive control, whereas a randomly selected 90-aa human peptide from the proteome library served as an uncleavable negative control. Both controls were also subcloned into a mid-copy (multivalent) version of the T7-SEPARATE vector, which displays 10B-fused peptides at a copy number between 5 and 15 per phage particle. At all concentrations of PreScission tested, the monovalent display format provided a substantial increase in the number of phage particles released and recaptured (up to 53% and 43%, respectively, of the total number of pre-immobilized phage particles), in comparison to the same conditions but using the multivalent display format (up to 24% and 22.5%, respectively; FIG. 1E and FIG. 4). When PreScission enzyme was omitted from the reaction (a 'mock' digest, corresponding to 0 units PreScission enzyme in the dilution series), only ~1% of the immobilized cleavable phage was detected on the recapture beads. In parallel, we measured the recapture of the uncleavable peptide, in which case ~1% of the immobilized phage particles were similarly recaptured, whether the PreScission enzyme was included in the digest reaction or not. Non-targeted peptides are therefore expected to contribute uniformly to the low background, both in the presence and absence of a test protease. Comparing the proportions of control peptide-displaying clones for the highest PreScission concentration versus the mock digest, the monovalent T7-SEPARATE format was found to perform at a signal-to-noise ratio of 23.4 versus 11.86 for the multivalent format.

Figure 5B:
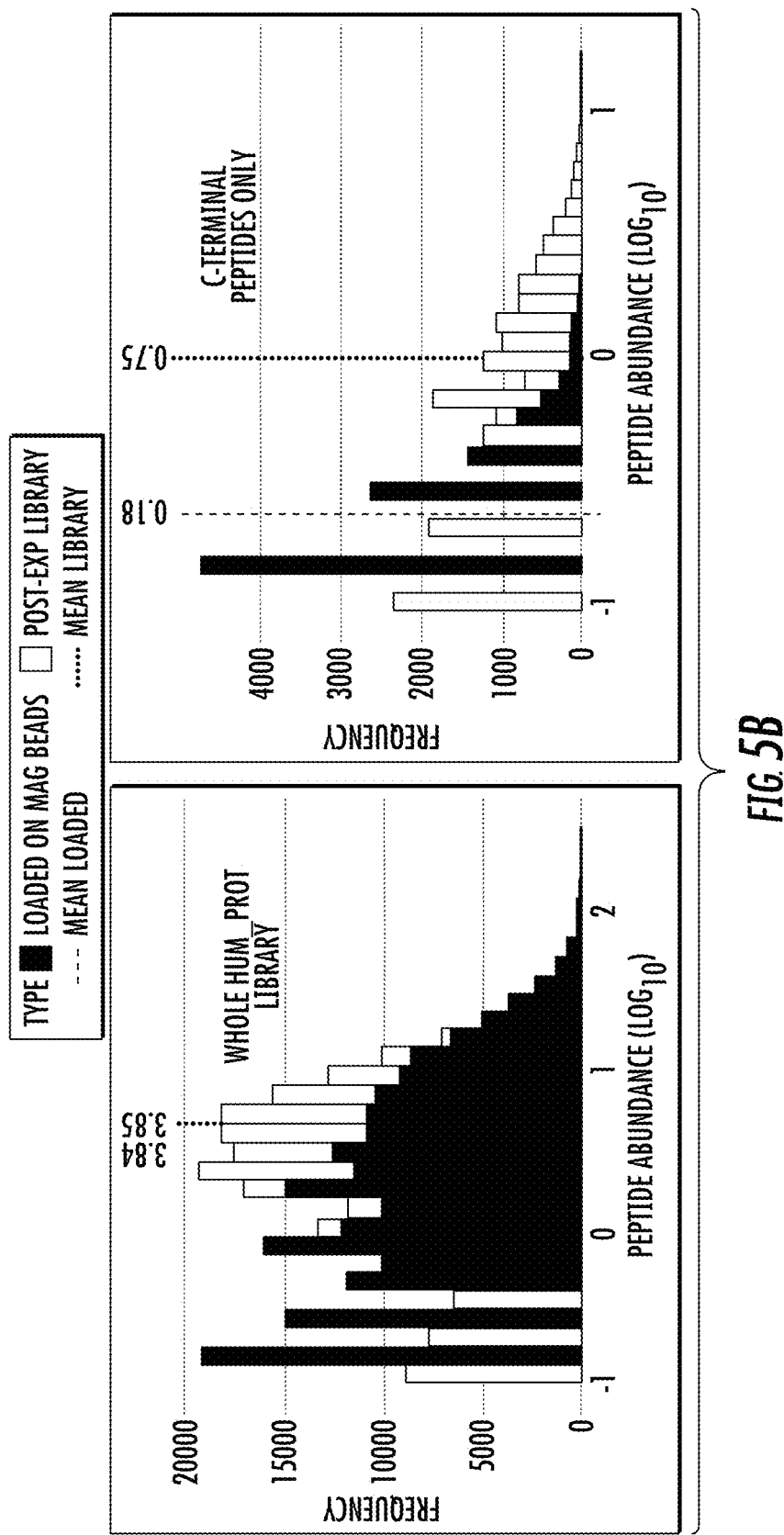

The human peptidome library was cloned into the T7-SEPARATE vector as described in the methods section. To enrich for full length peptides, the pre-expansion library was first immobilized on streptavidin conjugated beads, washed to remove unbound phage particles, released the bound phage using enterokinase and expanded them to obtain the post-expansion library (FIG. 5A). All subsequent assays were performed with the post-expansion library. We sequenced the post-expansion and immobilized library at >40× and >27× coverage, respectively (Table 1). The representation of peptides after immobilization was comparable to the input post-expansion library (FIG. 5B, left panel). About 87% and 79% of all the peptides in the human peptidome were represented in the post-expansion library and the immobilized library, respectively (Table 1). When the human proteome library was initially constructed, C-terminal peptides were designed to include their native stop codons, with the result that these sequences are depleted >5-fold in the post-expansion library due to their lack of AviTags. After immobilizing the library on streptavidin-coated beads, C-terminal peptides are depleted another 4-fold, (>20-fold depletion versus the pre-expansion library; FIG. 5B, right panel). The human proteome library was designed to represent 29,708 protein sequences. Of these, only 262 and 706 proteins were completely absent from the T7-SEPARATE postexpansion and streptavidin bead loaded libraries, respectively. The missing proteins tended to be smaller (~100 amino acids versus ~580 amino acids for the represented proteins) suggesting that non-C-terminal peptide dropout is likely stochastic.

Figure 1F:
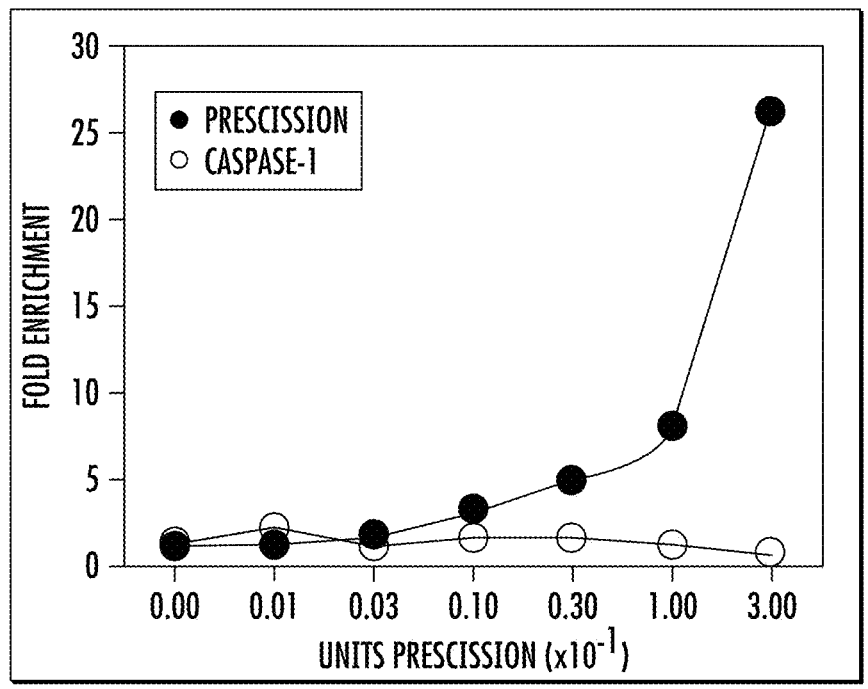
Figure 1G:
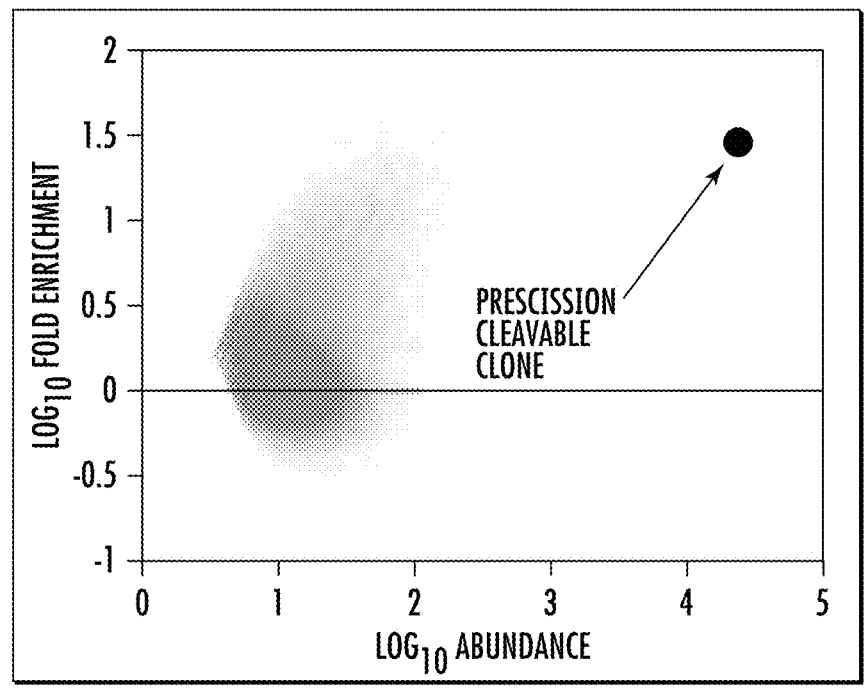
Figure 6C:
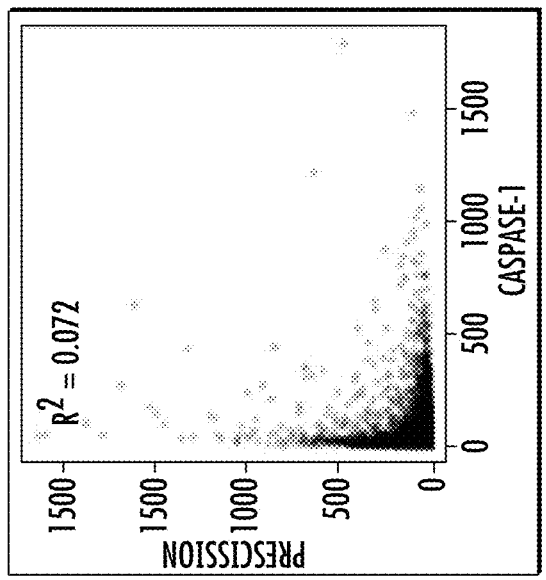
FIG. 6A-6C. SEPARATE produces low background and is reproducible.
Figure 6B:
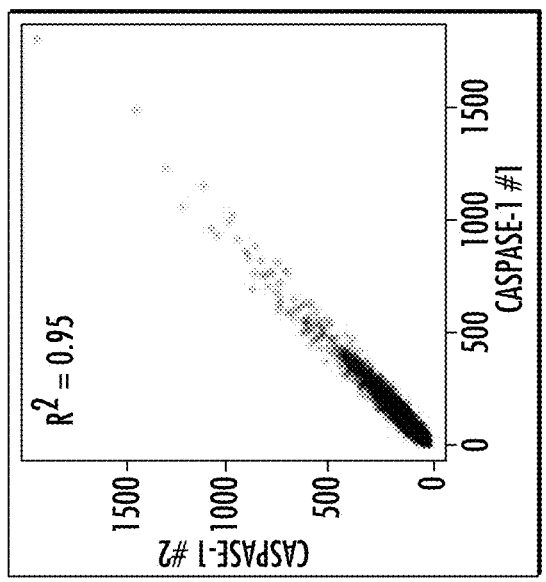
Figure 6A:
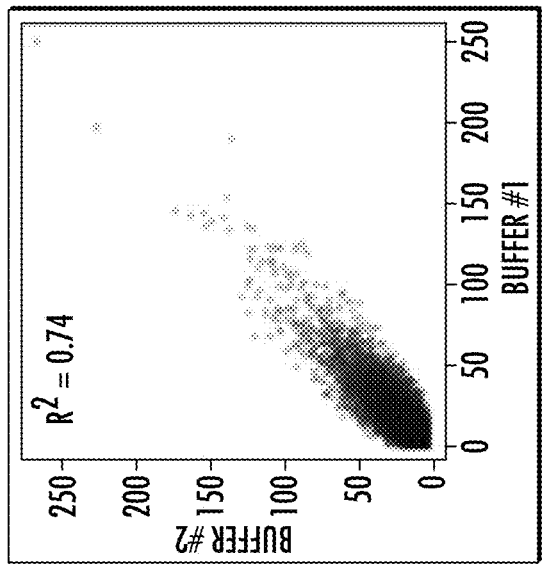

To assess the performance of a proteomic-scale SEPARATE assay, the PreScission-cleavable clone was spiked into the complete human library at a ratio of 1 to 100. Recapture of the cleavable peptide demonstrated a protease concentration-dependent efficiency, with the highest concentration resulting in a 26-fold increase versus a mock digest or digest with Caspase-1 (FIG. 1F). Technical duplicate enzymatic digests and mock digests are shown in FIG. 6, which illustrate the assay reproducibility and discordance between digests with distinct enzymes. FIG. 1G shows that, as expected, the PreScission-cleavable peptide is indeed the most abundant clone on the anti-FLAG recapture beads and is also the most differentially enriched clone. Interestingly, a number of statistically significant candidate PreScission substrates were also identified in this experiment.

Figure 2A:
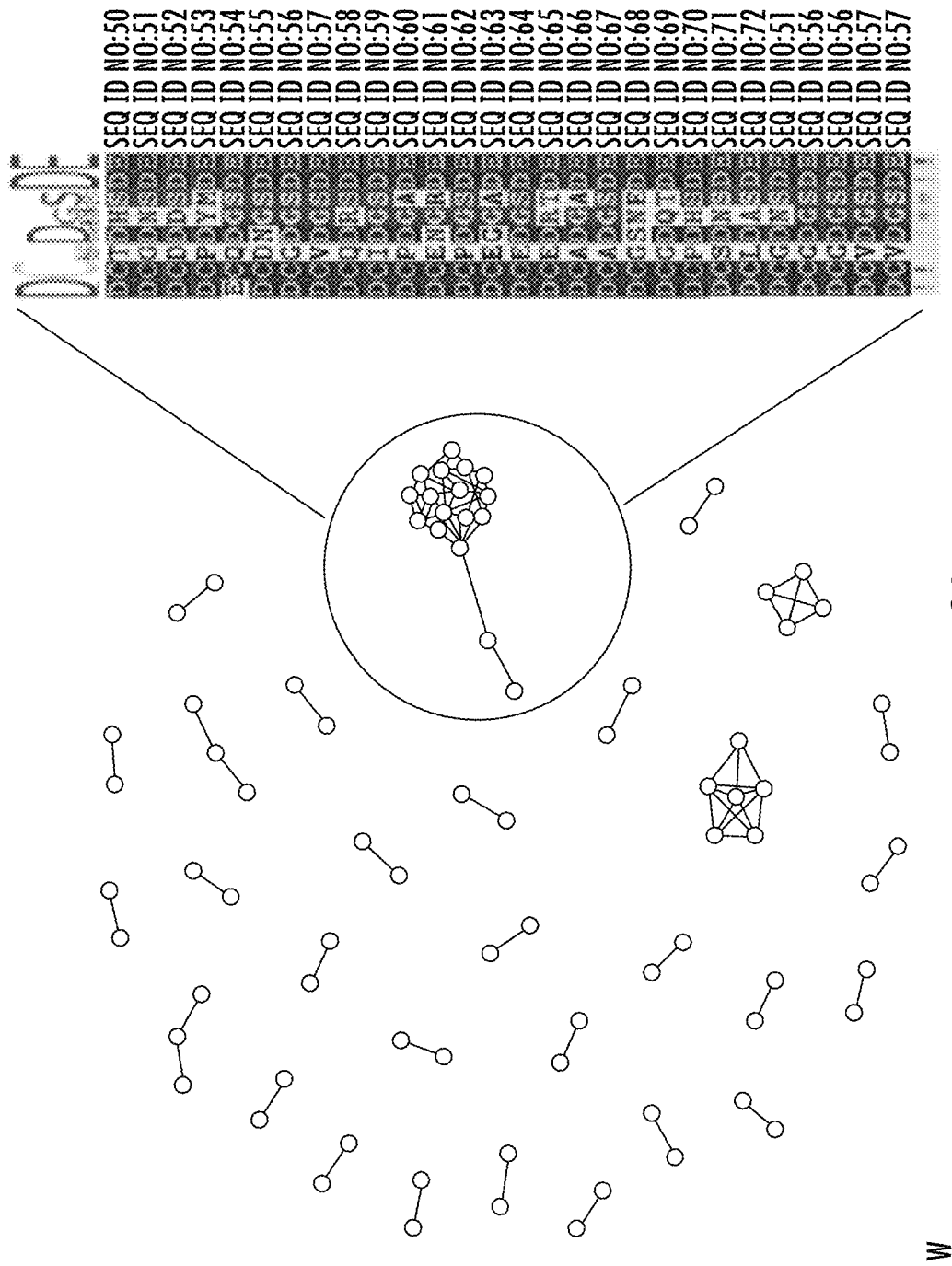
FIG. 2A-2E. HUWE1 is a novel Caspase-1 target.
Figure 7:
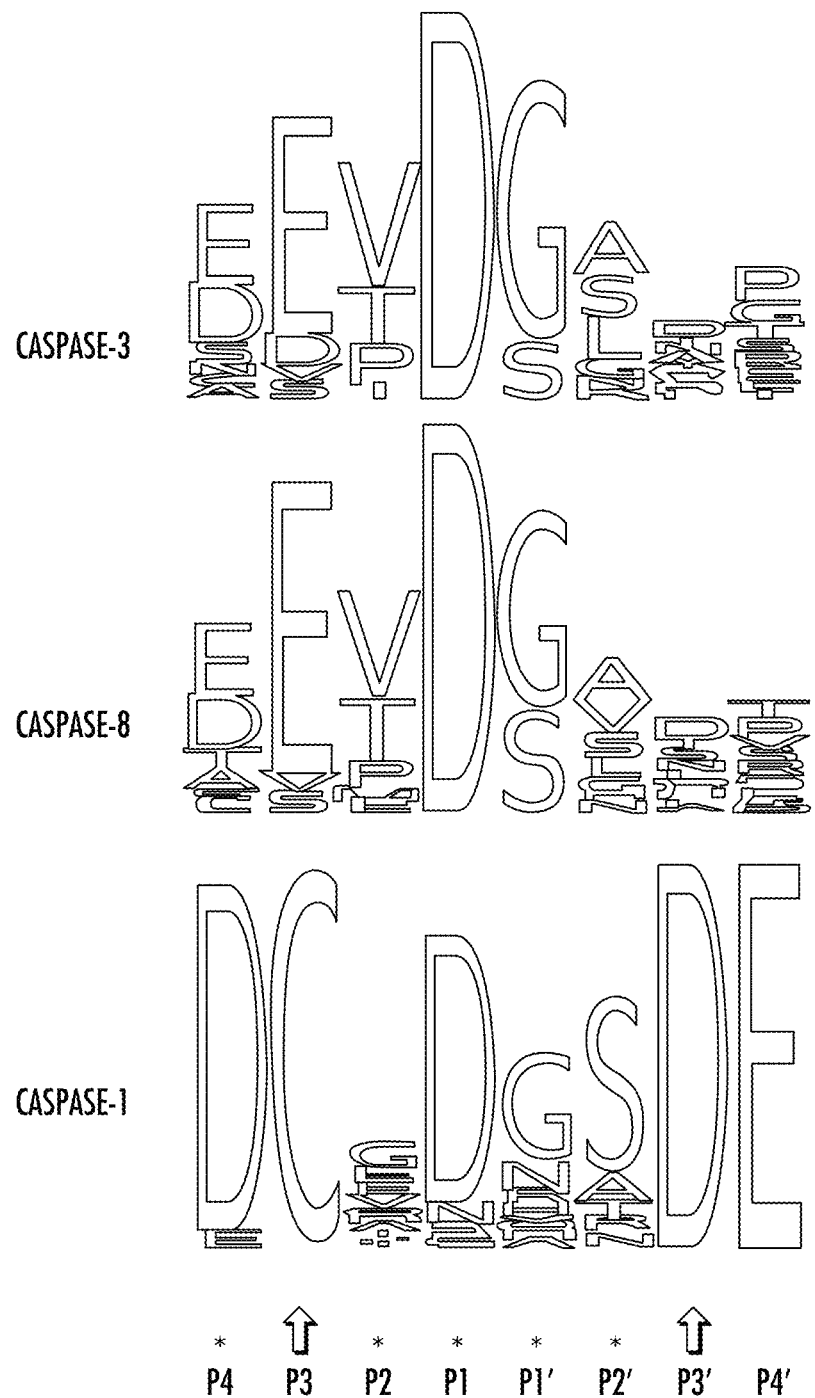
FIG. 7. Putative Caspase-1 cleavage motif resembles motifs for other Caspases. Logos for Caspase-3 and Caspase-8 from sequences reported in Bao et al., along with Caspase-1 motif for the largest cluster of peptides identified by EpitopeFindR. Sequence features shared by the family are marked by a black asterisk and features differentiating Caspase-1 from Caspases 3 and 8 are marked by a black arrow. The red asterisk marks the aspartic acid after which caspases cleave.

The present inventors next utilized SEPARATE to identify novel and biologically relevant substrates, even for well-studied proteases. Caspase-1 plays a key effector function as part of the inflammasome complex by producing mature interleukin-1β (IL-1β)21 and activating pyroptosis via cleavage of gasdermin D.[22,23] In our study, Caspase-1 was found to significantly cleave ~250 human peptide sequences corresponding to 230 unique genes. Peptides cleaved by Caspase-1 in the SEPARATE assay were analyzed using a motif detection algorithm, EpitopeFindr, which performs BLAST alignment of all peptides against each other to identify shared stretches of sequence homology.[24] The results of this analysis were visualized as a network graph in which peptides were linked based on their alignments (FIG. 2A). Peptides within the largest cluster identified the multiple sequence alignment logo -DCXDXXDE- (SEQ ID NO:5) which strongly resembles "canonical" motifs reported for Caspase-3 and Caspase-8.[25] We constructed a logo of the consensus sequence from a list of experimentally verified Caspase-3 and Caspase-8 substrates reported by Bao et al. and compared them to the features of Caspase-1. Amino acid preferences in the P4, P2, P1, P1' positions were similar between Caspase-3/8 and Caspase-1 even though the requirement for an aspartate in the P4 position appears more important for Caspase-1 (FIG. 7, black asterisks). However, there were stark differences between the groups in positions P3, P3' and P4' where the requirements for a cysteine, aspartate and glutamate appears to be more important to Caspase-1 (FIG. 7, black arrows). It is also worth noting that this motif only accounts for 17 peptides out of ~250 Caspase-1 enriched peptides and a vast majority of hits did not provide a clear consensus motif for cleavage.

Figure 2B:
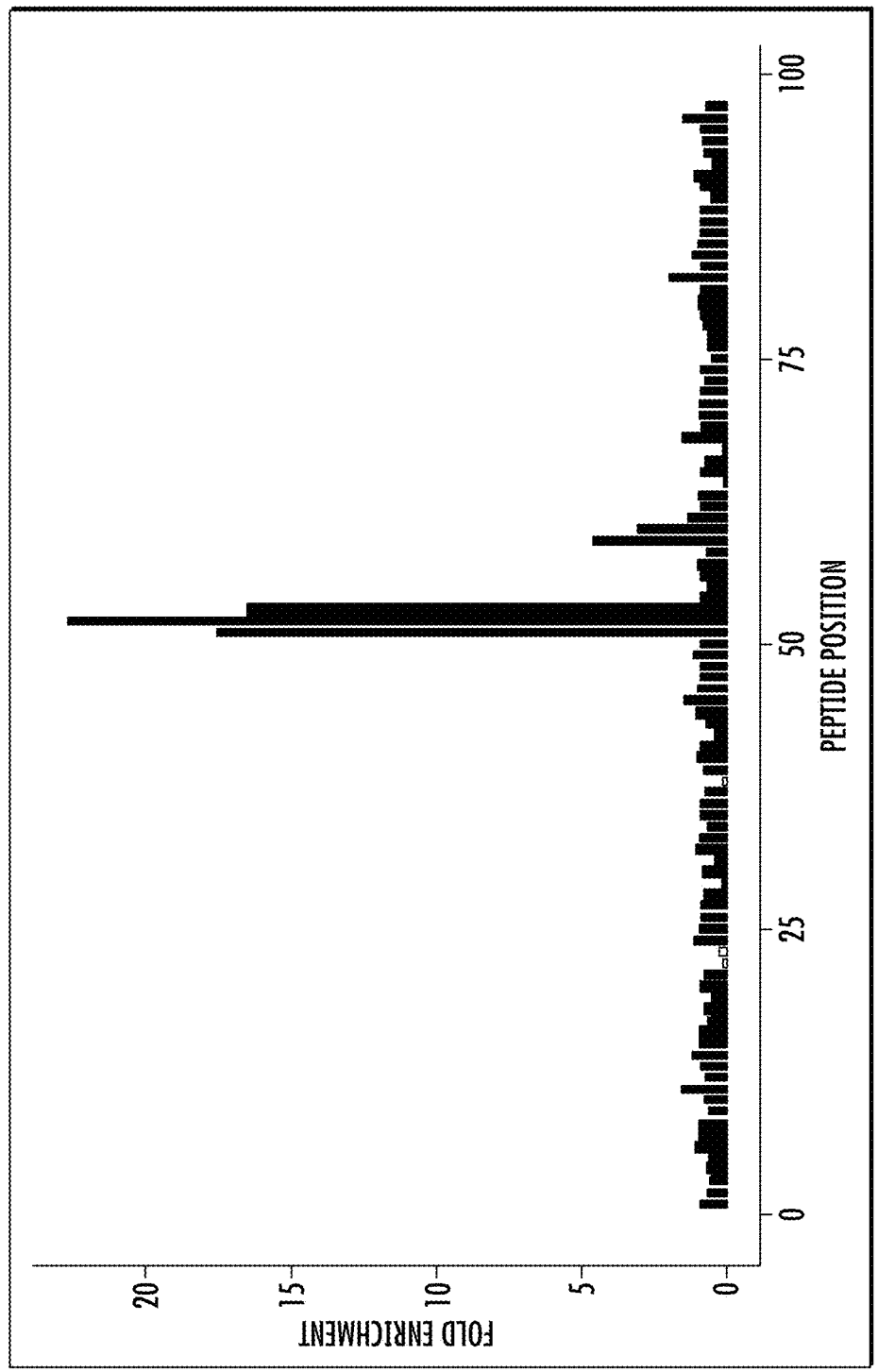
Figure 2C:
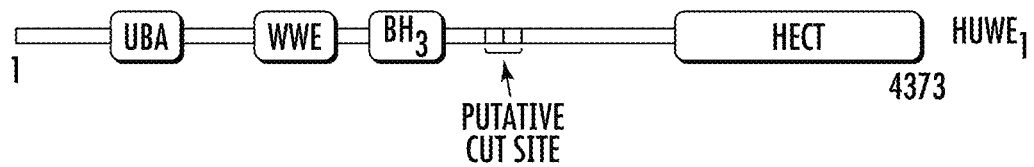
Figure 2D:
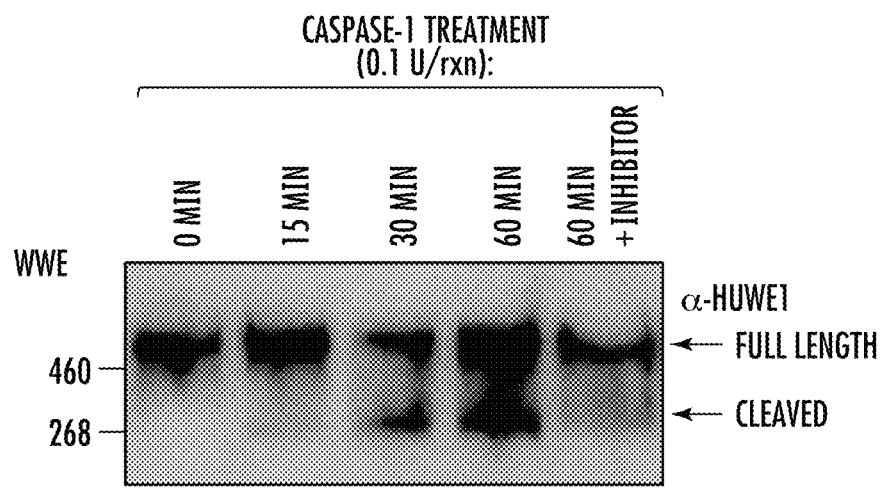
Figure 2E:
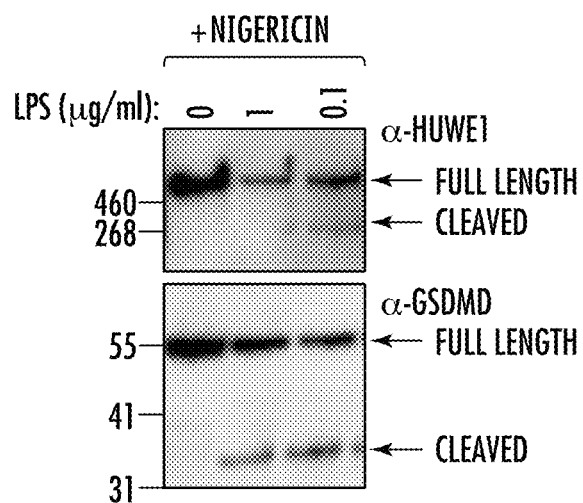

Interestingly, three peptides (two overlapping) derived from the protein HECT, UBA and WWE Domain Containing E3 Ubiquitin Protein Ligase 1 (HUWE1) were among the most significantly enriched, yet did not harbor the canonical cleavage motif (FIG. 2B and Table 2). HUWE1 (also known as LASU1, UREB1, MULE or ARF-BP1) is a well-known regulator of apoptosis, proliferation, DNA damage, and stress responses;[26-29] Caspase-1 cleavage of HUWE1 has not been previously reported. The HUWE1 protein is 482 kDa; Caspase-1 cleavage is predicted to produce two fragments of ~250 and ~230 kDa (FIG. 2C). We sought to validate HUWE1 as a Caspase-1 substrate using THP-1 human monocytic cells, which are commonly used for studies of inflammasome activation. Addition of recombinant Caspase-1 to unstimulated THP-1 cell lysates resulted in robust cleavage of endogenous HUWE1 (FIG. 2D). Physiological inflammasome activation in THP-1 cells using LPS and Nigericin resulted in Caspase-1 activation and the cleavage of endogenous HUWE1 into fragments of the size predicted by SEPARATE (FIG. 2E). Considering the role of HUWE1 in promoting apoptotic cell death, the present inventors hypothesize that its destruction by Caspase-1 could tip the balance towards inflammation-associated pyroptosis. These results confirm that SEPARATE can be used to identify novel proteolytic substrates of putative biological consequence, even for well-characterized proteases.

Figure 3A:
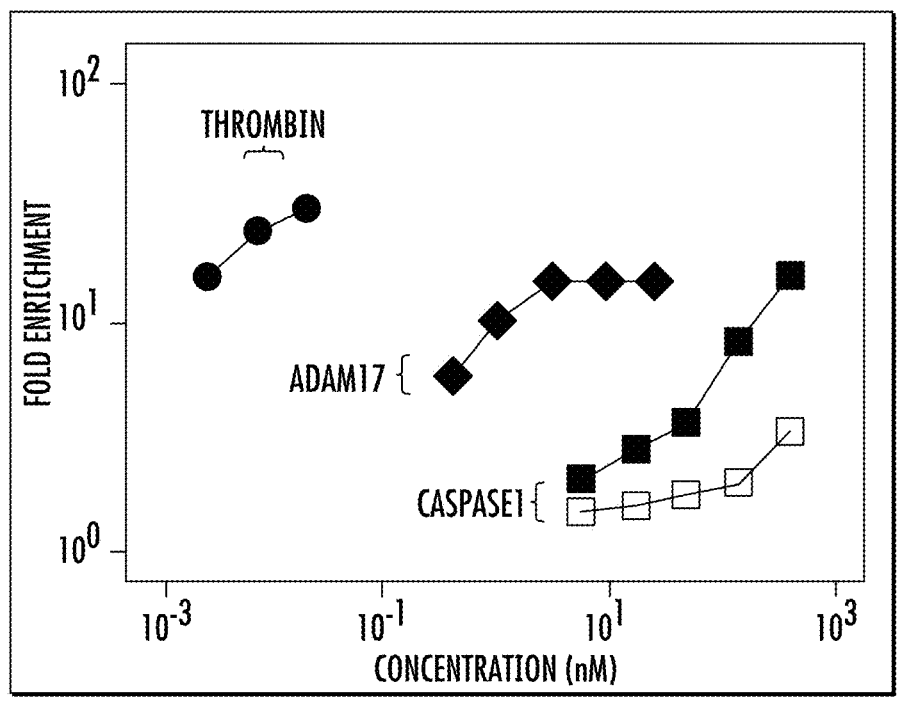
FIG. 3A-3D. SEPARATE detects known protease targets at or below physiological concentrations.
Figure 3B:
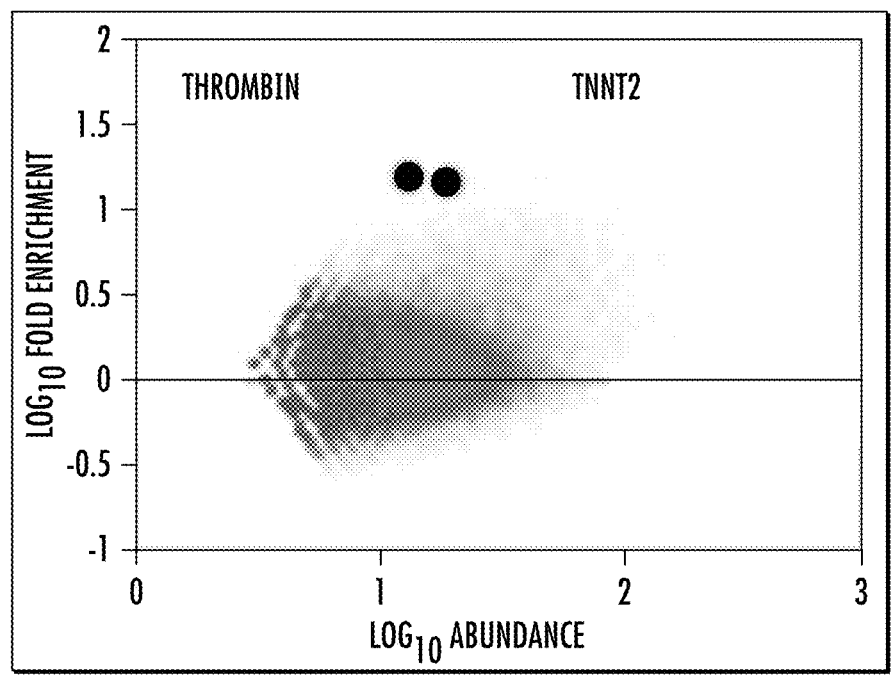
Figure 3C:
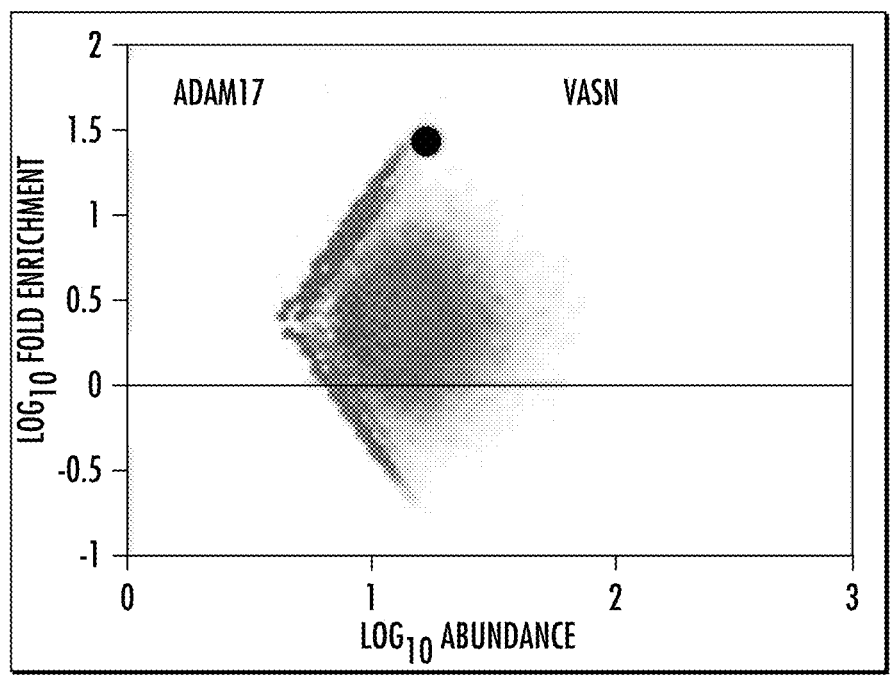
Figure 3D:
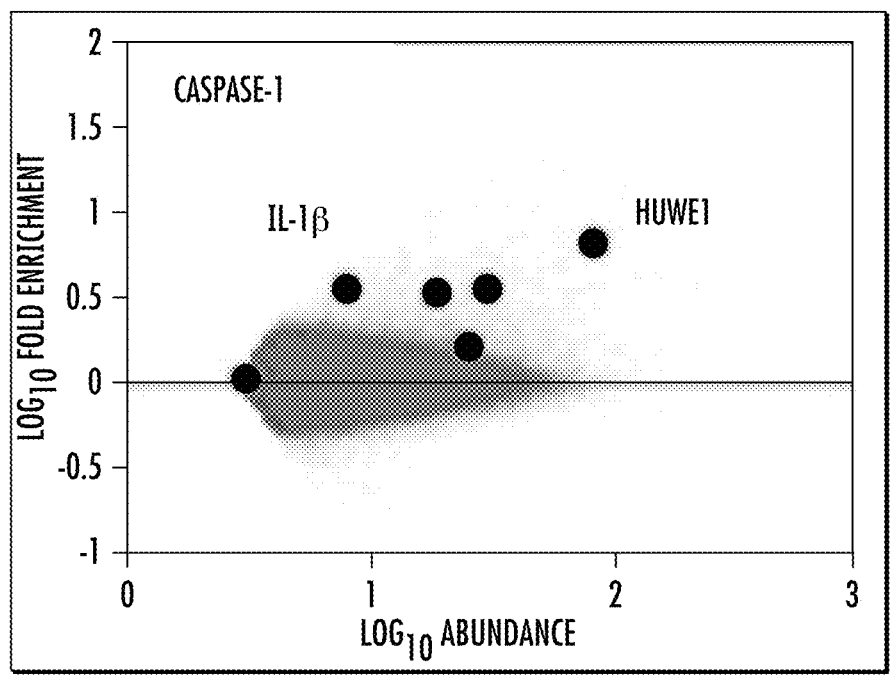

For SEPARATE to be useful in the analysis of complex cell or tissue lysates, it must have sufficient sensitivity at physiologically relevant enzyme concentrations. To this end, we performed SEPARATE on the human library and specifically focused on previously known substrates of well-characterized recombinant proteases from diverse catalytic classes. Testing serial dilutions of Caspase-1 (a cysteine protease), Thrombin (a serine protease), and ADAM17 (a zinc-dependent metalloprotease), concentration-dependent enrichments of known substrates were indeed detected for each enzyme at or below their reported physiological concentrations (FIG. 3A); these substrates ranked among the most significant enrichments for each of the corresponding enzymes (FIG. 3B-3D). Physiologically relevant concentration ranges for both ADAM17 and Thrombin have been reported previously in the range of 0.1-10 nM[30] and 1-1,000 nM[31,32] respectively. In our assay, we were able to detect targets for ADAM17 in reported physiological concentration ranges and for Thrombin at concentrations 1-3 logs lower than reported physiological ranges (1-100 pM). Here, the present inventors have highlighted selected known cleavage targets Vasorin (VASN) for ADAM17[33] and Cardiac troponin (TNNT2) for Thrombin[34]. VASN is a transmembrane transforming growth factor beta (TGF-β) binding protein that inhibits TGF-β signaling via ADAM17-dependent proteolytic release of its extracellular fragment.35 Although analysis of substrate cleavage sites has yet to reveal a unified consensus motif, proteolysis action by ADAM17 typically occurs at the juxtamembrane portion of the target.[36,37,38] SEPARATE identified a VASN peptide that encompasses amino acids 496-585, which maps to the juxtamembrane extracellular portion of the protein, in agreement with expectation.[39] SEPARATE was also able to identify other novel targets of ADAM17 that rank higher than VASN that are yet to be validated (Table 3). The Thrombin substrate TNNT2 serves as a biomarker of acute myocardial infarction. A previous study using spectrometry revealed two troponin digest fragments of amino acid residues 2-68 and 69-288.[40] Consistent with these findings, SEPARATE identified the first two tiles of the troponin peptide 1-90 and 46-135, which both include the putative troponin cut site at amino acid position 69 (Table 4, TNNT2 peptides marked in red). Additionally, to assess whether SEPARATE could be performed on a complex biological mixture, we used unstimulated THP-1 cell lysate supplemented with 0.1 units of recombinant Caspase-1. In this setting, HUWE1 peptides were again among the most significantly enriched targets (FIG. 3B).

Figure 8A:
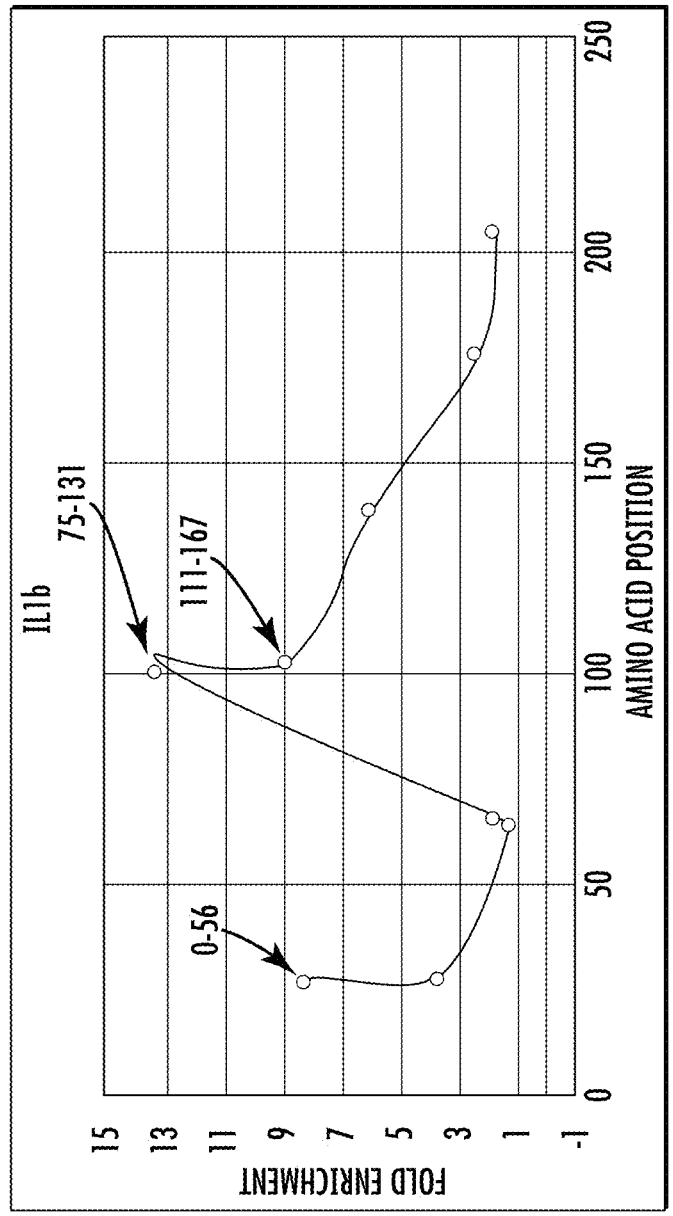
FIG. 8A-8B. Mouse IL-1β and Gsdmd cleavage sites of Caspase-1 are detected by SEPARATE.
Figure 8B:
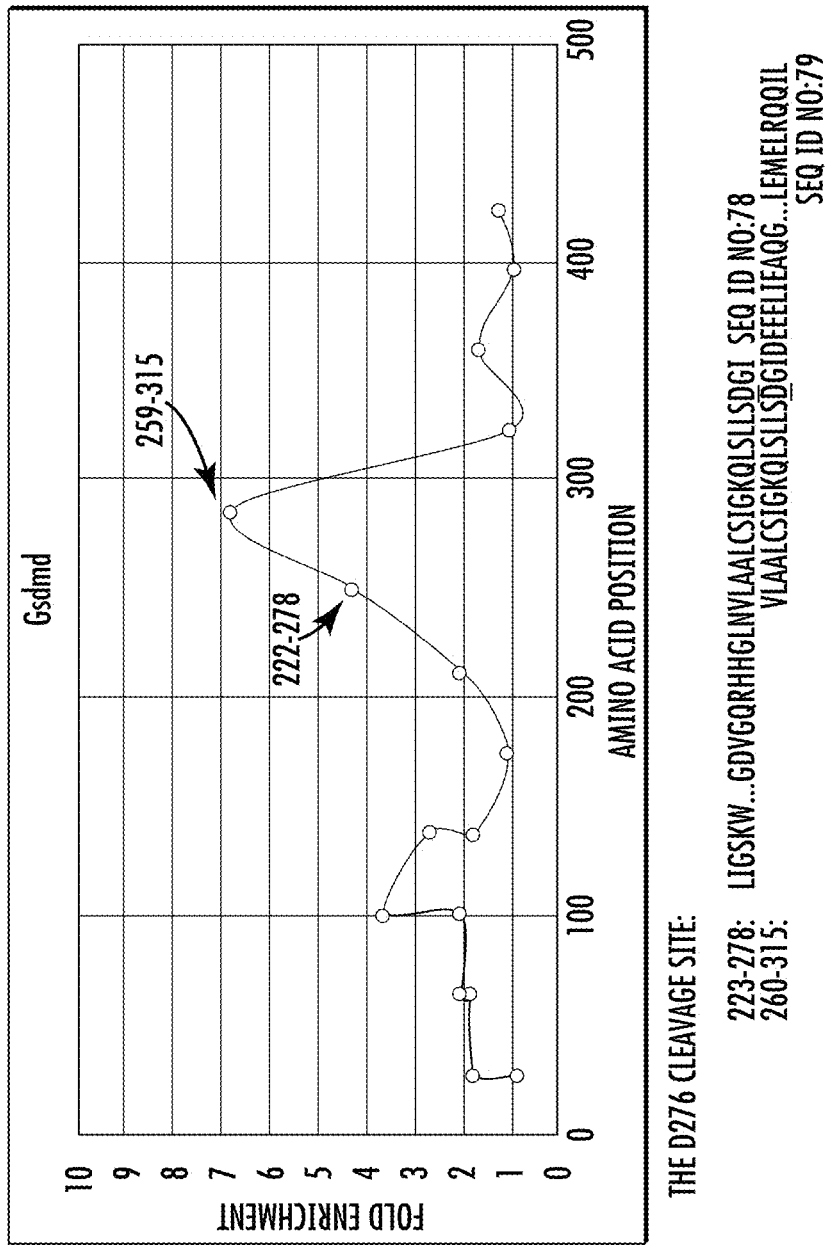
Figure 9:
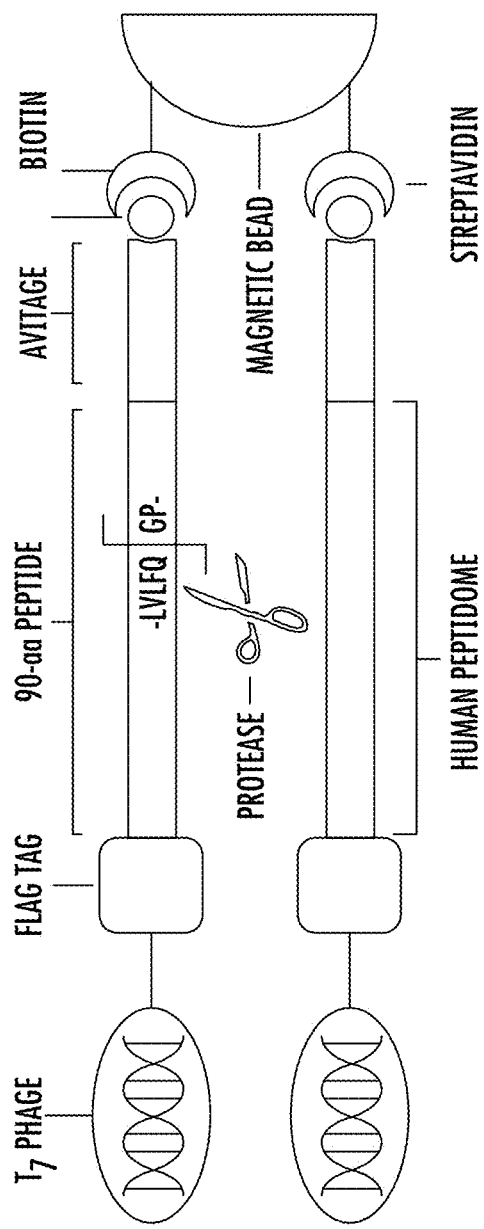
FIG. 9. The SEPARATE vector. Single-copy T7 phage display of the 90-aa human peptidome, flanked by affinity tags. Protease activity removes C-terminal biotin, permitting specific isolation of cleaved peptides via the N-terminal FLAG tag.

The performance of the SEPARATE assay is expected to depend on protease-substrate requirements as well as biophysical features of the peptide library. The present inventors have verified by PCR and Sanger sequencing that 90% of the immobilized human library lacks in-frame mutations. However, the well characterized Caspase-1 substrate Gasdermin-D did not score in the assay, and this was true for other canonical enzyme-substrate pairs such as Thrombin/Fibrinogen. To explore this further, a 56-amino acid mouse peptidome library (unpublished) was used in which both IL-1β and Gasdermin-D cleavage peptides are better represented. Some of the established targets of Caspase-1 were found to score in the mouse peptidome library as well (Table 5). Mouse IL-1β and Gasdermin-D are highly similar to the human versions and can serve as substrates for human Caspase-1. Mouse IL-1β is known to be cleaved by Caspase-1 after the D26 and D117 residues.[41] These two regions are covered by three peptides in the mouse peptidome library. Robust enrichments (7-13 fold) is observed for these peptides versus the IL-1β peptides lacking these cleavages sites (FIG. 8A). Similarly, Caspase-1 cleaves mouse Gasdermin-D after residue D276.22 As with IL-1β, Gasdermin-D peptides containing the cleavage sites are significantly enriched (4-7 fold, FIG. 8B). In both these instances, peptides representing these proteins were more abundant in the mouse library compared to the human library. In general, poor library representation of substrates, particular enzyme requirements for substrate conformation, cofactors, and/or post-translational modifications, are all expected to contribute to false negative SEPARATE assay results.

The SEPARATE assay can also yield false positive results. First, many peptides, which are not normally surface-exposed in the context of their full-length proteins, are presented for protease cleavage in the assay. Second, since the assay is performed outside the cellular context, enzymes and substrates that are typically sequestered in organelles or otherwise physically compartmentalized will be available for cleavage in the assay. Third, enzyme-substrate pairs that are not co-expressed in the same cells or are not expressed concurrently, may also inappropriately interact in the assay. Fourth, the biomolecular environment, including modulators of enzyme activity and posttranslational substrate modifications, may also impact the accuracy of the assay for certain substrate-enzyme pairs. For these reasons, SEPARATE should be viewed as a hypothesis generating technology, and novel candidate substrates must be validated using a more physiologically relevant assay.

Currently, there are large gaps in the knowledge of protease substrates, even for well-studied enzymes like Caspase-1. The present inventors have therefore developed the SEPARATE system for unbiased, high throughput, inexpensive, and automatable protease activity profiling using peptidome libraries monovalently displayed on phage.

While not always able to localize precise cleavage sites, SEPARATE can identify novel substrates and narrows down the recognition motif to 45-90 amino acids. Selecting an appropriate tiling density involves considering the tradeoffs between cleavage site resolution and the costs of library construction and sequencing analysis.

In a proof-of-concept study, the present inventors detected peptides that together recapitulated a canonical Caspase motif and identified a novel, non-canonical, physiological substrate, HUWE1, which was validated using standard approaches. The SEPARATE methodology is broadly applicable as it can be readily adapted to any soluble endopeptidase of interest, including endogenous and pathogen-associated proteases present within complex biological samples. It is therefore expected that unbiased protease profiling via approaches like SEPARATE will identify valuable new disease biomarkers and therapeutic targets.

TABLE 1

Characteristics of the human peptidome library.

| | Post-expansion library | Loaded on magnetic beads |
|---|---|---|
| Total number of designed peptides | 259,345 | 259,345 |
| Total read counts (TRC) | 10,481,974 (40.4X) | 7,108,499 (27.4X) |
| Detected peptides with TRC > 0 | 227,010 (87.53%) | 205,026 (79.05%) |

TABLE 2

Top 20 enriched peptides from human library digest with Caspase-1.

| Gene Name | Amino acid position | Caspase1 p_val | Caspase1 fold change |
|---|---|---|---|
| HUWE1 | 2296-2485 | 2.43E−04 | 22.71 |
| Efs | 181-270 | 1.34E−03 | 21.06 |
| LYST | 1171-1260 | 1.06E−03 | 21.04 |
| ERO1L | 91-180 | 6.53E−04 | 19.8 |
| Hyls1 | 1-90 | 9.59E−04 | 19.74 |
| Znf462 | 1-90 | 3.89E−04 | 19.1 |
| BSN | 631-720 | 9.57E−04 | 18.78 |
| unmapped_NM | 91-180 | 7.81E−04 | 18.72 |
| TNS3 | 451-540 | 4.20E−04 | 18.67 |
| C14orf93 | 91-180 | 6.86E−04 | 18.22 |
| HUWE1 | 2251-2340 | 1.51E−03 | 17.58 |
| hoxa2 | 271-360 | 5.52E−04 | 17.06 |
| ZNF469 | 811-900 | 9.14E−04 | 16.76 |
| HUWE1 | 2341-2430 | 1.31E−03 | 16.55 |
| MAP3K14 | 496-585 | 1.42E−03 | 16.5 |
| HMGXB4 | 226-315 | 6.29E−04 | 16.49 |
| LOC100287737 | 496-585 | 1.70E−03 | 16.43 |
| UHRF1BP1L | 991-1080 | 3.04E−03 | 16.39 |
| ANAPC1 | 1-90 | 7.69E−04 | 16.35 |
| Hmcn2 | 1576-1665 | 6.90E−04 | 16.27 |

TABLE 3

Top 20 enriched peptides from human library digest with ADAM17.

| Gene Name | Amino acid position | Sequence | Adam17 Fold Change |
|---|---|---|---|
| KCND1 | 541-630 | AIRLANSTASVSRGSMQELDMLAGLRRSHAPQSRSSLNAKPHDSLDLNCDSR DFVAAIISIPTPPANTPDESQPSSPGGGGRAGSTLRNS (SEQ ID NO: 6) | 57.97 |
| CIC | 901-990 | QSVSPVQAPPPGGSAQLLPGKVLVPLAAPSMSVRGGGAGQPLPLVSPPFSVPV QNGAQPPSKIIQLTPVPVSTPSGLVPPLSPATLPGPT (SEQ ID NO: 7) | 57.55 |

TABLE 3-continued

Top 20 enriched peptides from human library digest with ADAM17.

| Gene Name | Amino acid position | Sequence | Adam17 Fold Change |
|---|---|---|---|
| SPATC1 | 181-270 | SPLIAPVMGTVAVSLSSPLLSSTATPPGVSQNLLANPMSNLVLPEAPRLRLAEP LRGGPTGPQSPACVVPTATTKVPLSTEPPQSTQDPE (SEQ ID NO: 8) | 51.48 |
| MUC4 | 1351-1440 | SSVSTGHTTPLHVTDASSASTGQATPLPVTSLSSVSTGDTTPLPVTSPSSASTGH ATPLLVTDTSSASTGHATPLPVTDASSVSTDHATS (SEQ ID NO: 9) | 48.17 |
| SMTN | 361-450 | PARLLGPSLTSTTPASSSSGSSSRGPSDTSSRFSKEQRGVAQPLAQLRSCPQEEG PRGRGLAARPLENRAGGPVARSEEPGAPLPVAVGT (SEQ ID NO: 10) | 45.89 |
| LOC375295 | 46-135 | VLNSGARVWPSASALGLTAPPKDAEDRARPASGLRGARVLSEGREPRASLRV QVRPGLDVAAPGVCSLSCPSPPRSSAHPGPRGPLFPAL (SEQ ID NO: 11) | 44.03 |
| HMCN2 | 451-540 | HSALPFRLQLRRGEARLGEERHFQESGNSSWEILRASKAEEGTYECTAVSRAG TGRAKAQIVVTDPPPQLVPAPNVTVSPGETAVLSCRV (SEQ ID NO: 12) | 43.29 |
| MUC4 | 1666-1755 | PVTSTSSASTGHATPLPVTGLSSATTDDTTRLPVTDVSSASTGQATPLPVTSLS SVSTGDTTPLPVTSPSSASTGHASPLLVTDASSAST (SEQ ID NO: 13) | 41.41 |
| RBM14 | 226-315 | YVAPLTAQPATYRAQPSVSLGAAYRAQPSASLGVGYRTQPMTAQAASYRAQ PSVSLGAPYRGQLASPSSQSAAASSLGPYGGAQPSASAL (SEQ ID NO: 14) | 39.99 |
| IL1RAP | 541-630 | RLALPLRSLSASSGWNESCSSQSDISLDHVQRRRSRLKEPPELQSSERAAGSPP APGTMSKHRGKSSATCRCCVTYCEGENHLRNKSRAE (SEQ ID NO: 15) | 39.89 |
| LOC100293409 | 1801-1890 | ATPGAPGSSTPGEADIGNTSFGKSGKSGHDSLTVLNPAFLRRTPTVSAASTTSS PVSKHTDAASATAVTISGSKPGTPGTPGGATSGGKI (SEQ ID NO: 16) | 39.34 |
| TAF4B | 406-495 | KAGVVTLHSVGPTAATGTTAGTGLLQTSKPLVTSVANTVTTVSLQPEKPVVS GTAVTLSLPAVTFGETSGAAICLPSVKPVVSSAGTTS (SEQ ID NO: 17) | 39.07 |
| PHF21B | 1-90 | MELQSRPEALAVELARHQNGDLKKQLHERQPRIAALSDKQALGTITAVPVTG PQVSSLQRLAGQGAAVLPQVRPKTLIPDSLPVAPGRDR (SEQ ID NO: 18) | 38.34 |
| TTN | 271-360 | IAAKAQLARQQSPSPIRHSPSPVRHVRAPTSPVRSVSPAARISTSPIRSVR-SPLL MRKTQASTVATGPEVPPPWKQEGYVASSSEAEMR (SEQ ID NO: 19) | 37.14 |
| ATP7A | 1261-1350 | ARSIASQVGITKVFAEVLPSHKVAKVKQLQEEGKRVAMVGDGINDSPALAM ANVIAIGTGTDVAIEAADVVLIRNDLLDVVASIDLSRE (SEQ ID NO: 20) | 36.03 |
| RFX5 | 361-450 | KVATLPLSSRAGAPPAAVPIINMILPTVPALPGPGPGPGRAPPGGLTQPRGTEN REVGIGGDQGPHDKGVKRTAEVPVSEASGQAPPAKA (SEQ ID NO: 21) | 35.48 |
| FLYWCH1 | 226-315 | EPEPTPGLVLSKPALEEEEAPRALSLLSLPPKKRSILGLGQARPLEFLRTCYGGS FLVHESFLYKREKAVGDKVYWTCRDHALHGCRSRA (SEQ ID NO: 22) | 35.48 |
| PLEC | 91-180 | EIVPASLQRVRRPVAMVMPARRTPHVQAVQGPLGSPPKRGPLPTEEQRVYRR KELEEVSPETPVVPATTQRTLARPGPEPAPATDERDRV (SEQ ID NO: 23) | 34.93 |
| NUP210 | 811-900 | STRPVLASIEPELPMQLVSQDDESGQKKLHGLQAILVITEASGTTAITATATGY QESHLSSARTKQPHDPLVPLSASIELILVEDVRVSPE (SEQ ID NO: 24) | 34.57 |
| PRR14L | 1081-1170 | ARQEKLAFQEDSRSTLSRRELDAAHTGTTGQDSDFPVTAASTVDFLKIKKSCE ENVCRSLKDCEMEKCPDSCAHEMESVADHEPNKRILG (SEQ ID NO: 25) | 34.10 |

TABLE 4

Top 20 enriched peptides from human library digest with Thrombin.

| Gene Name | Amino acid position | Sequence | Thrombi Fold Change |
|---|---|---|---|
| TNNT2 | 46-135 | AETEETRAEEDEEEEEAKEAEDGPMEESKPKPRSFMPNLVPPKIPDGERVDFD DIHRKRMEKDLNELQALIEAHFENRKKEEEELVSLKD (SEQ ID NO: 26) | 19.08 |
| TNNT2 | 1-90 | MSDIEEVVEEYEEEQEEAAVEEEEDWREDEDEQEEAAEEDAEAEAETEETR AEEDEEEEAKEAEDGPMEESKPKPRSFMPNLVPPKIP (SEQ ID NO: 27) | 17.66 |
| LOC100290422 | 181-270 | SSALSGSGISRMQRPSSEAQMRMVASSEVDTRMSLERDQAKSETPRVWPRST RSTVGGAGTSWHREMLPSRPEDHPQTHLHAVKSSAATA (SEQ ID NO: 28) | 15.43 |

TABLE 4-continued

Top 20 enriched peptides from human library digest with Thrombin.

| Gene Name | Amino acid position | Sequence | Thrombi Fold Change |
|---|---|---|---|
| NOL7 | 1-90 | MVQLRPRASRAPASAEAMVDEGQLASEEEEAEHGLLLGQPSSGAAAEPLEED EEGDDEFDDEAPEELTFASAQAEAREEERRVRETVRRD (SEQ ID NO: 29) | 15.07 |
| SIPA1L2 | 1531-1620 | PRAHPAPSMGSLRNEFWFSDGSLSDKSKCADPGLMPLPDTATGLDWTHLVD AARAFEGLDSDEELGLLCHHTSYLDQRVASFCTLTDMQH (SEQ ID NO: 30) | 14.27 |
| NSMCE3 | 1-90 | MLQKPRNRGRSGGQAERDRDWSHSGNPGASRAGEDARVLRDGFAEEAPSTS RGPGGSQGSQGPSPQGARRAQAAPAVGPRSQKQLELKVS (SEQ ID NO: 31) | 12.49 |
| MTIF2 | 91-180 | VEVWIGMTIEELARAMEKNTDYVYEALLNTDIDIDSLEADSHLDEVWIKEVIT KAGMKLKWSKLKQDKVRKNKDAVRRPQADPALLTPRS (SEQ ID NO: 32) | 12.32 |
| NUP35 | 46-135 | PVTPQPRSISGPSVGVMEMRSPLLAGGSPPQPVVPAHKDKSGAPPVRSIYDDIS SPGLGSTPLTSRRQPNISVMQSPLVGVTSTPGTGQS (SEQ ID NO: 33) | 12.05 |
| TNNT2 | 1-90 | MSDIEEVVEEYEEEEQEEQEEAAEEDAEAEAETEETRAEEDEEEEEAKEAEDG PMEESKPKPRSFMPNLVPPKIPDGERVDFDDIHRKRM (SEQ ID NO: 34) | 11.56 |
| PCDH20 | 91-180 | LLPRSAGRPDPQSQLPERTGAEWNPPLSFSLASRGLSGQYVTLDNRSGELHTS AQEIDREALCVEGGGGTAWSGSVSISSSPSDSCLELL (SEQ ID NO: 35) | 11.53 |
| GPALPP1 | 181-270 | DSSKPIVRESWMTELPPEMKDFGEGPRTFKRRADDTSGDRSIWTDTPADRER KAKETQEARKSSSKKDEEHILSGRDKRLAEQVSSYNES (SEQ ID NO: 36) | 11.22 |
| ABL2 | 1-90 | MGQQVGRVGEAPGLQQPQPRGIRGSSAARPSGRRRDPAGRTTETGFNIFTQH DHFASCVEDGFEGDKTGGSSPEALBRPYGCDVEPQALN (SEQ ID NO: 37) | 11.16 |
| SLAIN2 | 46-135 | PGSPVRAGASIPSSGAASPRGFPLGLSAKSGGGPGSGPRRTSSEELRDATSLLA AGEGGLLDEVEPLRPDELERLSGWEEEEESWLYSSP (SEQ ID NO: 38) | 11.10 |
| CCNI2 | 46-135 | APLPRSNRSRCPGTRQPGAASLHAASAAVPVRPRRGTAPAGKTADAVPAAAP EQAPRPAPQSRKPRNLEGDLDERRLLCHLQLAQDREAR (SEQ ID NO: 39) | 10.98 |
| ZSCAN10 | 46-135 | LGREQGQPERDGEEVVLLLEGIHREPSHAGPLDFSCNAGKSCPRADVTLEEKG CASQVPSHSPKKELPAEEPSVLGPSDEPPRPQPRAAQ (SEQ ID NO: 40) | 10.92 |
| CCDC86 | 136-225 | SELAQNKEELTPGAPQHQLPPVPGSPEPYPGQQAPGPEPSQPLLELTPRAPGSP RGQHEPSKPPPAGETVTGGFGAKKRKGSSQAPASK (SEQ ID NO: 41) | 10.90 |
| MED13L | 991-1080 | ATFIRDGYNNVPSVGSLADPDYLNTPQMNTPVTENSAAPASNSGAGVLPSPA TPRFSVPTPRTPRTPRTPRGGGTASGQGSVKYDSTDQG (SEQ ID NO: 42) | 10.80 |
| PDLIM2 | 181-270 | AGLGRAGDSAVLVLPPSPGPRSSRPSMDSEGGSLLLDEDSEVFKMLQENREG RAAPRQSSSFRLLQEALEAEERGGTPAFLPSSLSPQSS (SEQ ID NO: 43) | 10.76 |
| LOC100287196 | 181-270 | SLEALGMPRAYRLPSSFERVPCQTESSGPVPTIDRAGTEFDMAAKHLQSQSTP QAQARSKGSVALMNEKQKPHLQGSELRTEKLLSEGL (SEQ ID NO: 44) | 10.68 |
| TNNT2 | 1-90 | MSDIEEVVEEYEEEEQEEAAVEEQEEAAEEDAEAEAETEETRAEEDEEEEEAK EAEDGPMEESKPKPRSFMPNLVPPKIPDGERVDFDDI (SEQ ID NO: 45) | 10.44 |

TABLE 5

Selected peptides from mouse library digested with Caspase-1.

| Gene Name | Amino acid position | Caspase1 fold change |
|---|---|---|
| HUWE1 | 2328-2384 | 23.12 |
| HUWE1 | 2291-2347 | 6.13 |
| IL1B | 74-130 | 13.23 |
| IL1B | 75-131 | 8.80 |
| IL1B | 0-56 | 8.10 |
| GSDMD | 259-315 | 6.78 |
| GSDMD | 222-278 | 4.23 |

Example 2: SEPARATE Assay Useful in Candidate Drug Candidate Evaluation

A cell line is treated with a drug or compound that activates or inhibits proteases and cell extracts will be prepared in a buffer that preserves the activity of proteases. The extract is then mixed with an immobilized substrate library and the SEPARATE assay for protease activity profiling of the present invention performed as described in the specification. Fold-enrichment of peptides will be calculated by comparing the drug treated cell line to a control untreated cell line. The mixture of proteases in the cell extract may optionally be "deconvoluted" using data sets previously generated by analyzing individual proteases or examination of the literature.

Example 3: SEPARATE Assay Performed on Patient Sample

Patient specimens like tumor resections, biopsies, blood plasma, blood serum, bodily secretions, etc., are solubilized in an appropriate lysis/dilution buffer. These extracts are inputs to the SEPARATE assay for protease activity profiling of the present invention against the human peptidome. Differentially active protease are determined by comparison with matched samples from healthy donor or uninvolved tissue controls. The mixture of proteases detectable in the cell extract may optionally be deconvoluted using data sets previously generated by analyzing individual proteases or examination of the literature.

Example 4: SEPARATE Assay Useful to Profile Viral Proteases

To utilize the SEPARATE assay to profile viral proteases, a permissive cell line is infected with a virus and cell extracts prepared at different times post infection. The extracts are used to perform the SEPARATE assay for protease activity profiling of the present invention as described herein. Comparisons are made between the infected and negative control uninfected cell line to establish a virus specific protease cleavage signature. The mixture of host protease activities detectable in the cell extract may optionally be deconvoluted using data sets previously generated by analyzing individual proteases or examination of the literature. This can be done separately from the deconvolution of virus-specific protease activities.

REFERENCES

1. Lopez-Otin, C. & Bond, J. S. Proteases: Multifunctional Enzymes in Life and Disease. J. Biol. Chem. 283, 30433-30437 (2008).
2. Tong, L. Viral proteases. Chem. Rev. 102, 4609-4626 (2002).
3. Ingmer, H. & Brondsted, L. Proteases in bacterial pathogenesis. Res. Microbiol. 160, 704-710 (2009).
4. Liyanage, C., Fernando, A. & Batra, J. Differential roles of protease isoforms in the tumor microenvironment. Cancer Metastasis Rev. (2019) doi:10.1007/s10555-019-09816-2.
5. Culp, E. & Wright, G. D. Bacterial proteases, untapped antimicrobial drug targets. J. Antibiot. (Tokyo) 70, 366-377 (2017).
6. Kaman, W. E., Hays, J. P., Endtz, H. P. & Bikker, F. J. Bacterial proteases: targets for diagnostics and therapy. Eur. J. Clin. Microbiol. Infect. Dis. Off. Publ. Eur. Soc. Clin. Microbiol. 33, 1081-1087 (2014).
7. Deu, E. Proteases as antimalarial targets: strategies for genetic, chemical, and therapeutic validation. FEBS J. 284, 2604-2628 (2017).
8. Caughey, G. H. Mast cell proteases as pharmacological targets. Eur. J. Pharmacol. 778, 44-55 (2016).
9. Goard, C. A. & Schimmer, A. D. Mitochondrial matrix proteases as novel therapeutic targets in malignancy. Oncogene 33, 2690-2699 (2014).
10. Rawlings, N. D., Barrett, A. J. & Bateman, A. MEROPS: the database of proteolytic enzymes, their substrates and inhibitors. Nucleic Acids Res. 40, D343-D350 (2012).
11. van den Berg, B. H. J. & Tholey, A. Mass spectrometry-based proteomics strategies for protease cleavage site identification. Proteomics 12, 516-529 (2012).
12. Klingler, D. & Hardt, M. Profiling protease activities by dynamic proteomics workflows. Proteomics 12, 587-596 (2012).
13. Sanman, L. E. & Bogyo, M. Activity-Based Profiling of Proteases. Annu. Rev. Biochem. 83, 249-273 (2014).
14. Chakrabarty, S., Kahler, J. P., van de Plassche, M. A. T., Vanhoutte, R. & Verhelst, S. H. L. Recent Advances in Activity-Based Protein Profiling of Proteases. Curr. Top. Microbiol. Immunol. 420, 253-281 (2019).
15. Dudani, J. S., Ibrahim, M., Kirkpatrick, J., Warren, A. D. & Bhatia, S. N. Classification of prostate cancer using a protease activity nanosensor library. Proc. Natl. Acad. Sci. U.S.A 115, 8954-8959 (2018).
16. Kwon, E. J., Dudani, J. S. & Bhatia, S. N. Ultrasensitive tumour-penetrating nanosensors of protease activity. Nat. Biomed. Eng. 1, (2017).
17. Matthews, D. J. & Wells, J. A. Substrate phage: selection of protease substrates by monovalent phage display. Science 260, 1113-1117 (1993).
18. Beck, Z. Q., Hervio, L., Dawson, P. E., Elder, J. H. & Madison, E. L. Identification of efficiently cleaved substrates for HIV-1 protease using a phage display library and use in inhibitor development. Virology 274, 391-401 (2000).
19. Kretz, C. A., Tomberg, K., Esbroeck, A., Yee, A. & Ginsburg, D. High throughput protease profiling comprehensively defines active site specificity for thrombin and ADAMTS13. Sci. Rep. 8, 2788 (2018).
20. Xu, G. J. et al. Systematic autoantigen analysis identifies a distinct subtype of scleroderma with coincident cancer. Proc. Natl. Acad. Sci. U.S.A 113, E7526-E7534 (2016).
21. Franchi, L., Eigenbrod, T., Mufoz-Planillo, R. & Nufez, G. The Inflammasome: A Caspase-1 Activation Platform Regulating Immune Responses and Disease Pathogenesis. Nat. Immunol. 10, 241 (2009).
22. Shi, J. et al. Cleavage of GSDMD by inflammatory caspases determines pyroptotic cell death. Nature 526, 660-665 (2015).
23. Zhao, Y., Shi, J. & Shao, F. Inflammatory Caspases: Activation and Cleavage of Gasdermin-D In Vitro and During Pyroptosis. Methods Mol. Biol. Clifton NJ 1714, 131-148 (2018).
24. Minimal Overlaps from BLAST Alignments•epitopefindr. https://brandonsie.github.io/epitopefindr/(2019).
25. Bao, Y. et al. Toward more accurate prediction of caspase cleavage sites: a comprehensive review of current methods, tools and features. Brief. Bioinform. doi:10.1093/bib/bby041.
26. Kao, S.-H., Wu, H.-T. & Wu, K.-J. Ubiquitination by HUWE1 in tumorigenesis and beyond. J. Biomed. Sci. 25, 67 (2018).
27. Kurokawa, M. et al. A Network of Substrates of the E3 Ubiquitin Ligases MDM2 and HUWE1 Control Apoptosis Independently of p53. Sci. Signal. 6, ra32-ra32 (2013).
28. Hall, J. R. et al. Cdc6 Stability Is Regulated by the Huwel Ubiquitin Ligase after DNA Damage. Mol. Biol. Cell 18, 3340-3350 (2007).
29. Zhong, Q., Gao, W., Du, F. & Wang, X. Mule/ARF-BP1, a BH3-only E3 ubiquitin ligase, catalyzes the polyubiquitination of Mcl-1 and regulates apoptosis. Cell 121, 1085-1095 (2005).

30. Bertram, A. et al. Circulating ADAM17 Level Reflects Disease Activity in Proteinase-3 ANCA-Associated Vasculitis. J. Am. Soc. Nephrol. JASN 26, 2860-2870 (2015).
31. Garcia, P. S. et al. Concentration-Dependent Dual Role of Thrombin in Protection of Cultured Rat Cortical Neurons. Neurochem. Res. 40, 2220-2229 (2015).
32. Allen, G. A. et al. Impact of procoagulant concentration on rate, peak and total thrombin generation in a model system. J. Thromb. Haemost. JTH 2, 402-413 (2004).
33. Malapeira, J., Esselens, C., Bech-Serra, J. J., Canals, F. & Arribas, J. ADAM17 (TACE) regulates TGFβ signaling through the cleavage of vasorin. Oncogene 30, 1912-1922 (2011).
34. Katrukha, I. A. et al. Thrombin-Mediated Degradation of Human Cardiac Troponin T. Clin. Chem. 63, 1094-1100 (2017).
35. Malapeira, J., Esselens, C., Bech-Serra, J. J., Canals, F. & Arribas, J. ADAM17 (TACE) regulates TGFβ signaling through the cleavage of vasorin. Oncogene 30, 1912-1922 (2011).
36. Gooz, M. ADAM-17: the enzyme that does it all. Crit. Rev. Biochem. Mol. Biol. (2010) doi:10.3109/10409231003628015.
37. Mishra, H. K., Ma, J. & Walcheck, B. Ectodomain Shedding by ADAM17: Its Role in Neutrophil Recruitment and the Impairment of This Process during Sepsis. Front. Cell. Infect. Microbiol. 7, (2017).
38. Mezyk, R., Bzowska, M. & Bereta, J. Structure and functions of tumor necrosis factor-alpha converting enzyme. Acta Biochim. Pol. 50, 625-645 (2003).
39. VASN—Vasorin precursor—*Homo sapiens* (Human)—VASN gene & protein. https://www.uniprot.org/uniprot/Q6EMK4.
40. Katrukha, I. A. et al. Thrombin-Mediated Degradation of Human Cardiac Troponin T. Clin. Chem. 63, 1094-1100 (2017).
41. Howard, A. D. et al. IL-1-CONVERTING ENZYME REQUIRES ASPARTIC ACID RESIDUES FOR PROCESSING OF THE IL-1/3 PRECURSOR AT TWO DISTINCT SITES AND DOES NOT CLEAVE 31-kDa IL-Ia. 7.
42. Waugh, D. S. An overview of enzymatic reagents for the removal of affinity tags. Protein Expr. Puri/. 80, 283-293 (2011).
43. Fairhead, M. & Howarth, M. Site-specific biotinylation of purified proteins using BirA. Methods Mol. Biol. Clinton NJ 1266, 171-184 (2015).
44. Mohan, D. et al. PhIP-Seq characterization of serum antibodies using oligonucleotide-encoded peptidomes. Nat. Protoc. 13, 1958-1978 (2018).
45. Larman, H. B. et al. Autoantigen discovery with a synthetic human peptidome. Nat. Biotechnol. 29, 535-541 (2011).

---

That which is claimed:

1. A bacteriophage display vector comprising a nucleic acid sequence encoding:
   (a) a peptide to be displayed on the surface of the bacteriophage, wherein the peptide is a candidate protease substrate encoded by a synthetic oligonucleotide;
   (b) a first affinity tag distal to the peptide that immobilizes the bacteriophage to a solid support; and
   (c) a second affinity tag proximal to the peptide for recapture of released bacteriophage following cleavage by a protease.

2. The bacteriophage display vector of claim 1, wherein the first affinity tag comprises a biotin labeling tag.

3. The bacteriophage display vector of claim 1, wherein the second affinity tag comprises at least one FLAG tag.

4. The bacteriophage display vector of claim 3, wherein the second affinity tag comprises a 3× FLAG tag.

5. The bacteriophage display vector of claim 1, further comprising an enterokinase cleavage site proximal to the peptide.

6. The bacteriophage display vector of claim 1, wherein the displayed peptide tiles with other displayed peptides to comprise a human peptidome.

7. The bacteriophage display vector of claim 1, wherein the bacteriophage is T7 or M13.

8. The bacteriophage display vector of claim 1, further comprising an epitope tag between the peptide and the first affinity tag.

9. The bacteriophage display vector of claim 8, wherein the epitope tag comprises a V5 tag.

10. The bacteriophage display vector of claim 1, further comprising a protease cleavage site between the peptide and the first affinity tag.

11. The bacteriophage display vector of claim 10, wherein the protease comprises the TEV protease.

12. A bacteriophage peptide display library comprising a plurality of bacteriophage display vectors each comprising a nucleic acid sequence encoding:
   (a) a peptide to be displayed on the surface of the bacteriophage, wherein the peptide is a candidate protease substrate encoded by a synthetic oligonucleotide;
   (b) a first affinity tag distal to the peptide that immobilizes the bacteriophage to a solid support; and
   (c) a second affinity tag proximal to the peptide for recapture of released bacteriophage following cleavage by a protease.

13. The bacteriophage peptide display library of claim 12, wherein the first affinity tag comprises a biotin labeling tag.

14. The bacteriophage peptide display library of claim 12, wherein the second affinity tag comprises at least one FLAG tag.

15. The bacteriophage peptide display library of claim 13, wherein the second affinity tag comprises a 3× FLAG tag.

16. The bacteriophage peptide display library of claim 12, wherein the plurality of bacteriophage display vectors further comprise an enterokinase cleavage site proximal to the peptide.

17. The bacteriophage peptide display library of claim 12, wherein the bacteriophage is T7 or M13.

18. The bacteriophage peptide display library of claim 12, wherein the plurality of bacteriophage display vectors further comprise an epitope tag between the peptide and the first affinity tag.

19. The bacteriophage peptide display library of claim 18, wherein the epitope tag comprises a V5 tag.

20. The bacteriophage peptide display library of claim 12, wherein the plurality of bacteriophage display vectors further comprise a protease cleavage site between the peptide and the first affinity tag.

21. The bacteriophage peptide display library of claim 20, wherein the protease comprises the TEV protease.

22. The bacteriophage peptide display library of claim 12, wherein the displayed peptides comprise the human peptidome.

23. The bacteriophage peptide display library of claim 12, wherein the displayed peptides comprise at least 10 proteins.

24. The bacteriophage peptide display library of claim 12, wherein the displayed peptides are each less than 100, 200 or 300 amino acids long.

25. The bacteriophage peptide display library of claim 12, wherein each displayed peptide comprises a common adapter region appended to the end of the nucleic acid sequence encoding the peptide.

26. A method for profiling protease activity comprising the steps of:
   (a) contacting a reaction sample comprising the bacteriophage peptide display library of claim 12, with a capture agent that specifically binds the first affinity tag to form an immobilized bacteriophage peptide display library;
   (b) contacting the immobilized bacteriophage peptide display library with a sample comprising at least one protease under conditions that would allow the at least one protease to cleave at least one displayed peptide, thereby releasing a population of at least one composition comprising the bacteriophage particle, the second affinity tag proximal to the peptide and a first portion of the cleaved peptide;
   (c) isolating the population of step (b) with a capture agent that specifically binds the second affinity tag; and
   (d) amplifying deoxyribonucleic acid (DNA) within the bacteriophage particle that encodes the displayed peptide.

27. The method of claim 26, further comprising the step of (e) sequencing the amplified DNA of step (d).

28. The method of claim 27, wherein the sequencing step comprises next generation sequencing.

29. The method of claim 26, further comprising the step of (e) performing microarray hybridization to detect the amplified sequences of step (d).

30. The method of claim 26, wherein step (d) comprises real-time polymerase chain reaction (PCR).

31. The method of claim 27, wherein the amplified DNA of step (d) further comprises a DNA proxy.

32. The method of claim 31, wherein the DNA proxy is a peptide-specific barcode sequence.

33. The method of claim 26, wherein in step (a), the binding of the capture agent to the first affinity tag forms an irreversibly immobilized bacteriophage peptide display library.

* * * * *

SEQUENCE LISTING

```
<160> NUMBER OF SEQ ID NOS: 79

<210> SEQ ID NO 1
<211> LENGTH: 8
<212> TYPE: PRT
<213> ORGANISM: Artificial Sequence
<220> FEATURE:
<223> OTHER INFORMATION: PreScission protease cleavage site

<400> SEQUENCE: 1

Leu Glu Val Leu Phe Gln Gly Pro
1               5

<210> SEQ ID NO 2
<211> LENGTH: 15
<212> TYPE: PRT
<213> ORGANISM: Artificial Sequence
<220> FEATURE:
<223> OTHER INFORMATION: AviTag biotinylation sequence

<400> SEQUENCE: 2

Gly Leu Asn Asp Ile Phe Glu Ala Gln Lys Ile Glu Trp His Glu
1               5                   10                  15

<210> SEQ ID NO 3
<211> LENGTH: 20
<212> TYPE: DNA
<213> ORGANISM: Artificial Sequence
<220> FEATURE:
<223> OTHER INFORMATION: T7-Pep2_PCR1_F forward primer

<400> SEQUENCE: 3
ataaaggtga gggtaatgtc                                            20

<210> SEQ ID NO 4
<211> LENGTH: 49
```

```
<212> TYPE: DNA
<213> ORGANISM: Artificial Sequence
<220> FEATURE:
<223> OTHER INFORMATION: T7-SEPARATE vector specific reverse primer

<400> SEQUENCE: 4
ctggagttca gacgtgtgct cttccgatca acccctcaag acccgttta          49

<210> SEQ ID NO 5
<211> LENGTH: 8
<212> TYPE: PRT
<213> ORGANISM: Artificial Sequence
<220> FEATURE:
<223> OTHER INFORMATION: Multiple sequence alignment logo for Caspase-1
<220> FEATURE:
<221> NAME/KEY: MISC_FEATURE
<223> OTHER INFORMATION: X=any amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 5

Asp Cys Xaa Asp Xaa Xaa Asp Glu
1               5

<210> SEQ ID NO 6
<211> LENGTH: 90
<212> TYPE: PRT
<213> ORGANISM: Homo sapiens

<400> SEQUENCE: 6

Ala Ile Arg Leu Ala Asn Ser Thr Ala Ser Val Ser Arg Gly Ser Met
1               5                   10                  15

Gln Glu Leu Asp Met Leu Ala Gly Leu Arg Arg Ser His Ala Pro Gln
                20                  25                  30

Ser Arg Ser Ser Leu Asn Ala Lys Pro His Asp Ser Leu Asp Leu Asn
            35                  40                  45

Cys Asp Ser Arg Asp Phe Val Ala Ala Ile Ile Ser Ile Pro Thr Pro
    50                  55                  60

Pro Ala Asn Thr Pro Asp Glu Ser Gln Pro Ser Ser Pro Gly Gly Gly
65                  70                  75                  80

Gly Arg Ala Gly Ser Thr Leu Arg Asn Ser
                85                  90

<210> SEQ ID NO 7
<211> LENGTH: 91
<212> TYPE: PRT
<213> ORGANISM: Homo sapiens

<400> SEQUENCE: 7

Gln Ser Val Ser Pro Val Gln Ala Pro Pro Gly Gly Ser Ala Gln
1               5                   10                  15

Leu Leu Pro Gly Lys Val Leu Val Pro Leu Ala Ala Pro Ser Met Ser
                20                  25                  30

Val Arg Gly Gly Gly Ala Gly Gln Pro Leu Pro Leu Val Ser Pro Pro
            35                  40                  45

Phe Ser Val Pro Val Gln Asn Gly Ala Gln Pro Pro Ser Lys Ile Ile
    50                  55                  60
```

```
Gln Leu Thr Pro Val Pro Val Ser Thr Pro Ser Gly Leu Val Pro Pro
 65                  70                  75                  80

Leu Ser Pro Ala Thr Leu Pro Gly Pro Thr Ala
                 85                  90

<210> SEQ ID NO 8
<211> LENGTH: 90
<212> TYPE: PRT
<213> ORGANISM: Homo sapiens

<400> SEQUENCE: 8

Ser Pro Leu Ile Ala Pro Val Met Gly Thr Val Ala Val Ser Leu Ser
  1               5                  10                  15

Ser Pro Leu Leu Ser Ser Thr Ala Thr Pro Pro Gly Val Ser Gln Asn
                 20                  25                  30

Leu Leu Ala Asn Pro Met Ser Asn Leu Val Leu Pro Glu Ala Pro Arg
             35                  40                  45

Leu Arg Leu Ala Glu Pro Leu Arg Gly Gly Pro Thr Gly Pro Gln Ser
         50                  55                  60

Pro Ala Cys Val Val Pro Thr Ala Thr Thr Lys Val Pro Leu Ser Thr
 65                  70                  75                  80

Glu Pro Pro Gln Ser Thr Gln Asp Pro Glu
                 85                  90

<210> SEQ ID NO 9
<211> LENGTH: 90
<212> TYPE: PRT
<213> ORGANISM: Homo sapiens

<400> SEQUENCE: 9

Ser Ser Val Ser Thr Gly His Thr Thr Pro Leu His Val Thr Asp Ala
  1               5                  10                  15

Ser Ser Ala Ser Thr Gly Gln Ala Thr Pro Leu Pro Val Thr Ser Leu
                 20                  25                  30

Ser Ser Val Ser Thr Gly Asp Thr Thr Pro Leu Pro Val Thr Ser Pro
             35                  40                  45

Ser Ser Ala Ser Thr Gly His Ala Thr Pro Leu Leu Val Thr Asp Thr
         50                  55                  60

Ser Ser Ala Ser Thr Gly His Ala Thr Pro Leu Pro Val Thr Asp Ala
 65                  70                  75                  80

Ser Ser Val Ser Thr Asp His Ala Thr Ser
                 85                  90

<210> SEQ ID NO 10
<211> LENGTH: 90
<212> TYPE: PRT
<213> ORGANISM: Homo sapiens

<400> SEQUENCE: 10

Pro Ala Arg Leu Leu Gly Pro Ser Leu Thr Ser Thr Pro Ala Ser
  1               5                  10                  15

Ser Ser Ser Gly Ser Ser Arg Gly Pro Ser Asp Thr Ser Ser Arg
                 20                  25                  30

Phe Ser Lys Glu Gln Arg Gly Val Ala Gln Pro Leu Ala Gln Leu Arg
             35                  40                  45

Ser Cys Pro Gln Glu Glu Gly Pro Arg Gly Arg Gly Leu Ala Ala Arg
         50                  55                  60

Pro Leu Glu Asn Arg Ala Gly Gly Pro Val Ala Arg Ser Glu Glu Pro
```

```
65                  70                  75                  80

Gly Ala Pro Leu Pro Val Ala Val Gly Thr
                85                  90

<210> SEQ ID NO 11
<211> LENGTH: 90
<212> TYPE: PRT
<213> ORGANISM: Homo sapiens

<400> SEQUENCE: 11

Val Leu Asn Ser Gly Ala Arg Val Trp Pro Ser Ala Ser Ala Leu Gly
1               5                   10                  15

Leu Thr Ala Pro Pro Lys Asp Ala Glu Asp Arg Ala Arg Pro Ala Ser
                20                  25                  30

Gly Leu Arg Gly Ala Arg Val Leu Ser Glu Gly Arg Glu Pro Arg Ala
            35                  40                  45

Ser Leu Arg Val Gln Val Arg Pro Gly Leu Asp Val Ala Ala Pro Gly
    50                  55                  60

Val Cys Ser Leu Ser Cys Pro Ser Pro Arg Ser Ser Ala His Pro
65                  70                  75                  80

Gly Pro Arg Gly Pro Leu Phe Pro Ala Leu
                85                  90

<210> SEQ ID NO 12
<211> LENGTH: 90
<212> TYPE: PRT
<213> ORGANISM: Homo sapiens

<400> SEQUENCE: 12

His Ser Ala Leu Pro Phe Arg Leu Gln Leu Arg Arg Gly Glu Ala Arg
1               5                   10                  15

Leu Gly Glu Glu Arg His Phe Gln Glu Ser Gly Asn Ser Ser Trp Glu
                20                  25                  30

Ile Leu Arg Ala Ser Lys Ala Glu Glu Gly Thr Tyr Glu Cys Thr Ala
            35                  40                  45

Val Ser Arg Ala Gly Thr Gly Arg Ala Lys Ala Gln Ile Val Val Thr
    50                  55                  60

Asp Pro Pro Pro Gln Leu Val Pro Ala Pro Asn Val Thr Val Ser Pro
65                  70                  75                  80

Gly Glu Thr Ala Val Leu Ser Cys Arg Val
                85                  90

<210> SEQ ID NO 13
<211> LENGTH: 90
<212> TYPE: PRT
<213> ORGANISM: Homo sapiens

<400> SEQUENCE: 13

Pro Val Thr Ser Thr Ser Ser Ala Ser Thr Gly His Ala Thr Pro Leu
1               5                   10                  15

Pro Val Thr Gly Leu Ser Ser Ala Thr Thr Asp Asp Thr Thr Arg Leu
                20                  25                  30

Pro Val Thr Asp Val Ser Ser Ala Ser Gly Gln Ala Thr Pro Leu
            35                  40                  45

Pro Val Thr Ser Leu Ser Ser Val Ser Thr Gly Asp Thr Thr Pro Leu
    50                  55                  60

Pro Val Thr Ser Pro Ser Ser Ala Ser Thr Gly His Ala Ser Pro Leu
65                  70                  75                  80
```

Leu Val Thr Asp Ala Ser Ser Ala Ser Thr
            85                  90

<210> SEQ ID NO 14
<211> LENGTH: 90
<212> TYPE: PRT
<213> ORGANISM: Homo sapiens

<400> SEQUENCE: 14

Tyr Val Ala Pro Leu Thr Ala Gln Pro Ala Thr Tyr Arg Ala Gln Pro
1               5                   10                  15

Ser Val Ser Leu Gly Ala Ala Tyr Arg Ala Gln Pro Ser Ala Ser Leu
            20                  25                  30

Gly Val Gly Tyr Arg Thr Gln Pro Met Thr Ala Gln Ala Ala Ser Tyr
        35                  40                  45

Arg Ala Gln Pro Ser Val Ser Leu Gly Ala Pro Tyr Arg Gly Gln Leu
    50                  55                  60

Ala Ser Pro Ser Ser Gln Ser Ala Ala Ser Ser Leu Gly Pro Tyr
65                  70                  75                  80

Gly Gly Ala Gln Pro Ser Ala Ser Ala Leu
            85                  90

<210> SEQ ID NO 15
<211> LENGTH: 90
<212> TYPE: PRT
<213> ORGANISM: Homo sapiens

<400> SEQUENCE: 15

Arg Leu Ala Leu Pro Leu Arg Ser Leu Ser Ala Ser Ser Gly Trp Asn
1               5                   10                  15

Glu Ser Cys Ser Ser Gln Ser Asp Ile Ser Leu Asp His Val Gln Arg
            20                  25                  30

Arg Arg Ser Arg Leu Lys Glu Pro Pro Glu Leu Gln Ser Ser Glu Arg
        35                  40                  45

Ala Ala Gly Ser Pro Pro Ala Pro Gly Thr Met Ser Lys His Arg Gly
    50                  55                  60

Lys Ser Ser Ala Thr Cys Arg Cys Cys Val Thr Tyr Cys Glu Gly Glu
65                  70                  75                  80

Asn His Leu Arg Asn Lys Ser Arg Ala Glu
            85                  90

<210> SEQ ID NO 16
<211> LENGTH: 90
<212> TYPE: PRT
<213> ORGANISM: Homo sapiens

<400> SEQUENCE: 16

Ala Thr Pro Gly Ala Pro Gly Ser Ser Thr Pro Gly Glu Ala Asp Ile
1               5                   10                  15

Gly Asn Thr Ser Phe Gly Lys Ser Gly Lys Ser Gly His Asp Ser Leu
            20                  25                  30

Thr Val Leu Asn Pro Ala Phe Leu Arg Arg Thr Pro Thr Val Ser Ala
        35                  40                  45

Ala Ser Thr Thr Ser Ser Pro Val Ser Lys His Thr Asp Ala Ala Ser
    50                  55                  60

Ala Thr Ala Val Thr Ile Ser Gly Ser Lys Pro Gly Pro Gly Thr
65                  70                  75                  80

```
Pro Gly Gly Ala Thr Ser Gly Gly Lys Ile
                85                  90
```

<210> SEQ ID NO 17
<211> LENGTH: 89
<212> TYPE: PRT
<213> ORGANISM: Homo sapiens

<400> SEQUENCE: 17

```
Lys Ala Gly Val Val Thr Leu His Ser Val Gly Pro Thr Ala Ala Thr
1               5                   10                  15

Gly Thr Thr Ala Gly Thr Gly Leu Leu Gln Thr Ser Lys Pro Leu Val
                20                  25                  30

Thr Ser Val Ala Asn Thr Val Thr Thr Val Ser Leu Gln Pro Glu Lys
            35                  40                  45

Pro Val Val Ser Gly Thr Ala Val Thr Leu Ser Leu Pro Ala Val Thr
        50                  55                  60

Phe Gly Glu Thr Ser Gly Ala Ala Ile Cys Leu Pro Ser Val Lys Pro
65                  70                  75                  80

Val Val Ser Ser Ala Gly Thr Thr Ser
                85
```

<210> SEQ ID NO 18
<211> LENGTH: 90
<212> TYPE: PRT
<213> ORGANISM: Homo sapiens

<400> SEQUENCE: 18

```
Met Glu Leu Gln Ser Arg Pro Glu Ala Leu Ala Val Glu Leu Ala Arg
1               5                   10                  15

His Gln Asn Gly Asp Leu Lys Lys Gln Leu His Glu Arg Gln Pro Arg
                20                  25                  30

Ile Ala Ala Leu Ser Asp Lys Gln Ala Leu Gly Thr Ile Thr Ala Val
            35                  40                  45

Pro Val Thr Gly Pro Gln Val Ser Ser Leu Gln Arg Leu Ala Gly Gln
        50                  55                  60

Gly Ala Ala Val Leu Pro Gln Val Arg Pro Lys Thr Leu Ile Pro Asp
65                  70                  75                  80

Ser Leu Pro Val Ala Pro Gly Arg Asp Arg
                85                  90
```

<210> SEQ ID NO 19
<211> LENGTH: 90
<212> TYPE: PRT
<213> ORGANISM: Homo sapiens

<400> SEQUENCE: 19

```
Ile Ala Ala Lys Ala Gln Leu Ala Arg Gln Gln Ser Pro Ser Pro Ile
1               5                   10                  15

Arg His Ser Pro Ser Pro Val Arg His Val Arg Ala Pro Thr Pro Ser
                20                  25                  30

Pro Val Arg Ser Val Ser Pro Ala Ala Arg Ile Ser Thr Ser Pro Ile
            35                  40                  45

Arg Ser Val Arg Ser Pro Leu Leu Met Arg Lys Thr Gln Ala Ser Thr
        50                  55                  60

Val Ala Thr Gly Pro Glu Val Pro Pro Trp Lys Gln Glu Gly Tyr
65                  70                  75                  80

Val Ala Ser Ser Ser Glu Ala Glu Met Arg
```

```
                85                  90

<210> SEQ ID NO 20
<211> LENGTH: 89
<212> TYPE: PRT
<213> ORGANISM: Homo sapiens

<400> SEQUENCE: 20

Ala Arg Ser Ile Ala Ser Gln Val Gly Ile Thr Lys Val Phe Ala Glu
1               5                   10                  15

Val Leu Pro Ser His Lys Val Ala Lys Val Lys Gln Leu Gln Glu Glu
                20                  25                  30

Gly Lys Arg Val Ala Met Val Gly Asp Gly Ile Asn Asp Ser Pro Ala
            35                  40                  45

Leu Ala Met Ala Asn Val Ile Ala Ile Gly Thr Gly Thr Asp Val Ala
        50                  55                  60

Ile Glu Ala Ala Asp Val Val Leu Ile Arg Asn Asp Leu Leu Asp Val
65                  70                  75                  80

Val Ala Ser Ile Asp Leu Ser Arg Glu
                85

<210> SEQ ID NO 21
<211> LENGTH: 90
<212> TYPE: PRT
<213> ORGANISM: Homo sapiens

<400> SEQUENCE: 21

Lys Val Ala Thr Leu Pro Leu Ser Ser Arg Ala Gly Ala Pro Pro Ala
1               5                   10                  15

Ala Val Pro Ile Ile Asn Met Ile Leu Pro Thr Val Pro Ala Leu Pro
                20                  25                  30

Gly Pro Gly Pro Gly Pro Gly Arg Ala Pro Pro Gly Gly Leu Thr Gln
            35                  40                  45

Pro Arg Gly Thr Glu Asn Arg Glu Val Gly Ile Gly Asp Gln Gly
        50                  55                  60

Pro His Asp Lys Gly Val Lys Arg Thr Ala Glu Val Pro Val Ser Glu
65                  70                  75                  80

Ala Ser Gly Gln Ala Pro Pro Ala Lys Ala
                85                  90

<210> SEQ ID NO 22
<211> LENGTH: 90
<212> TYPE: PRT
<213> ORGANISM: Homo sapiens

<400> SEQUENCE: 22

Glu Pro Glu Pro Thr Pro Gly Leu Val Leu Ser Lys Pro Ala Leu Glu
1               5                   10                  15

Glu Glu Glu Ala Pro Arg Ala Leu Ser Leu Leu Ser Leu Pro Pro Lys
                20                  25                  30

Lys Arg Ser Ile Leu Gly Leu Gly Gln Ala Arg Pro Leu Glu Phe Leu
            35                  40                  45

Arg Thr Cys Tyr Gly Gly Ser Phe Leu Val His Glu Ser Phe Leu Tyr
        50                  55                  60

Lys Arg Glu Lys Ala Val Gly Asp Lys Val Tyr Trp Thr Cys Arg Asp
65                  70                  75                  80

His Ala Leu His Gly Cys Arg Ser Arg Ala
                85                  90
```

<210> SEQ ID NO 23
<211> LENGTH: 90
<212> TYPE: PRT
<213> ORGANISM: Homo sapiens

<400> SEQUENCE: 23

Glu Ile Val Pro Ala Ser Leu Gln Arg Val Arg Arg Pro Val Ala Met
1               5                   10                  15

Val Met Pro Ala Arg Arg Thr Pro His Val Gln Ala Val Gln Gly Pro
            20                  25                  30

Leu Gly Ser Pro Pro Lys Arg Gly Pro Leu Pro Thr Glu Gly Gln Arg
        35                  40                  45

Val Tyr Arg Arg Lys Glu Leu Glu Glu Val Ser Pro Glu Thr Pro Val
50                  55                  60

Val Pro Ala Thr Thr Gln Arg Thr Leu Ala Arg Pro Gly Pro Glu Pro
65                  70                  75                  80

Ala Pro Ala Thr Asp Glu Arg Asp Arg Val
            85                  90

<210> SEQ ID NO 24
<211> LENGTH: 90
<212> TYPE: PRT
<213> ORGANISM: Homo sapiens

<400> SEQUENCE: 24

Ser Thr Arg Pro Val Leu Ala Ser Ile Glu Pro Glu Leu Pro Met Gln
1               5                   10                  15

Leu Val Ser Gln Asp Asp Glu Ser Gly Gln Lys Lys Leu His Gly Leu
            20                  25                  30

Gln Ala Ile Leu Val His Glu Ala Ser Gly Thr Thr Ala Ile Thr Ala
        35                  40                  45

Thr Ala Thr Gly Tyr Gln Glu Ser His Leu Ser Ser Ala Arg Thr Lys
50                  55                  60

Gln Pro His Asp Pro Leu Val Pro Leu Ser Ala Ser Ile Glu Leu Ile
65                  70                  75                  80

Leu Val Glu Asp Val Arg Val Ser Pro Glu
            85                  90

<210> SEQ ID NO 25
<211> LENGTH: 90
<212> TYPE: PRT
<213> ORGANISM: Homo sapiens

<400> SEQUENCE: 25

Ala Arg Gln Glu Lys Leu Ala Phe Gln Glu Asp Ser Arg Ser Thr Leu
1               5                   10                  15

Ser Arg Arg Glu Leu Asp Ala Ala His Thr Gly Thr Thr Gly Gln Asp
            20                  25                  30

Ser Asp Phe Pro Val Thr Ala Ala Ser Thr Val Asp Phe Leu Lys Ile
        35                  40                  45

Lys Lys Ser Cys Glu Glu Asn Val Cys Arg Ser Leu Lys Asp Cys Glu
50                  55                  60

Met Glu Lys Cys Pro Asp Ser Cys Ala His Glu Met Glu Ser Val Ala
65                  70                  75                  80

Asp His Glu Pro Asn Lys Arg Ile Leu Gly
            85                  90

<210> SEQ ID NO 26
<211> LENGTH: 90
<212> TYPE: PRT
<213> ORGANISM: Homo sapiens

<400> SEQUENCE: 26

Ala Glu Thr Glu Glu Thr Arg Ala Glu Glu Asp Glu Glu Glu Glu Glu
1               5                   10                  15

Ala Lys Glu Ala Glu Asp Gly Pro Met Glu Glu Ser Lys Pro Lys Pro
            20                  25                  30

Arg Ser Phe Met Pro Asn Leu Val Pro Pro Lys Ile Pro Asp Gly Glu
        35                  40                  45

Arg Val Asp Phe Asp Asp Ile His Arg Lys Arg Met Glu Lys Asp Leu
    50                  55                  60

Asn Glu Leu Gln Ala Leu Ile Glu Ala His Phe Glu Asn Arg Lys Lys
65                  70                  75                  80

Glu Glu Glu Glu Leu Val Ser Leu Lys Asp
                85                  90

<210> SEQ ID NO 27
<211> LENGTH: 90
<212> TYPE: PRT
<213> ORGANISM: Homo sapiens

<400> SEQUENCE: 27

Met Ser Asp Ile Glu Glu Val Val Glu Glu Tyr Glu Glu Glu Glu Gln
1               5                   10                  15

Glu Glu Ala Ala Val Glu Glu Glu Glu Asp Trp Arg Glu Asp Glu Asp
            20                  25                  30

Glu Gln Glu Glu Ala Ala Glu Glu Asp Ala Glu Ala Glu Ala Glu Thr
        35                  40                  45

Glu Glu Thr Arg Ala Glu Glu Asp Glu Glu Glu Glu Glu Ala Lys Glu
    50                  55                  60

Ala Glu Asp Gly Pro Met Glu Glu Ser Lys Pro Lys Pro Arg Ser Phe
65                  70                  75                  80

Met Pro Asn Leu Val Pro Pro Lys Ile Pro
                85                  90

<210> SEQ ID NO 28
<211> LENGTH: 90
<212> TYPE: PRT
<213> ORGANISM: Homo sapiens

<400> SEQUENCE: 28

Ser Ser Ala Leu Ser Gly Ser Gly Ile Ser Arg Met Gln Arg Pro Ser
1               5                   10                  15

Ser Glu Ala Gln Met Arg Met Val Ala Ser Ser Glu Val Asp Thr Arg
            20                  25                  30

Met Ser Leu Glu Arg Asp Gln Ala Lys Ser Glu Thr Pro Arg Val Trp
        35                  40                  45

Pro Arg Ser Thr Arg Ser Thr Val Gly Gly Ala Gly Thr Ser Trp His
    50                  55                  60

Arg Glu Met Leu Pro Ser Arg Pro Glu Asp His Pro Gln Thr His Leu
65                  70                  75                  80

His Ala Val Lys Ser Ser Ala Ala Thr Ala
                85                  90

```
<210> SEQ ID NO 29
<211> LENGTH: 90
<212> TYPE: PRT
<213> ORGANISM: Homo sapiens

<400> SEQUENCE: 29

Met Val Gln Leu Arg Pro Arg Ala Ser Arg Pro Ala Ser Ala Glu
1               5                   10                  15

Ala Met Val Asp Glu Gly Gln Leu Ala Ser Glu Glu Glu Ala Glu
                20                  25                  30

His Gly Leu Leu Leu Gly Gln Pro Ser Ser Gly Ala Ala Ala Glu Pro
            35                  40                  45

Leu Glu Glu Asp Glu Glu Gly Asp Asp Glu Phe Asp Asp Glu Ala Pro
    50                  55                  60

Glu Glu Leu Thr Phe Ala Ser Ala Gln Ala Glu Ala Arg Glu Glu
65                  70                  75                  80

Arg Arg Val Arg Glu Thr Val Arg Arg Asp
                85                  90

<210> SEQ ID NO 30
<211> LENGTH: 90
<212> TYPE: PRT
<213> ORGANISM: Homo sapiens

<400> SEQUENCE: 30

Pro Arg Ala His Pro Ala Pro Ser Met Gly Ser Leu Arg Asn Glu Phe
1               5                   10                  15

Trp Phe Ser Asp Gly Ser Leu Ser Asp Lys Ser Lys Cys Ala Asp Pro
                20                  25                  30

Gly Leu Met Pro Leu Pro Asp Thr Ala Thr Gly Leu Asp Trp Thr His
            35                  40                  45

Leu Val Asp Ala Ala Arg Ala Phe Glu Gly Leu Asp Ser Asp Glu Glu
    50                  55                  60

Leu Gly Leu Leu Cys His His Thr Ser Tyr Leu Asp Gln Arg Val Ala
65                  70                  75                  80

Ser Phe Cys Thr Leu Thr Asp Met Gln His
                85                  90

<210> SEQ ID NO 31
<211> LENGTH: 90
<212> TYPE: PRT
<213> ORGANISM: Homo sapiens

<400> SEQUENCE: 31

Met Leu Gln Lys Pro Arg Asn Arg Gly Arg Ser Gly Gly Gln Ala Glu
1               5                   10                  15

Arg Asp Arg Asp Trp Ser His Ser Gly Asn Pro Gly Ala Ser Arg Ala
                20                  25                  30

Gly Glu Asp Ala Arg Val Leu Arg Asp Gly Phe Ala Glu Glu Ala Pro
            35                  40                  45

Ser Thr Ser Arg Gly Pro Gly Gly Ser Gln Gly Ser Gln Gly Pro Ser
    50                  55                  60

Pro Gln Gly Ala Arg Arg Ala Gln Ala Ala Pro Ala Val Gly Pro Arg
65                  70                  75                  80

Ser Gln Lys Gln Leu Glu Leu Lys Val Ser
                85                  90

<210> SEQ ID NO 32
```

```
<211> LENGTH: 90
<212> TYPE: PRT
<213> ORGANISM: Homo sapiens

<400> SEQUENCE: 32

Val Glu Val Trp Ile Gly Met Thr Ile Glu Glu Leu Ala Arg Ala Met
1               5                   10                  15

Glu Lys Asn Thr Asp Tyr Val Tyr Glu Ala Leu Leu Asn Thr Asp Ile
            20                  25                  30

Asp Ile Asp Ser Leu Glu Ala Asp Ser His Leu Asp Glu Val Trp Ile
        35                  40                  45

Lys Glu Val Ile Thr Lys Ala Gly Met Lys Leu Lys Trp Ser Lys Leu
    50                  55                  60

Lys Gln Asp Lys Val Arg Lys Asn Lys Asp Ala Val Arg Arg Pro Gln
65                  70                  75                  80

Ala Asp Pro Ala Leu Leu Thr Pro Arg Ser
                85                  90

<210> SEQ ID NO 33
<211> LENGTH: 90
<212> TYPE: PRT
<213> ORGANISM: Homo sapiens

<400> SEQUENCE: 33

Pro Val Thr Pro Gln Pro Arg Ser Ile Ser Gly Pro Ser Val Gly Val
1               5                   10                  15

Met Glu Met Arg Ser Pro Leu Leu Ala Gly Gly Ser Pro Pro Gln Pro
            20                  25                  30

Val Val Pro Ala His Lys Asp Lys Ser Gly Ala Pro Pro Val Arg Ser
        35                  40                  45

Ile Tyr Asp Asp Ile Ser Ser Pro Gly Leu Gly Ser Thr Pro Leu Thr
    50                  55                  60

Ser Arg Arg Gln Pro Asn Ile Ser Val Met Gln Ser Pro Leu Val Gly
65                  70                  75                  80

Val Thr Ser Thr Pro Gly Thr Gly Gln Ser
                85                  90

<210> SEQ ID NO 34
<211> LENGTH: 90
<212> TYPE: PRT
<213> ORGANISM: Homo sapiens

<400> SEQUENCE: 34

Met Ser Asp Ile Glu Glu Val Val Glu Glu Tyr Glu Glu Glu Glu Gln
1               5                   10                  15

Glu Glu Gln Glu Glu Ala Ala Glu Glu Asp Ala Glu Ala Glu Ala Glu
            20                  25                  30

Thr Glu Glu Thr Arg Ala Glu Glu Asp Glu Glu Glu Glu Glu Ala Lys
        35                  40                  45

Glu Ala Glu Asp Gly Pro Met Glu Glu Ser Lys Pro Lys Pro Arg Ser
    50                  55                  60

Phe Met Pro Asn Leu Val Pro Pro Lys Ile Pro Asp Gly Glu Arg Val
65                  70                  75                  80

Asp Phe Asp Asp Ile His Arg Lys Arg Met
                85                  90

<210> SEQ ID NO 35
<211> LENGTH: 90
```

<212> TYPE: PRT
<213> ORGANISM: Homo sapiens

<400> SEQUENCE: 35

Leu Leu Pro Arg Ser Ala Gly Arg Pro Asp Pro Gln Ser Gln Leu Pro
1               5                   10                  15

Glu Arg Thr Gly Ala Glu Trp Asn Pro Leu Ser Phe Ser Leu Ala
            20                  25                  30

Ser Arg Gly Leu Ser Gly Gln Tyr Val Thr Leu Asp Asn Arg Ser Gly
            35                  40                  45

Glu Leu His Thr Ser Ala Gln Glu Ile Asp Arg Glu Ala Leu Cys Val
    50                  55                  60

Glu Gly Gly Gly Gly Thr Ala Trp Ser Gly Ser Val Ser Ile Ser Ser
65                  70                  75                  80

Ser Pro Ser Asp Ser Cys Leu Leu Leu Leu
                85                  90

<210> SEQ ID NO 36
<211> LENGTH: 90
<212> TYPE: PRT
<213> ORGANISM: Homo sapiens

<400> SEQUENCE: 36

Asp Ser Ser Lys Pro Ile Val Arg Glu Ser Trp Met Thr Glu Leu Pro
1               5                   10                  15

Pro Glu Met Lys Asp Phe Gly Leu Gly Pro Arg Thr Phe Lys Arg Arg
            20                  25                  30

Ala Asp Asp Thr Ser Gly Asp Arg Ser Ile Trp Thr Asp Thr Pro Ala
            35                  40                  45

Asp Arg Glu Arg Lys Ala Lys Glu Thr Gln Gly Ala Arg Lys Ser Ser
    50                  55                  60

Ser Lys Lys Asp Glu Glu His Ile Leu Ser Gly Arg Asp Lys Arg Leu
65                  70                  75                  80

Ala Glu Gln Val Ser Ser Tyr Asn Glu Ser
                85                  90

<210> SEQ ID NO 37
<211> LENGTH: 90
<212> TYPE: PRT
<213> ORGANISM: Homo sapiens

<400> SEQUENCE: 37

Met Gly Gln Gln Val Gly Arg Val Gly Glu Ala Pro Gly Leu Gln Gln
1               5                   10                  15

Pro Gln Pro Arg Gly Ile Arg Gly Ser Ser Ala Ala Arg Pro Ser Gly
            20                  25                  30

Arg Arg Arg Asp Pro Ala Gly Arg Thr Thr Glu Thr Gly Phe Asn Ile
            35                  40                  45

Phe Thr Gln His Asp His Phe Ala Ser Cys Val Glu Asp Gly Phe Glu
    50                  55                  60

Gly Asp Lys Thr Gly Gly Ser Ser Pro Glu Ala Leu His Arg Pro Tyr
65                  70                  75                  80

Gly Cys Asp Val Glu Pro Gln Ala Leu Asn
                85                  90

<210> SEQ ID NO 38
<211> LENGTH: 90
<212> TYPE: PRT

<213> ORGANISM: Homo sapiens

<400> SEQUENCE: 38

Pro Gly Ser Pro Val Arg Ala Gly Ala Ser Ile Pro Ser Ser Gly Ala
1               5                   10                  15

Ala Ser Pro Arg Gly Phe Pro Leu Gly Leu Ser Ala Lys Ser Gly Gly
            20                  25                  30

Gly Pro Gly Ser Gly Pro Arg Arg Thr Ser Ser Glu Glu Leu Arg Asp
        35                  40                  45

Ala Thr Ser Leu Leu Ala Ala Gly Glu Gly Gly Leu Leu Asp Glu Val
    50                  55                  60

Glu Pro Leu Arg Pro Asp Glu Leu Glu Arg Leu Ser Gly Trp Glu Glu
65                  70                  75                  80

Glu Glu Glu Ser Trp Leu Tyr Ser Ser Pro
                85                  90

<210> SEQ ID NO 39
<211> LENGTH: 90
<212> TYPE: PRT
<213> ORGANISM: Homo sapiens

<400> SEQUENCE: 39

Ala Pro Leu Pro Arg Ser Asn Arg Ser Arg Cys Pro Gly Thr Arg Gln
1               5                   10                  15

Pro Gly Ala Ala Ser Leu His Ala Ala Ser Ala Ala Val Pro Val Arg
            20                  25                  30

Pro Arg Arg Gly Thr Ala Pro Ala Gly Lys Thr Ala Asp Ala Val Pro
        35                  40                  45

Ala Ala Ala Pro Glu Gln Ala Pro Arg Pro Ala Pro Gln Ser Arg Lys
    50                  55                  60

Pro Arg Asn Leu Glu Gly Asp Leu Asp Glu Arg Arg Leu Leu Cys His
65                  70                  75                  80

Leu Gln Leu Ala Gln Asp Arg Glu Ala Arg
                85                  90

<210> SEQ ID NO 40
<211> LENGTH: 90
<212> TYPE: PRT
<213> ORGANISM: Homo sapiens

<400> SEQUENCE: 40

Leu Gly Arg Leu Gln Gly Gln Pro Leu Arg Asp Gly Glu Glu Val Val
1               5                   10                  15

Leu Leu Leu Glu Gly Ile His Arg Glu Pro Ser His Ala Gly Pro Leu
            20                  25                  30

Asp Phe Ser Cys Asn Ala Gly Lys Ser Cys Pro Arg Ala Asp Val Thr
        35                  40                  45

Leu Glu Glu Lys Gly Cys Ala Ser Gln Val Pro Ser His Ser Pro Lys
    50                  55                  60

Lys Glu Leu Pro Ala Glu Glu Pro Ser Val Leu Gly Pro Ser Asp Glu
65                  70                  75                  80

Pro Pro Arg Pro Gln Pro Arg Ala Ala Gln
                85                  90

<210> SEQ ID NO 41
<211> LENGTH: 89
<212> TYPE: PRT
<213> ORGANISM: Homo sapiens

<400> SEQUENCE: 41

Ser Glu Leu Ala Gln Asn Lys Glu Leu Thr Pro Gly Ala Pro Gln
1               5                   10                  15

His Gln Leu Pro Pro Val Pro Gly Ser Pro Glu Pro Tyr Pro Gly Gln
            20                  25                  30

Gln Ala Pro Gly Pro Glu Pro Ser Gln Pro Leu Leu Glu Leu Thr Pro
        35                  40                  45

Arg Ala Pro Gly Ser Pro Arg Gly Gln His Glu Pro Ser Lys Pro Pro
    50                  55                  60

Pro Ala Gly Glu Thr Val Thr Gly Gly Phe Gly Ala Lys Lys Arg Lys
65                  70                  75                  80

Gly Ser Ser Gln Ala Pro Ala Ser Lys
                85

<210> SEQ ID NO 42
<211> LENGTH: 90
<212> TYPE: PRT
<213> ORGANISM: Homo sapiens

<400> SEQUENCE: 42

Ala Thr Phe Ile Arg Asp Gly Tyr Asn Asn Val Pro Ser Val Gly Ser
1               5                   10                  15

Leu Ala Asp Pro Asp Tyr Leu Asn Thr Pro Gln Met Asn Thr Pro Val
            20                  25                  30

Thr Leu Asn Ser Ala Ala Pro Ala Ser Asn Ser Gly Ala Gly Val Leu
        35                  40                  45

Pro Ser Pro Ala Thr Pro Arg Phe Ser Val Pro Thr Pro Arg Thr Pro
    50                  55                  60

Arg Thr Pro Arg Thr Pro Arg Gly Gly Gly Thr Ala Ser Gly Gln Gly
65                  70                  75                  80

Ser Val Lys Tyr Asp Ser Thr Asp Gln Gly
                85                  90

<210> SEQ ID NO 43
<211> LENGTH: 90
<212> TYPE: PRT
<213> ORGANISM: Homo sapiens

<400> SEQUENCE: 43

Ala Gly Leu Gly Arg Ala Gly Asp Ser Ala Val Leu Val Leu Pro Pro
1               5                   10                  15

Ser Pro Gly Pro Arg Ser Ser Arg Pro Ser Met Asp Ser Glu Gly Gly
            20                  25                  30

Ser Leu Leu Leu Asp Glu Asp Ser Glu Val Phe Lys Met Leu Gln Glu
        35                  40                  45

Asn Arg Glu Gly Arg Ala Ala Pro Arg Gln Ser Ser Ser Phe Arg Leu
    50                  55                  60

Leu Gln Glu Ala Leu Glu Ala Glu Glu Arg Gly Gly Thr Pro Ala Phe
65                  70                  75                  80

Leu Pro Ser Ser Leu Ser Pro Gln Ser Ser
                85                  90

<210> SEQ ID NO 44
<211> LENGTH: 89
<212> TYPE: PRT
<213> ORGANISM: Homo sapiens

<400> SEQUENCE: 44

Ser Leu Glu Ala Leu Gly Met Pro Arg Ala Tyr Arg Leu Pro Ser Ser
1               5                   10                  15

Phe Glu Arg Val Pro Cys Gln Thr Glu Ser Ser Gly Pro Val Pro Thr
            20                  25                  30

Ile Asp Arg Ala Gly Thr Glu Phe Asp Met Ala Ala Lys His Leu Gln
        35                  40                  45

Ser Gln Ser Thr Pro Gln Ala Gln Ala Arg Ser Lys Gly Ser Val Ala
    50                  55                  60

Leu Met Asn Glu Lys Gln Lys Pro His Leu Gln Gly Ser Glu Leu Arg
65                  70                  75                  80

Thr Glu Lys Leu Leu Ser Glu Gly Leu
                85

<210> SEQ ID NO 45
<211> LENGTH: 90
<212> TYPE: PRT
<213> ORGANISM: Homo sapiens

<400> SEQUENCE: 45

Met Ser Asp Ile Glu Glu Val Val Glu Tyr Glu Glu Glu Glu Glu Gln
1               5                   10                  15

Glu Glu Ala Ala Val Glu Glu Gln Glu Leu Ala Ala Glu Glu Asp Ala
            20                  25                  30

Glu Ala Glu Ala Glu Thr Glu Glu Thr Arg Ala Glu Glu Asp Glu Glu
        35                  40                  45

Glu Glu Glu Ala Lys Glu Ala Glu Asp Gly Pro Met Glu Glu Ser Lys
    50                  55                  60

Pro Lys Pro Arg Ser Phe Met Pro Asn Leu Val Pro Pro Lys Ile Pro
65                  70                  75                  80

Asp Gly Glu Arg Val Asp Phe Asp Asp Ile
                85                  90

<210> SEQ ID NO 46
<211> LENGTH: 9
<212> TYPE: PRT
<213> ORGANISM: Artificial Sequence
<220> FEATURE:
<223> OTHER INFORMATION: HA tag

<400> SEQUENCE: 46

Tyr Pro Tyr Asp Val Pro Asp Tyr Ala
1               5

<210> SEQ ID NO 47
<211> LENGTH: 9
<212> TYPE: PRT
<213> ORGANISM: Artificial Sequence
<220> FEATURE:
<223> OTHER INFORMATION: c-Myc tag

<400> SEQUENCE: 47

Glu Gln Lys Leu Ile Ser Glu Glu Asp
1               5

<210> SEQ ID NO 48
<211> LENGTH: 7
<212> TYPE: PRT
<213> ORGANISM: Artificial Sequence
<220> FEATURE:
<223> OTHER INFORMATION: FLAG tag

```
<400> SEQUENCE: 48

Asp Tyr Lys Asp Asp Lys
1               5

<210> SEQ ID NO 49
<211> LENGTH: 14
<212> TYPE: PRT
<213> ORGANISM: Artificial Sequence
<220> FEATURE:
<223> OTHER INFORMATION: V5 tag

<400> SEQUENCE: 49

Gly Lys Pro Ile Pro Asn Pro Leu Leu Gly Leu Asp Ser Thr
1               5                   10

<210> SEQ ID NO 50
<211> LENGTH: 8
<212> TYPE: PRT
<213> ORGANISM: Mus musculus

<400> SEQUENCE: 50

Asp Cys Thr Asp His Ser Asp Glu
1               5

<210> SEQ ID NO 51
<211> LENGTH: 8
<212> TYPE: PRT
<213> ORGANISM: Mus musculus

<400> SEQUENCE: 51

Asp Cys Gly Asp Asn Ser Asp Glu
1               5

<210> SEQ ID NO 52
<211> LENGTH: 8
<212> TYPE: PRT
<213> ORGANISM: Mus musculus

<400> SEQUENCE: 52

Asp Cys Asp Asp Asp Ser Asp Glu
1               5

<210> SEQ ID NO 53
<211> LENGTH: 8
<212> TYPE: PRT
<213> ORGANISM: Mus musculus

<400> SEQUENCE: 53

Asp Cys Pro Asp Tyr Met Asp Glu
1               5

<210> SEQ ID NO 54
<211> LENGTH: 8
<212> TYPE: PRT
<213> ORGANISM: Mus musculus

<400> SEQUENCE: 54

Glu Cys Gln Asp Gly Ser Asp Glu
1               5

<210> SEQ ID NO 55
<211> LENGTH: 8
<212> TYPE: PRT
<213> ORGANISM: Mus musculus
```

<400> SEQUENCE: 55

Asp Cys Asp Asn Gly Ser Asp Glu
1               5

<210> SEQ ID NO 56
<211> LENGTH: 8
<212> TYPE: PRT
<213> ORGANISM: Mus musculus

<400> SEQUENCE: 56

Asp Cys Gly Asp Gly Ser Asp Glu
1               5

<210> SEQ ID NO 57
<211> LENGTH: 8
<212> TYPE: PRT
<213> ORGANISM: Mus musculus

<400> SEQUENCE: 57

Asp Cys Val Asp Gly Ser Asp Glu
1               5

<210> SEQ ID NO 58
<211> LENGTH: 8
<212> TYPE: PRT
<213> ORGANISM: Mus musculus

<400> SEQUENCE: 58

Asp Cys Gln Asp Arg Ser Asp Glu
1               5

<210> SEQ ID NO 59
<211> LENGTH: 8
<212> TYPE: PRT
<213> ORGANISM: Mus musculus

<400> SEQUENCE: 59

Asp Cys Ile Asp Gly Ser Asp Glu
1               5

<210> SEQ ID NO 60
<211> LENGTH: 8
<212> TYPE: PRT
<213> ORGANISM: Mus musculus

<400> SEQUENCE: 60

Asp Cys Pro Asp Gly Ala Asp Glu
1               5

<210> SEQ ID NO 61
<211> LENGTH: 8
<212> TYPE: PRT
<213> ORGANISM: Mus musculus

<400> SEQUENCE: 61

Asp Cys Glu Asn Gly Arg Asp Glu
1               5

<210> SEQ ID NO 62
<211> LENGTH: 8
<212> TYPE: PRT
<213> ORGANISM: Mus musculus

<400> SEQUENCE: 62

Asp Cys Pro Asp Gly Ser Asp Glu
1               5

<210> SEQ ID NO 63
<211> LENGTH: 8
<212> TYPE: PRT
<213> ORGANISM: Mus musculus

<400> SEQUENCE: 63

Asp Cys Glu Gly Gly Ala Asp Glu
1               5

<210> SEQ ID NO 64
<211> LENGTH: 8
<212> TYPE: PRT
<213> ORGANISM: Mus musculus

<400> SEQUENCE: 64

Asp Cys Glu Asp Gly Ser Asp Glu
1               5

<210> SEQ ID NO 65
<211> LENGTH: 8
<212> TYPE: PRT
<213> ORGANISM: Mus musculus

<400> SEQUENCE: 65

Asp Cys Glu Asp Arg Thr Asp Glu
1               5

<210> SEQ ID NO 66
<211> LENGTH: 8
<212> TYPE: PRT
<213> ORGANISM: Mus musculus

<400> SEQUENCE: 66

Asp Cys Ala Asp Gly Ala Asp Glu
1               5

<210> SEQ ID NO 67
<211> LENGTH: 8
<212> TYPE: PRT
<213> ORGANISM: Mus musculus

<400> SEQUENCE: 67

Asp Cys Ala Asp Gly Ser Asp Glu
1               5

<210> SEQ ID NO 68
<211> LENGTH: 8
<212> TYPE: PRT
<213> ORGANISM: Mus musculus

<400> SEQUENCE: 68

Asp Cys Gly Ser Asn Glu Asp Glu
1               5

<210> SEQ ID NO 69
<211> LENGTH: 8
<212> TYPE: PRT
<213> ORGANISM: Mus musculus

<400> SEQUENCE: 69

Asp Cys Gly Asp Gln Thr Asp Glu

<210> SEQ ID NO 70
<211> LENGTH: 8
<212> TYPE: PRT
<213> ORGANISM: Mus musculus

<400> SEQUENCE: 70

Asp Cys Pro Asp His Ser Asp Glu
1               5

<210> SEQ ID NO 71
<211> LENGTH: 8
<212> TYPE: PRT
<213> ORGANISM: Mus musculus

<400> SEQUENCE: 71

Asp Cys Ser Asp Asn Ser Asp Glu
1               5

<210> SEQ ID NO 72
<211> LENGTH: 8
<212> TYPE: PRT
<213> ORGANISM: Mus musculus

<400> SEQUENCE: 72

Asp Cys Leu Asp Ala Ser Asp Glu
1               5

<210> SEQ ID NO 73
<211> LENGTH: 269
<212> TYPE: PRT
<213> ORGANISM: Mus musculus
<220> FEATURE:
<221> NAME/KEY: MISC_FEATURE
<222> LOCATION: (1)..(269)
<223> OTHER INFORMATION: Mouse IL-1B amino acid sequence

<400> SEQUENCE: 73

Met Ala Thr Val Pro Glu Leu Asn Cys Glu Met Pro Pro Phe Asp Ser
1               5                   10                  15

Asp Glu Asn Asp Leu Phe Phe Glu Val Asp Gly Pro Gln Lys Met Lys
                20                  25                  30

Gly Cys Phe Gln Thr Phe Asp Leu Gly Cys Pro Asp Glu Ser Ile Gln
        35                  40                  45

Leu Gln Ile Ser Gln Gln His Ile Asn Lys Ser Phe Arg Gln Ala Val
    50                  55                  60

Ser Leu Ile Val Ala Val Glu Lys Leu Trp Gln Leu Pro Val Ser Phe
65                  70                  75                  80

Pro Trp Thr Phe Gln Asp Glu Asp Met Ser Thr Phe Phe Ser Phe Ile
                85                  90                  95

Phe Glu Glu Glu Pro Ile Leu Cys Asp Ser Trp Asp Asp Asp Asp Asn
            100                 105                 110

Leu Leu Val Cys Asp Val Pro Ile Arg Gln Leu His Tyr Arg Leu Arg
        115                 120                 125

Asp Glu Gln Gln Lys Ser Leu Val Leu Ser Asp Pro Tyr Glu Leu Lys
    130                 135                 140

Ala Leu His Leu Asn Gly Gln Asn Ile Asn Gln Gln Val Ile Phe Ser
145                 150                 155                 160

Met Ser Phe Val Gln Gly Glu Pro Ser Asn Asp Lys Ile Pro Val Ala
                165                 170                 175

Leu Gly Leu Lys Gly Lys Asn Leu Tyr Leu Ser Cys Val Met Lys Asp
            180                 185                 190

Gly Thr Pro Thr Leu Gln Leu Glu Ser Val Asp Pro Lys Gln Tyr Pro
        195                 200                 205

Lys Lys Lys Met Glu Lys Arg Phe Val Phe Asn Lys Ile Glu Val Lys
210                 215                 220

Ser Lys Val Glu Phe Glu Ser Ala Glu Phe Pro Asn Trp Tyr Ile Ser
225                 230                 235                 240

Thr Ser Gln Ala Glu His Lys Pro Val Phe Leu Gly Asn Asn Ser Gly
                245                 250                 255

Gln Asp Ile Ile Asp Phe Thr Met Glu Ser Val Ser Ser
            260                 265

<210> SEQ ID NO 74
<211> LENGTH: 56
<212> TYPE: PRT
<213> ORGANISM: Mus musculus
<220> FEATURE:
<221> NAME/KEY: MISC_FEATURE
<222> LOCATION: (1)..(56)
<223> OTHER INFORMATION: amino acids 0-56 of mouse IL-1B (SEQ ID NO:73)

<400> SEQUENCE: 74

Met Ala Thr Val Pro Glu Leu Asn Cys Glu Met Pro Pro Phe Asp Ser
1               5                   10                  15

Asp Glu Asn Asp Leu Phe Phe Glu Val Asp Gly Pro Gln Lys Met Lys
                20                  25                  30

Gly Cys Phe Gln Thr Phe Asp Leu Gly Cys Pro Asp Glu Ser Ile Gln
            35                  40                  45

Leu Gln Ile Ser Gln Gln His Ile
    50                  55

<210> SEQ ID NO 75
<211> LENGTH: 56
<212> TYPE: PRT
<213> ORGANISM: Mus musculus
<220> FEATURE:
<221> NAME/KEY: MISC_FEATURE
<222> LOCATION: (1)..(56)
<223> OTHER INFORMATION: amino acids 76-131 of mouse IL-1B (SEQ ID
      NO:73)

<400> SEQUENCE: 75

Leu Pro Val Ser Phe Pro Trp Thr Phe Gln Asp Glu Asp Met Ser Thr
1               5                   10                  15

Phe Phe Ser Phe Ile Phe Glu Glu Glu Pro Ile Leu Cys Asp Ser Trp
                20                  25                  30

Asp Asp Asp Asp Asn Leu Leu Val Cys Asp Val Pro Ile Arg Gln Leu
            35                  40                  45

His Tyr Arg Leu Arg Asp Glu Gln
    50                  55

<210> SEQ ID NO 76
<211> LENGTH: 55
<212> TYPE: PRT
<213> ORGANISM: Mus musculus
<220> FEATURE:
<221> NAME/KEY: MISC_FEATURE
<222> LOCATION: (1)..(55)
<223> OTHER INFORMATION: amino acids 112-167 of mouse IL-1B (SEQ ID
      NO:73)

-continued

<400> SEQUENCE: 76

Leu Leu Val Cys Asp Val Pro Ile Arg Gln Leu His Tyr Arg Leu Arg
1               5                   10                  15

Asp Glu Gln Gln Lys Ser Leu Val Leu Ser Asp Pro Tyr Glu Leu Lys
                20                  25                  30

Ala Leu His Leu Asn Gly Gln Asn Ile Asn Gln Gln Val Ile Phe Ser
            35                  40                  45

Met Ser Phe Val Gln Gly Glu
        50                  55

<210> SEQ ID NO 77
<211> LENGTH: 487
<212> TYPE: PRT
<213> ORGANISM: Mus musculus
<220> FEATURE:
<221> NAME/KEY: MISC_FEATURE
<222> LOCATION: (1)..(487)
<223> OTHER INFORMATION: Mouse gsdmd amino acid sequence

<400> SEQUENCE: 77

Met Pro Ser Ala Phe Glu Lys Val Val Lys Asn Val Ile Lys Glu Val
1               5                   10                  15

Ser Gly Ser Arg Gly Asp Leu Ile Pro Val Asp Ser Leu Arg Asn Ser
                20                  25                  30

Thr Ser Phe Arg Pro Tyr Cys Leu Leu Asn Arg Lys Phe Ser Ser Ser
            35                  40                  45

Arg Phe Trp Lys Pro Arg Tyr Ser Cys Val Asn Leu Ser Ile Lys Asp
        50                  55                  60

Ile Leu Glu Pro Ser Ala Pro Glu Pro Glu Pro Glu Cys Phe Gly Ser
65                  70                  75                  80

Phe Lys Val Ser Asp Val Val Asp Gly Asn Ile Gln Gly Arg Val Met
                85                  90                  95

Leu Ser Gly Met Gly Glu Gly Lys Ile Ser Gly Gly Ala Ala Val Ser
            100                 105                 110

Asp Ser Ser Ser Ala Ser Met Asn Val Cys Ile Leu Arg Val Thr Gln
        115                 120                 125

Lys Thr Trp Glu Thr Met Gln His Glu Arg His Leu Gln Gln Pro Glu
130                 135                 140

Asn Lys Ile Leu Gln Gln Leu Arg Ser Arg Gly Asp Asp Leu Phe Val
145                 150                 155                 160

Val Thr Glu Val Leu Gln Thr Lys Glu Glu Val Gln Ile Thr Glu Val
                165                 170                 175

His Ser Gln Glu Gly Ser Gly Gln Phe Thr Leu Pro Gly Ala Leu Cys
            180                 185                 190

Leu Lys Gly Glu Gly Lys Gly His Gln Ser Arg Lys Lys Met Val Thr
        195                 200                 205

Ile Pro Ala Gly Ser Ile Leu Ala Phe Arg Val Ala Gln Leu Leu Ile
210                 215                 220

Gly Ser Lys Trp Asp Ile Leu Val Ser Asp Glu Lys Gln Arg Thr
225                 230                 235                 240

Phe Glu Pro Ser Ser Gly Asp Arg Lys Ala Val Gly Gln Arg His His
                245                 250                 255

Gly Leu Asn Val Leu Ala Ala Leu Cys Ser Ile Gly Lys Gln Leu Ser
            260                 265                 270

Leu Leu Ser Asp Gly Ile Asp Glu Glu Glu Leu Ile Glu Ala Ala Asp
        275                 280                 285

```
Phe Gln Gly Leu Tyr Ala Glu Val Lys Ala Cys Ser Ser Glu Leu Glu
        290                 295                 300

Ser Leu Glu Met Glu Leu Arg Gln Gln Ile Leu Val Asn Ile Gly Lys
305                 310                 315                 320

Ile Leu Gln Asp Gln Pro Ser Met Glu Ala Leu Glu Ala Ser Leu Gly
                325                 330                 335

Gln Gly Leu Cys Ser Gly Gln Val Glu Pro Leu Asp Gly Pro Ala
            340                 345                 350

Gly Cys Ile Leu Glu Cys Leu Val Leu Asp Ser Gly Glu Leu Val Pro
        355                 360                 365

Glu Leu Ala Ala Pro Ile Phe Tyr Leu Leu Gly Ala Leu Ala Val Leu
    370                 375                 380

Ser Glu Thr Gln Gln Gln Leu Ala Lys Ala Leu Glu Thr Thr Val
385                 390                 395                 400

Leu Ser Lys Gln Leu Glu Leu Val Lys His Val Leu Glu Gln Ser Thr
                405                 410                 415

Pro Trp Gln Glu Gln Ser Ser Val Ser Leu Pro Thr Val Leu Leu Gly
                420                 425                 430

Asp Cys Trp Asp Glu Lys Asn Pro Thr Trp Val Leu Leu Glu Glu Cys
            435                 440                 445

Gly Leu Arg Leu Gln Val Glu Ser Pro Gln Val His Trp Glu Pro Thr
    450                 455                 460

Ser Leu Ile Pro Thr Ser Ala Leu Tyr Ala Ser Leu Phe Leu Leu Ser
465                 470                 475                 480

Ser Leu Gly Gln Lys Pro Cys
                485

<210> SEQ ID NO 78
<211> LENGTH: 56
<212> TYPE: PRT
<213> ORGANISM: Mus musculus
<220> FEATURE:
<221> NAME/KEY: MISC_FEATURE
<222> LOCATION: (1)..(56)
<223> OTHER INFORMATION: amino acids 223-278 of mouse gsdmd (SEQ ID
      NO:77)

<400> SEQUENCE: 78

Leu Ile Gly Ser Lys Trp Asp Ile Leu Leu Val Ser Asp Glu Lys Gln
1               5                   10                  15

Arg Thr Phe Glu Pro Ser Ser Gly Asp Arg Lys Ala Val Gly Gln Arg
                20                  25                  30

His His Gly Leu Asn Val Leu Ala Ala Leu Cys Ser Ile Gly Lys Gln
            35                  40                  45

Leu Ser Leu Leu Ser Asp Gly Ile
        50                  55

<210> SEQ ID NO 79
<211> LENGTH: 56
<212> TYPE: PRT
<213> ORGANISM: Mus musculus
<220> FEATURE:
<221> NAME/KEY: MISC_FEATURE
<222> LOCATION: (1)..(56)
<223> OTHER INFORMATION: amino acids 260-315 of mouse gsdmd (SEQ ID
      NO:77)

<400> SEQUENCE: 79

Val Leu Ala Ala Leu Cys Ser Ile Gly Lys Gln Leu Ser Leu Leu Ser
```

-continued

```
1               5                   10                  15
Asp Gly Ile Asp Glu Glu Leu Ile Glu Ala Ala Asp Phe Gln Gly
            20                  25              30

Leu Tyr Ala Glu Val Lys Ala Cys Ser Ser Glu Leu Glu Ser Leu Glu
        35              40              45

Met Glu Leu Arg Gln Gln Ile Leu
50              55
```